(12) United States Patent
Nakano et al.

(10) Patent No.: US 8,569,580 B2
(45) Date of Patent: Oct. 29, 2013

(54) TRANSFORMED PLANTS OR ALGAE WITH HIGHLY EXPRESSED CHLOROPLAST PROTEIN BPG2

(75) Inventors: Takeshi Nakano, Saitama (JP); Tadao Asami, Saitama (JP); Ayumi Yamagami, Saitama (JP); Setsuko Shimada, Saitama (JP); Minami Matsui, Kanagawa (JP)

(73) Assignee: Riken, Wako-Shi, Saitama (JP)

( * ) Notice: Subject to any disclaimer, the term of this patent is extended or adjusted under 35 U.S.C. 154(b) by 679 days.

(21) Appl. No.: 12/661,326

(22) Filed: Mar. 15, 2010

(65) Prior Publication Data

US 2011/0225674 A1    Sep. 15, 2011

(51) Int. Cl.
*A01H 5/00* (2006.01)
*A01H 5/10* (2006.01)
*C12N 15/29* (2006.01)
*C12N 15/82* (2006.01)

(52) U.S. Cl.
USPC ........... 800/282; 800/295; 800/296; 800/298; 435/419

(58) Field of Classification Search
None
See application file for complete search history.

(56) References Cited

PUBLICATIONS

Sudhamsu, J. et al. The Journal of Biological Chemistry (Nov. 21, 2008), vol. 283, No. 47; pp. 32968-32976.*
Komatsu, T. et al. The Plant Journal (2010) vol. 61 pp. 409-422.*
Asami et al., "Characterization of Brassinazole, a Triazole-Type Brassinosteroid Biosynthesis Inhibitor," *Plant Physiology* 123:93-99 (2000).
Hiraoka-Kanie et al., "Differentiation Stage-Specific Analysis of Gene Function with Inducible Short Hair-Pin RNA in Differentiating Embryonic Stem Cells," *Biochem. Biophys. Res. Commun.* 351(3):669-674 (2006).
Kattman et al., "Multipotent Flk-1+ Cardiovascular Progenitor Cells Give Rise to the Cardiomyocyte, Endothelial, and Vascular Smooth Muscle Lineages," Dev Cell. 11(5):723-732 (2006).
Komatsu et al., Summary of the 50th Annual Meeting of the Japanese Society of Plant Physiologists, published on Mar. 16, 2009 with English translation.
Komatsu et al., "The Chloroplast Protein BPG2 Functions in Brassinosteroid-Mediated Post-Transcriptional Accumulation of Chloroplast rRNA," The Plant Journal 61:409-422 (2010).
Kono et al, "Differentiation of Lymphatic Endothelial Cells From Embryonic Stem Cells on OP9 Stromal Cells," Arterioscler Thromb Vasc Biol. 26(9):2070-2076 (2006).
Kovacic et al., "Cardiovascular Regenerative Medicine: Digging in for the Long Haul," Cell Stem Cell 1(6):628-33 (2007).
Laflamme et al., "Regenerating the Heart," Nat. Biotechnol. 23(7):845-856 (2005).

Laflamme et al., "Cardiomyocytes Derived From Human Embryonic Stem Cells in Pro-Survival Factors Enhance Function of Infarcted Rat Hearts," Nat Biotechnol 25(9):1015-1024 (2007).
Moretti et al., "Multipotent Embryonic /s/1+ Progenitor Cells Lead to Cardiac, Smooth Muscle, and Endothelial Cell Diversification," Cell 127:1151-1165 (2006).
Mummery et al., "Differentiation of Human Embryonic Stem Cells to Cardiomyocytes: Role of Coculture with Visceral Endoderm-Like Cells," Circulation 107(21):2733-2740 (2003).
Nagata et al., "Treatment of Dark-Grown Arabidopsis Thaliana with a Brassinosteroid-Biosynthesis Inhibitor, Brassinazole, Induces Some Characteristics of Light-Grown Plants," Planta 211:781-790 (2000).
Nakagawa et al., "Generation of Induced Pluripotent Stem Cells Without Myc From Mouse and Human Fibroblasts," Nat. Biotechnol. 26(1):101-106 (2008).
Nelson et al., "CXCR41+/FLK-11+ Biomarkers Select a Cardiopoietic Lineage from Embryonic Stem Cells," Stem Cells 26(6):1464-1473 (2008).
Nishikawa et al., "Progressive Lineage Analysis by Cell Sorting and Culture Identifies FLK1+VE-cadherin+ Cells at a Diverging Point of Endothelial and Hemopoietic Lineages," Development 125(9):1747-1757 (1998).
Okita et al., "Generation of Germline-Competent Induced Pluripotent Stem Cells," Nature 448(7151):313-317 (2007).
Passier et al., "Increased Cardiomyocyte Differentiation From Human Embryonic Stem Cells in Serum-Free Cultures," Stem Cells 23(6):772-780 (2005).
Sone et al., "Pathway for Differentiation of Human Embryonic Stem Cells to Vascular Cell Components and Their Potential for Vascular Regeneration," Arterioscler. Thromb. Vasc. Biol. 27(10):2127-2134 (2007).
Tambara et al., "Transplanted Skeletal Myoblasts Can Fully Replace the Infarcted Myocardium When They Survive in the Host in Large Numbers," Circulation 108 [suppl II]: II259-II263 (2003).
Wu et al., "Developmental Origin of a Bipotential Myocardial and Smooth Muscle Cell Precursor in the Mammalian Heart," Cell 127(6):1137-1150 (2006).
Yamanaka, "Strategies and New Developments in the Generation of Patient-Specific Pluripotent Stem Cells," Cell Stem Cell 1(1):39-49 (2007).
Yamashita et al., "Flk1-Positive Cells Derived From Embryonic Stem Cells Serve as Vascular Progenitors," Nature 408(6808):92-96 (2000).
Yang et al., "Human Cardiovascular Progenitor Cells Develop From a KDR+ Embryonic-Stem-Cell-Derived Population," Nature 453(7194):524-528 (2008).
Yurugi-Kobayashi et al., "Adrenomedullin/Cyclic AMP Pathway Induces Notch Activation and Differentiation of Arterial Endothelial Cells From Vascular Progenitors," Arterioscler. Thromb. Vasc. Biol. 26(9):1977-1984 (2006).

* cited by examiner

*Primary Examiner* — Russell Kallis
(74) *Attorney, Agent, or Firm* — Clark & Elbing LLP

(57) ABSTRACT

This invention provides a transformed plant or alga with increased chlorophyll, comprising an overexpressed foreign DNA which codes for a chloroplast protein BPG2 or a homologue thereof, and a method for producing the transformed plant or alga.

23 Claims, 20 Drawing Sheets
(7 of 20 Drawing Sheet(s) Filed in Color)

```
BPG2.seq              1 --MVVLISSTVTICNVKPKLEDGNFRVSRLIHRPEVPFFSGLSNEKKKKCAVSVMCLAVK   58
V.vinifera1.seq       1 --------------------------------MRKNSRK-NDIKF----SFVALSVK    20
M.truncatula.seq      1 --MATLFS---TTALPSTNVTSKLSTLNNTSHSHALRHFSGN-TTKRFHKASSIAFAVK   54
O.sativa.seq          1 --MAKPLLLPATVAAAAAARLPSRLAVGAAPPFRVLPFFLCPPPPQSRS---LSFSPVSAV   55
At4g10620.seq         1 -------MLSKAARELSSSKLKPLFALHLSSFKSSIPTKPNPSPPSYLN-PHHFNNISKP   52
RIF1.seq              1 MALRTLSTFPSLPRRHTTTRREPNLTVIYRNPTTSIVCKSIANSEPPVSLSERDGFAAAA   60
YqeH-B.subtilis.seq   1 -----------------------------------------------------------    1

BPG2.seq             59 KEQVVQSVESVNGTIFPKKSKNLIMSEGRD--------EDEDYGKIICPGCGIFMQDNDP  110
V.vinifera1.seq      21 SKYTIQETQKNNWKNPRKVGGNPILSEGKD--------EDESYG-QICPGCGVYMQDEDP   71
M.truncatula.seq     55 NNPTIRKT------TPRRDSRNPLLSEGRD--------EDEALG-PICPGCGIFMQDNDP   99
O.sativa.seq         56 STAGKRGR-------SPPPPPSPVISEGRDD-------EDAAVGRPVCPGCGVFMQDADP  101
At4g10620.seq        53 PFLRFYSS-------SSSSNLLPLNRDGNYN-------DTTSITTSVCPGCGVHMQNSNP   98
RIF1.seq             61 PTPGERFLENQRAHEAQKVVKKEIKKEKKKKKEEIIARKVVDTSVSCGYGCQAPLQTSDV  120
YqeH-B.subtilis.seq   1 ----------------------------MEKVV------CHGCGVTIQTEDX          18

BPG2.seq            111 DLPGYYQK-RKVIANNLEGDEH-------------------VENDELAGFEMVDDDADE  149
V.vinifera1.seq      72 NLPGYYQK-RKLTLTEMPEG-----------------------QEDME-------GSDGEF  101
M.truncatula.seq    100 NLPGFYQQ-KEVKIETFSEEDY----------------ELDDE-------EDDGEE    131
O.sativa.seq        102 NLPGFFKNPSRLSDDEMGEDGSPPLAAEPDGFLGDDEEDGAPSESDLAAELDGLDSDLDE  161
At4g10620.seq        99 KHPGFFIK---------------------------------------------PSTI   110
RIF1.seq            121 DSPG--------------------------------------------------------  124
YqeH-B.subtilis.seq  19 TGLG--------------------------------------------------------   22

BPG2.seq            150 EEEGEDDEMDDEIKNAIEGSNSESESGFEESDEWEEKKEVN----DVELDGFAPAGVGY  205
V.vinifera1.seq     102 SNLG----------------TEDGNEFDDDSDEWESELEGE--DDDLDLDGFAPAGVGY  142
M.truncatula.seq    132 EDNG---------------SID-DESDDDSEELEAMLLGEENDDKVDLDGFTHAGVGY  173
O.sativa.seq        162 FLEEEFDENGEDGAFMKADTDAKIDGFSSDIDSD-WDEFMEDEEEEKWRKELDGFTPPGVGY  220
At4g10620.seq       111 KQRN---------------------------------------DLNLRDLTPISQEP  128
RIF1.seq            124 -----------------------------------------------------------  124
YqeH-B.subtilis.seq  22 -----------------------------------------------------------   22

BPG2.seq            206 GNVIEE---KEKKKRVSRIERKIAREEAAKDNY-DDVTVCARCHSLRNYGQVKNQAAEN  261
V.vinifera1.seq     143 GNITEE-TINKRKKRVSKSEKRHAREAEPER---EEVTVCARCHSLRNYGQVKNQM-AEN  199
M.truncatula.seq    174 GNVIEE-VLERAKKKVSKALEKRHAREAEKVK---EEVTVCARCHSLRNYGQVKNYKAEN  230
O.sativa.seq        221 GKITEL-TLERWKKEKLSKSEKSRRAREAKNAEAEEEDAAVVCARCHSLRNYGHVKNDKAEN  280
At4g10620.seq       129 -EFIDSIKRGFIIEPISSSDLNPRDDEPSDSR-----PLVCARCHSLRITGRVKDPTVEN  182
RIF1.seq            125 ---------FVDLVTYELKKKHHQLR--------TMIGRCQLLSHGHMITAVGGNG  164
YqeH-B.subtilis.seq  23 ------------YAPPAS--LTKEN---------VISQRCFRLKNTNEIQDVS---   52

BPG2.seq            262 LLP-DFDFDRLISTRLIKPMSNSSITVVVMVVDCVDFGSFPKRAAKSLFQVLQKAENDP  320
V.vinifera1.seq     200 LIP-DFDFDRLIATRLMKPTGTADAIVVVMVVDCVDFGSFPKRAAKSLFKALEGSRVGA  258
M.truncatula.seq    231 LLP-DFDFDRLITTRLMNPAGSGSSIVVVMVVDCVDFGSFPKRTAMKSLFKALEGMQENT  289
O.sativa.seq        281 LLP-DFDFDRFISSRLMK--RSAGTPVIVVMVADCVDFGSFPKRAAKSLFKAIEG--RGT  335
At4g10620.seq       183 LLP-DFDFDHTVGRLLGS--ASGARIVLMVVDASDFGSFPKRVARLVSRTIDENNMAW   239
RIF1.seq            165 GYPGGKQPVSADELNEKLSHLRHEKALIVKLVDIVDFLGSFLARVRDLVG---------  214
YqeH-B.subtilis.seq  53 --------LTDDDFLNTLHGTGETDSLVVKTVDIFDFNGSWTNGLQRLVG          94
```

Fig. 2 (Cont'd)

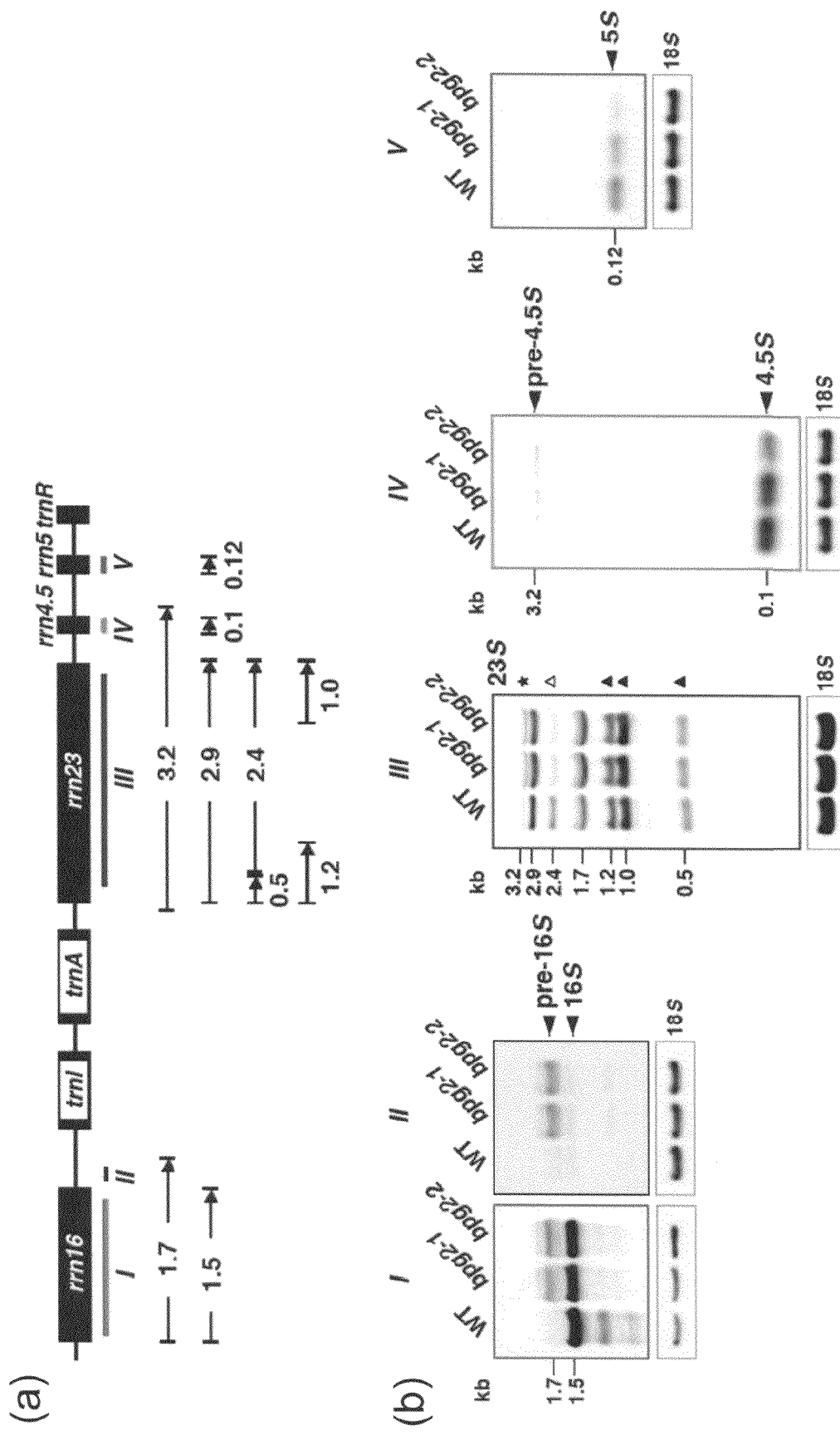

(a)

(b)

TRANSFORMED PLANTS OR ALGAE WITH HIGHLY EXPRESSED CHLOROPLAST PROTEIN BPG2

BACKGROUND OF THE INVENTION

1. Field of the Invention

This invention relates to transformed plants or algae with highly expressed chloroplast protein BPG2 (brassinazole-insensitive-pale green 2) or homologue thereof. The transformed plants or algae can produce higher levels of chlorophyll than wild type.

2. Background Art

Plant steroids, the brassinosteroids (BRs); brassinolide, castasterone, teasterone and so on, are essential for plant growth and development. The most active BR, brassinolide (BL), was first isolated from pollen of *Brassica napus* (Grove et al., 1979), and since then, more than 50 BRs have been isolated from other plant species (Bajguz and Tretyn, 2003). Molecular characterization of *Arabidopsis* BR biosynthetic mutants has revealed the important role of BRs in photomorphogenesis, leaf development, stem elongation, root elongation, pollen tube growth, xylem differentiation, sterility, and senescence.

deetiolated2 (det2) was first thought to be an abnormal photomorphogenesis mutant and was later identified as the first mutant deficient in BR biosynthesis (Chory et al., 1991). DET2 encodes a steroid 5α reductase involved in BR biosynthesis that can also catalyze mammalian steroid 5α reduction (Li et al., 1997; Fujioka et al., 1997). det2 has a dwarf phenotype with dark green round leaves and short inflorescences in the light, and a short hypocotyl and open cotyledons in the dark. In addition to these developmental characteristics, dark-grown det2 mutants also show increased expression of light-induced photosynthetic genes and their translated proteins encoded in the nuclear and chloroplast genomes. These results suggest that BR deficiency regulates chloroplast gene expression, as photosynthetic genes are normally not expressed in the dark. Based on the det2 phenotype, several BR-deficient mutants have been isolated, such as the BR biosynthesis mutants dwf4 (Azpiroz et al., 1998; Choe et al., 1998) and cpd (Szekeres et al., 1996) as well as BR-insensitive mutants such as the BR-signaling mutants bri1(Clouse et al., 1996; Li and Chory, 1997) and bin2 (Li et al., 2001; Li and Nam, 2002). These BR mutants generally show abnormal development in the light and de-etiolation in the dark. Previous characterization of the chloroplast in BR mutants has been limited, but it is important to further analyze the relationship between chloroplast development and BR.

Brz is a triazole compound that specifically inhibits BR biosynthesis by blocking the cytochrome P450 steroid C-22 hydoxylase encoded by DWF4/CYP90B1 (Asami et al., 2000, 2001). In the dark, Brz-treated *Arabidopsis* has open cotyledons and a short hypocotyl similar to BR-deficient mutants (Nagata et al., 2000). After growth in the dark for 40 days, plants treated with Brz develop true leaves with epidermal cells, guard cells, trichomes, palisade parenchyma cells, and spongy parenchyma cells. This phenotype in *Arabidopsis* can be rescued by addition of BR (Asami and Yoshida, 1999).

Recently, the mechanism of BR signal transduction in plant development has been analyzed in detail using chemical genetics to screen for mutants with altered responses to Brz in darkness at the germination stage. When grown in medium containing Brz, wild-type plants had short hypocotyls, but a mutant identified by the screen, Brz-insensitive-long hypocotyl1 (bil1-D) had a long hypocotyl in the dark (Asami et al., 2003). bil1-D has the same mutation as brassinazole-resistance 1-1D (bzr1-1D), and BZR1 encodes a functional transcription factor with dual roles in regulating BR biosynthesis genes and growth responses (Wang et al., 2002; He et al., 2005). BES1 was isolated from bri1-EMS-suppressor 1 (bes1-D), which is a semidominant suppressor of bri1. BES1 encodes a close homolog of BZR1/BIL1 but regulates BR response genes in plant development (Yin et al., 2002).

Here, we isolated and characterized a recessive *Arabidopsis* mutant, bpg2, which has pale green cotyledons and is insensitive to Brz-induced promotion of greening. BPG2 encodes a chloroplast protein that specifically regulates accumulation of 16S and 23S rRNA but not mRNA from the chloroplast genome. Brz-inducible protein accumulation in chloroplasts is suppressed by the bpg2 mutation. We have now found an important role of BPG2 in chloroplast development in BR signaling.

An object of this invention is to provide a method for producing a transformed plant or alga with increased chlorophyll.

Another object of this invention is to provide such transformed plant or alga.

SUMMARY OF THE INVENTION

In a first aspect, this invention provides a transformed plant or alga with increased chlorophyll, comprising an overexpressed foreign DNA which codes for a chloroplast protein BPG2, a homologue thereof, or a mutant thereof.

According to one embodiment of the invention, the BPG2, homologue or mutant comprises an amino acid sequence as shown in SEQ ID NO:1, or an amino acid sequence having an at least 20% identity to the amino acid sequence of SEQ ID NO:1 and having an activity of increasing a level of chlorophyll when compared with wild types.

According to another embodiment of the invention, said DNA comprises: (i) a nucleotide sequence as shown in SEQ ID NO:2, or a nucleotide sequence having an at least 20% identity to the nucleotide sequence of SEQ ID NO:2; (ii) a nucleotide sequence encoding the chloroplast protein BPG2 as defined in claim 2; or (iii) a nucleotide sequence capable of hybridizing with a nucleotide sequence complement to the nucleotide sequence of SEQ ID NO:2 under stringent conditions, wherein the nucleotide sequence (i), (ii) or (iii) codes for a protein having an activity of increasing a level of chlorophyll when compared with wild types.

According to further embodiment of the invention, the transformed plant or alga is further characterized by increased accumulation of RuBisCo small subunit protein or analog thereof which is a key protein for fixation of carbon dioxide in the photosynthesis.

According to further embodiment of the invention, the transformed plant or alga is further characterized by increased accumulation of protein D1 or analog thereof involved in the photosystem II of photosynthesis.

According to further embodiment of the invention, the transformed plant or alga is further characterized by increased accumulation of a light harvesting complex chlorophyll binding protein.

According to further embodiment of the invention, the transformed plant or alga is further characterized by increased activity of photosynthesis in the presence of light and brassinazole.

In a second aspect, this invention further provides progeny of the above-defined transformed plant or alga.

In a third aspect, this invention further provides a cell, tissue, organ, or seed from the transformed plant or alga as defined above.

In a fourth aspect, this invention further provides a method for producing the transformed plant as defined above, comprising the following steps of:
(1) introducing a vector comprising the DNA as defined above into cells of a plant to obtain transformed cells;
(2) selecting a transformed cell, which overexpresses the DNA, from the transformed cells of step (1); and
(3) generating the transformed plant from the transformed cell of step (2).

In a fifth aspect, this invention further provides a method for producing a transformed alga as defined above, comprising introducing a vector comprising the DNA as defined above into cells of an alga to obtain transformed cells, and selecting a transformed cell overexpressing the DNA, from the obtained transformed cells.

BRIEF DESCRIPTION OF THE DRAWINGS

The application file contains drawings executed in color. Copies of this patent or patent application with color drawings will be provided by the Office upon request and payment of the necessary fee.

Nuclear encoded mRNAs or proteins shown in blue, chloroplast-encoded mRNAs or proteins shown in dark green, BPG2 and BPG2 shown light green and chloroplast rRNA shown in red. In wild type plants (left), BPG2 mRNA was transcribed normally and translated to protein. Normal functioning of BPG2 in chloroplast rRNA processing allowed the normal translation of chloroplast protein. Brz treatment increased expression of chloroplast genes, resulting in accumulation of chloroplast proteins. In bpg2 mutant (right), BPG2 mRNA was not transcribed and plants showed abnormal chloroplast rRNA processing. Chloroplast genes were normally expressed and Brz enhanced this expression, but the translation of chloroplast-encoded proteins was suppressed and accumulation was reduced. Finally, the bpg2 mutant showed a pale green phenotype. These results show that the BPG2 protein plays an important role in chloroplast biogenesis and chloroplast protein synthesis by regulating chloroplast rRNA under the control of brassinosteroid signal transduction.

Figure 13:
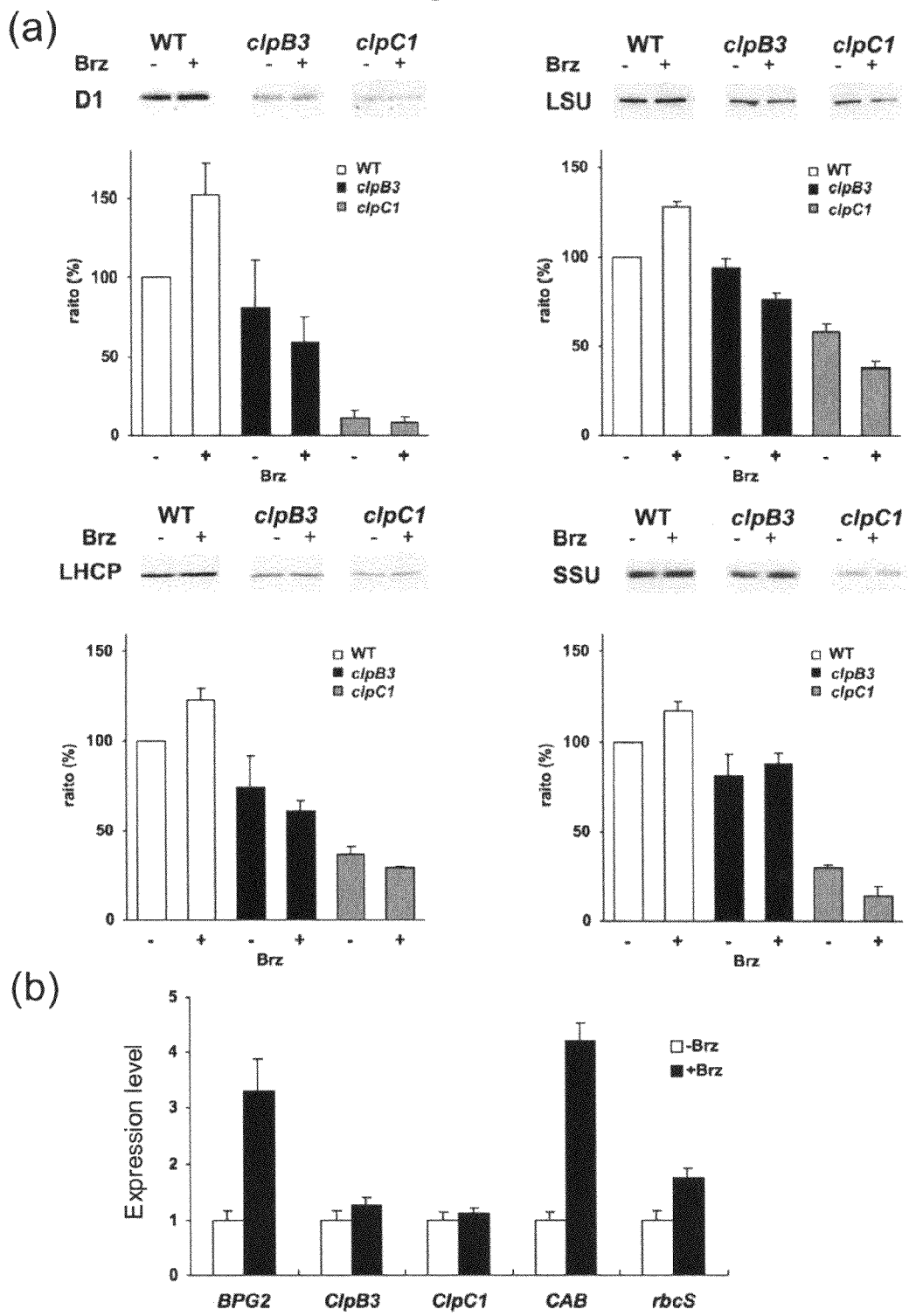

FIG. 13. (a) Accumulation of chloroplast proteins was not increased by Brz in clp mutant. Total protein was prepared from wild type (WT), clpB3 and clpC1 germinated in the light for 3 days with 0 or 1 μM Brz. Immunoblot analyses were performed using polyclonal antibodies against photosystem II D1 protein, LHCP protein and Rubisco LSU and SSU. Error bar indicates SE. (b) BPG2 mRNA was highly induced by Brz in comparison with CLP mRNAs. RT-PCR analysis of expression of BPG2, ClpB3, ClpC1, CAB and rbcS grown on Brz. Total RNA was extracted from wild type plants germinated in the dark for 7 days with Brz (1 μM) and without Brz. RT-PCR and quantification of products were performed by Thermal Cycler Dice Real Time System TP800 (Takara). Sequences of gene-specific primers for RT-PCR were CLPB3, 5'-TGCTTGGGTTGCTACGTGAA-3' (SEQ ID NO:3) and 5'-ACCCACCATGCGTATCACCT-3' (SEQ ID NO:4); CLPC1, 5'-TCCGGAAGGCAAGTATGAGG-3' (SEQ ID NO:5) and 5'-TGCATCTTCGGATCTCGTCA-3'. (SEQ ID NO:6).

Figure 14:
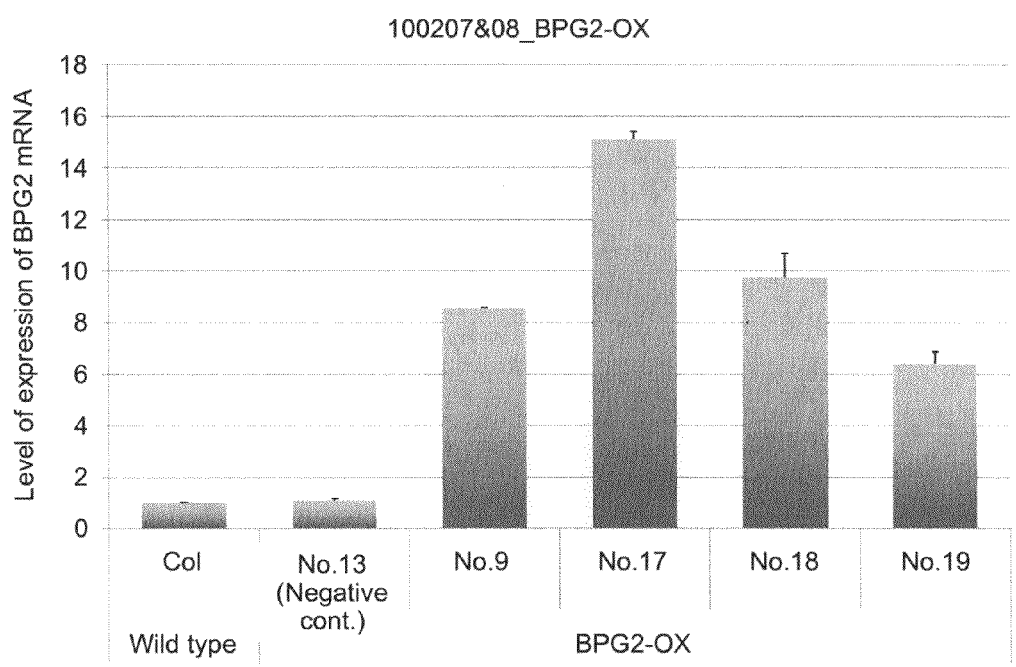

FIG. 14. Selection for BPG2 mRNA higher expression transformed lines by real time PCR. BPG2-OX lines Nos. 9, 17, 18 and 19 highly expressed BPG2 as compared with the wild type (Col) and the negative control No. 13.

Figure 15:
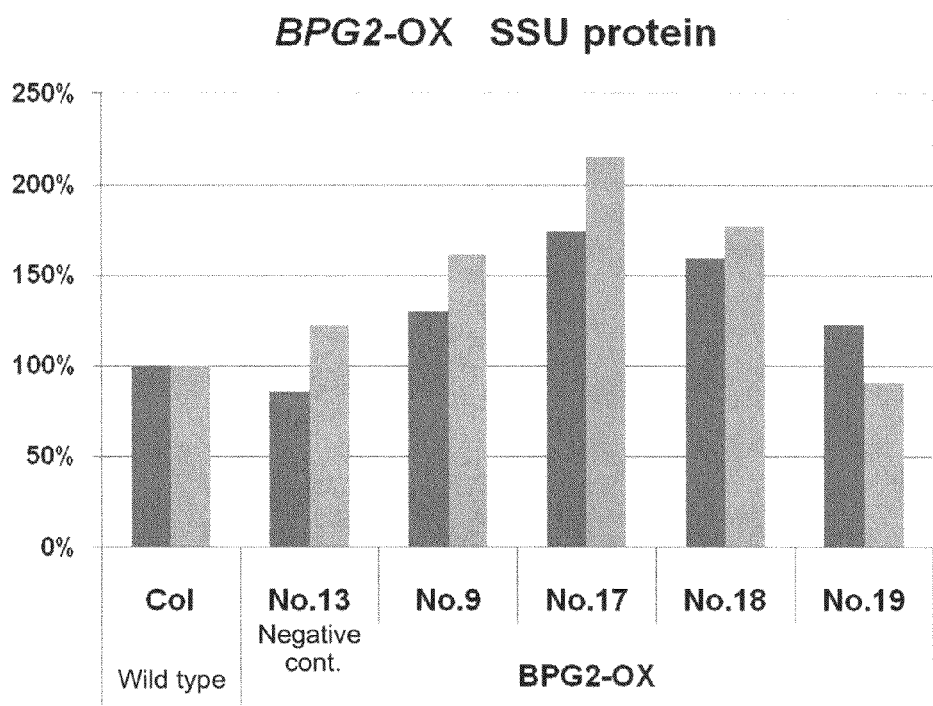

FIG. 15. High accumulation of RuBisCo small subunit protein in BPG2 overexpressors (BPG2-OXs). Analysis was carried out by Western bolt. BPG2 highly expressing transformed lines Nos. 9, 17, 18 and 19 highly accumulated RuBisCo S ('SSU') protein as compared with the wild type (Col) and the negative control No. 13. In each line, left bar shows relative amount of RuBisCo small subunit protein level of the $1^{st}$ experiment, and right bar shows the $2^{nd}$ experiment.

Figure 16:
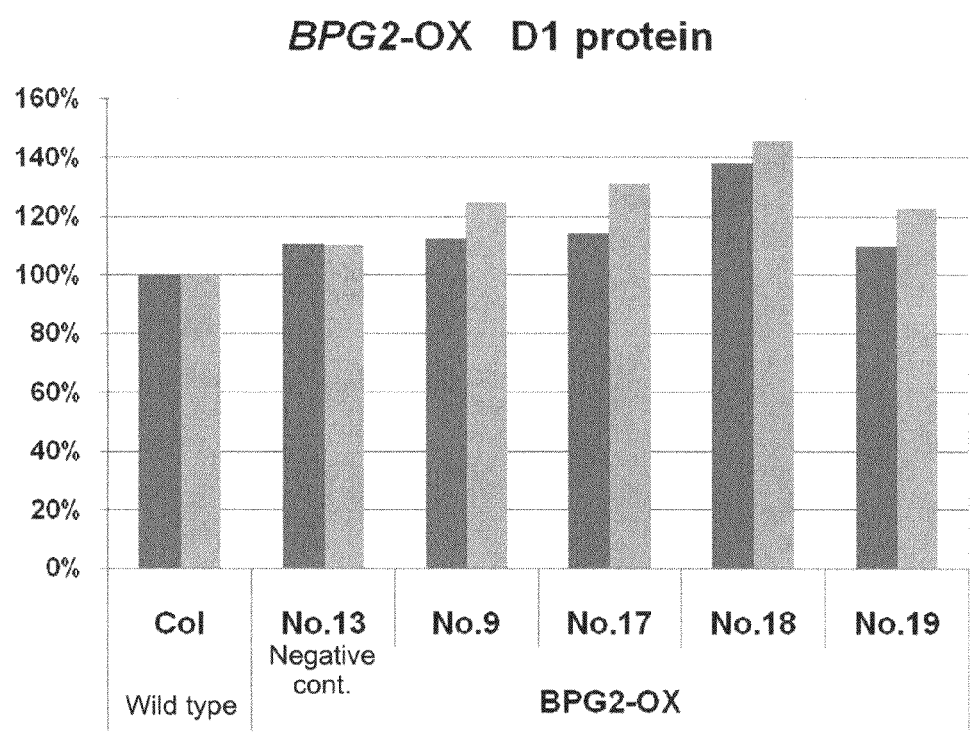

FIG. 16. High accumulation of D1 protein in BPG2 overexpressors (BPG2-OXs). Analysis was carried out by Western bolt. BPG2 highly expressing transformed lines Nos. 9, 17, 18 and 19 highly accumulated D1 protein as compared with the wild type (Col) and the negative control No. 13. In each line, left bar shows relative amount of D1 protein level of the $1^{st}$ experiment, and right bar shows the $2^{nd}$ experiment.

Figure 17:
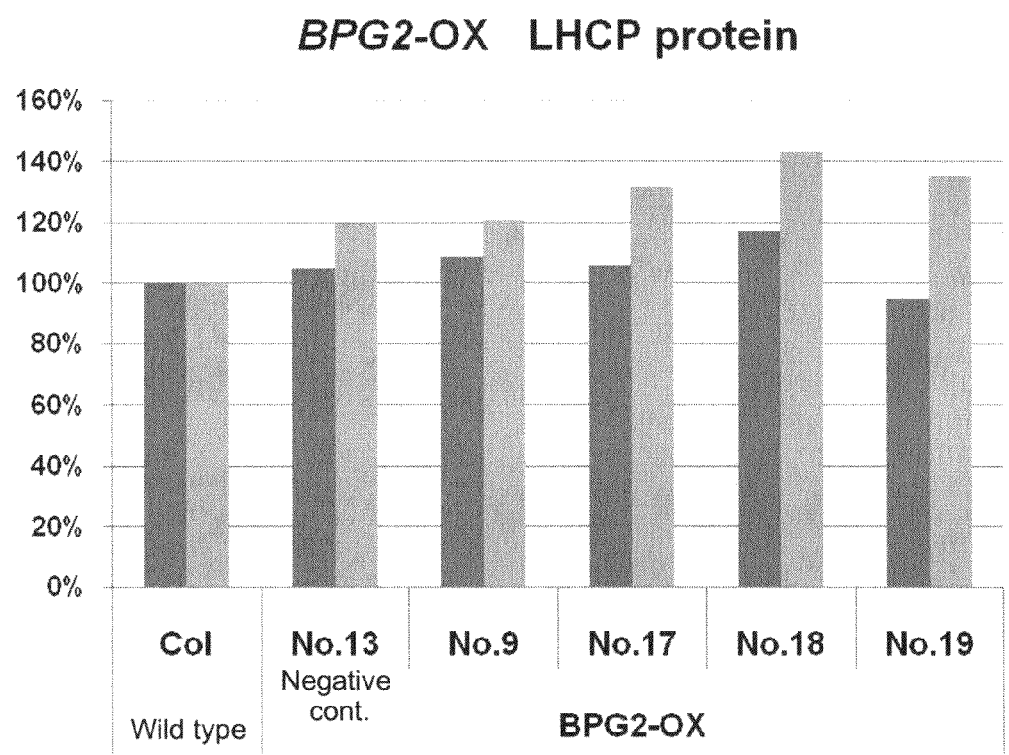

FIG. 17. High accumulation of light harvesting complex chlorophyll a/b binding protein in BPG2 overexpressors (BPG2-OXs). Analysis was carried out by Western bolt. BPG2 highly expressing transformed lines Nos. 9, 17, 18 and 19 highly accumulated D1 protein as compared with the wild type (Col) and the negative control No. 13. Relative amounts of light harvesting complex chlorophyll a/b binding protein level of the $1^{st}$ experiment are depicted in this figure, and right bar shows the $2^{nd}$ experiment.

DETAILED DESCRIPTION OF THE INVENTION

This invention will be described in more detail below.
Transformed Plants and Algae The transformed plants or algae of the invention are characterized by increased chlorophyll, the level of which is higher than that of wild types. This character of the plants or algae is achieved by overexpressing a foreign (or exogenous) DNA coding for a chloroplast protein BPG2 or a homologue thereof in the plants or algae.

As used herein, the term "overexpressing", "overexpressed" or "overexpression" means that an expression level of the BPG2 protein or homologue thereof in the transformed plants or algae of the invention is higher than that in wild types which has no foreign BPG2 or homologue.

As used herein, the term "BPG2" is an abbreviation of brassinazole-insensitive-pale green 2, and BPG2 is a chloroplast protein that specifically regulates accumulation of 16S and 23S rRNAs but not mRNA from the chloroplast genomes. We have now found that BPG2 has an important role in increase of chlorophyll in plants or algae, resulting in elevating the ability of the photosynthesis.

As used herein, the term "foreign" means that BPG2 protein or homologue thereof is not endogenous. In other words, the BPG2 or homologue coding DNA is introduced exogenously into plants or algae.

As used herein, the term "homologue" means a protein from any plants or algae other than *Arabidopsis thaliana*, which protein comprises an amino acid sequence homologous to that of BPG2 protein and has more increased chlorophyll than wild type.

In this invention, the BPG2 or homologues thereof may be mutated as long as the mutants have more increased chlorophyll than wild type when they are expressed in plants or algae.

In this invention, the plants or algae include all organisms having an ability to produce chlorophyll, i.e. an ability of the photosynthesis.

Examples of such plants and algae include, but are not limited to, dicotyledonous plants, monocotyledonous plants, tree plants, green algae, Bacillariophyceae, phototrophic bacteria, blue green algae (cyanobacteria), Phaeophyceae, Rhodophyta, etc.

Specifically, examples of plants include Brassicacea, Gramineae, Leguminosae, Solanaceae, Fagaceae, Liliaceae, Chenopodiaceae, Myrtaceae, Salicaceae, Category, etc., and more specifically, *Arabidopsis thaliana*, *Brassica napus*, *Brassica oleracea* var. italica, *Raphanus sativus* L., *Brassica oleraceae* var. botrytis, *Brassica oleracea* var. capitata, *Brassica rapa* var. glabra, *Oryza sativa*, *Triticum aestivum*, *Hordeum vulgare*, *Zea mays*, *Glycine max*, *Lotus corniculatus* var. japonicus, *Solanum lycopersicum*, *Solanum melongena*, *Solanum tuberosum* L., *Allium fistulosum*, *Allium cepa*, *Allium sativum*, *Spinacia oleracea*, *Saccharum officinarum*, *Eucalyptus*, *Populus*, *Elaeis gunineensis*, *Wasabia japonica*, *Allium tuberosum*, etc.

Examples of algae include Spirogyra, Microcystis, Chlamydomonadales, Volvocales, Chlorococcales, Microsporales, Cylindrocapsales, Sphaeropleales, Chaetophorales, Chaetopeltidale, Cedogoniales, Chrorella, Aulacoseira, Chlamydomonas, Melosira, Cyclotella, Prorocentrum, Alexandrium, Navicula, Skeletonema, Chaetoceros, Pseudo-nitzschia, Thalassiosira, Dunaliella, Eisenia, Laminaria, Undaria, Ulva, Gelidium, Chondrus, Eucheuma, etc.

As used herein, the term "chlorophyll" means one or more chlorophylls selected from the group consisting of all photosynthesis-associated chlorophylls such as chlorophyll a, chlorophyll b, chlorophyll c, and chlorophyll d.

The transformed plants or algae of the invention are also characterized by increased accumulation of the RuBisCo small subunit protein or analog thereof which is a key protein for fixation of carbon dioxide in the photosynthesis. The RuBisCo small subunit protein occupies approximately 50% of total proteins in green leaf, and its gene is encoded on the nucleic genome.

The transformed plants or algae of the invention are further characterized by increased accumulation of protein D1 or analog thereof involved in the photosystem II of photosynthesis. The D1 protein is a key protein in the photochemical reaction by which energy for photosynthesis is made on thylakoid membranes, and its gene is encoded on the genome of chloroplast.

The transformed plants or algae of the invention are further characterized by increased accumulation of a light harvesting complex chlorophyll binding protein, which is a key protein binding to chlorophyll (e.g., chlorophyll a/b) that absorbs the light on thylakoid membranes, and its gene is encoded on the nucleic genome.

The transformed plants or algae of the invention are further characterized by increased activity of photosynthesis in the presence of light and brassinazole. Brassinazole is a specific inhibitor of the biosynthesis of brassinosteroids, which regulate plant organ and chloroplast development. In wild type, chloroplast proteins are increased by brassinazole, while in the transformed plants or algae of the invention, further accumulation of chloroplast proteins occurs by overexpression of BPG2 or homologues in the presence of light and brassinazole.

The "analog" as described above is a protein having a function analogous to the known native biological function of the RuBisCo small subunit protein or D1 protein.

In this invention, progeny of the transformed plants or algae is also encompassed. Progeny includes second generation, third generation, and further subsequent generations. The progeny may generally be generated by callus culture, or alternatively by crossing the transformed plant with wild type. The progeny of the invention is characterized by increased chlorophyll as compared with wild type.

BPG2 And Homologues

The amino acid and nucleotide sequences of BPG2 or homologue proteins and DNAs encoding them are available from known databases such as NCBI GenBank (USA), EMBL (Europe), etc. For example, GenBank accession numbers of BPG2 and homologues are: *Arabidopsis thaliana*, NM 117139 (At4g10620), NM_114613 (At3g47450); *O. sativa*1, CM000143; *O. sativa*2, NM_001064237; *V. vinifera*1, CU459251; *V. vinifera*2, CU459220; *M. truncatula*, AC158502; *P. patens*, XM_001758456; *Ostreococcus lucimarinus*, XM_001418245; *Chlamydomonas reinhardtii*, XM_001700742; *Listeria monocytogenes*, NC_003210; *Exiguobacterium sibiricum*, NC_010556; *Lactobacillus casei*, NC_008526; *Enterococcus faecium*, NZ_AAAK03000016; *Lactococcus lactis*, NC_009004; *Streptococcus sanguinis*, NC_009009; *Geobacillus thermodenitrificans*, NC_009328; *Lysinibacillus sphaericus*, NC_010382; *Staphylococcus haemolyticus*, NC_007168; *Oceanobacillus iheyensis*, NP_692909; *Bacillus subtilis*, Z99117.

Specifically, BPG2 or homologue proteins or mutant proteins thereof comprise an amino acid sequence as shown in SEQ ID NO:1, or amino acid sequences having an at least 20%, preferably at least 50%, more preferably at least 70-85%, yet more preferably at least 90-98% identity to the amino acid sequence of SEQ ID NO:1 and having an activity of increasing a level of chlorophyll when compared with wild types.

The DNAs encoding BPG2, homologue proteins, or mutant proteins comprise: (i) a nucleotide sequence as shown in SEQ ID NO:2, or nucleotide sequences having an at least 20%, preferably at least 50%, more preferably at least 70-85%, yet more preferably at least 90-98% identity to the nucleotide sequence of SEQ ID NO:2; (ii) nucleotide sequences encoding the BPG2 protein as defined above; or (iii) nucleotide sequences capable of hybridizing with a nucleotide sequence complement to the nucleotide sequence of SEQ ID NO:2 under stringent conditions, wherein the nucleotide sequences (i), (ii) and (iii) code for proteins having an activity of increasing a level of chlorophyll when compared with wild types.

The level of chlorophyll can be determined at 645 nm and 663 nm optically for supernatants of homogenized organisms (Arnon (1949)).

As used herein, the term "mutant" comprises one or more, preferably one or several, deletions, substitutions or additions in the amino acid or nucleotide sequences of BPG2 or homologues thereof. The term "several" as used herein refers to an integer between 2 and 20, inclusive. The mutant may include either naturally occurring mutants or artificial mutants.

Where the mutant is a protein or polypeptide, preferable substitutions are conservative substitutions, which are substitutions between amino acids similar in properties such as structural, electric, polar, or hydrophobic properties. For example, the substitution can be conducted between basic amino acids (e.g., Lys, Arg, and His), or between acidic amino acids (e.g., Asp and Glu), or between amino acids having non-charged polar side chains (e.g., Gly, Asn, Gln, Ser, Thr, Tyr, and Cys), or between amino acids having hydrophobic side chains (e.g., Ala, Val, Leu, Ile, Pro, Phe, and Met), or between amino acids having branched side chains (e.g., Thr, Val, Leu, and Ile), or between amino acids having aromatic side chains (e.g., Tyr, Trp, Phe, and His).

Where the mutant is a nucleic acid, the DNA encoding a mutant protein of BPG2 or homologue thereof may comprise a nucleotide sequence capable of hybridizing to a complement sequence of the nucleotide sequence encoding BPG2 or homologue thereof as defined above, under stringent conditions. As used herein, the stringent conditions include low, medium or high stringent conditions. An example of the stringent conditions includes hybridization at approximately 42-55° C. in approximately 2-6×SSC, followed by wash at approximately 50-65° C. in approximately 0.1-1×SSC containing approximately 0.1-0.2% SDS, where 1×SSC is a solution containing 0.15 M NaCl and 0.015 M Na citrate, pH 7.0. Wash can be performed once or more. In general, stringent conditions may be set at a temperature approximately 5° C. lower than a melting temperature (Tm) of a specific nucleotide sequence at defined ionic strength and pH.

Mutants can be prepared using known techniques such as site-directed mutagenesis and PCR.

Also, DNAs encoding BPG2 or homologues thereof may be prepared and amplified from genomic or cDNA libraries derived from organs or tissues of a plant or alga, by using known cloning and PCR techniques. Organs include, but are not limited to, roots, stems, leaves, petals, seeds, etc., and tissues include, but are not limited to, epidermis, phloem, parenchyma, xylem, vascular bundle, palisade tissues, spongy tissues, etc.

These techniques are described in Sambrook et al., Molecular Cloning A Laboratory Manual, 1989, Cold Spring Harbor Laboratory Press, Ausubel et al., Current Protocols in Molecular Biology, 1994, John Wiley & Sons, etc.

Transformation

The transformed plants or algae of the invention can be prepared by transforming the cells of plants or algae with a vector comprising a DNA encoding BPG2 protein or homologue thereof, which DNA is as defined above.

The transformed alga can be produced by a method comprising introducing a vector comprising the DNA as defined above into cells of an alga to obtain transformed cells, and selecting a transformed cell overexpressing the DNA, from the obtained transformed cells.

The transformed plant can be produced by a method comprising the following steps of:
  (1) introducing a vector comprising the DNA as defined above into cells of a plant to obtain transformed cells;
  (2) selecting a transformed cell, which overexpresses the DNA, from the transformed cells of step (1); and
  (3) generating the transformed plant from the transformed cell of step (2).

For transformation of plants and algae, basically the same or similar methods can be used. For example, transformation can be performed by methods of using viral vectors (e.g., binary bector-Agrobacterium system), particle gun, electroporation, floral dip (Clough and Bent, Plant J. 16: 735-743 (1998)), leaf disc, and the like.

In general, vectors usable for transformation of plants or algae are binary vectors. The binary vector comprises two approximately 25-bp border sequences, i.e. right border (RB) and left border (LB) derived from Agrobacterium T-DNA. A foreign DNA can be inserted between the two border sequences, and a promoter is linked to the 5'-end of the foreign DNA.

Examples of the promoter include, but are not limited to, cauliflower mosaic virus (CaMV) 35S promoter (Jefferson, R. A. et al.: The EMBO J 6:3901-3907 (1987)]), noparin synthase gene promoter (Christensen, A. H. et al.: Plant Mol. Biol. 18:675-689 (1992)), ubiquitin corn promoter, octopin synthase gene promoter, rice actin promoter, and the like. Other promoters include rd29Agene promoter, rd29B gene promoter, rd17 gene promoter, rd22 gene promoter, cor6.6 gene promoter, cor15a gene promoter, erd1 gene promoter, kin1 gene promoter, etc (JP-2008-505603A).

In the vectors, a terminator may be linked to the 3'-end of the foreign DNA. Examples of the terminator include, but are not limited to, noparin synthase gene terminator, cauliflower mosaic virus derived terminator, and the like.

The vectors may contain a selectable marker or reporter gene necessary for screening transformed cells of interest. Examples of the selectable marker include, but are not limited to, drug resistant genes such as kanamycin resistant gene (NPTII), hygromycin resistant gene (htp), biarafos resistant gene, carbenicillin resistant gene, and the like. Examples of the reporter gene include, but are not limited to, GFP (green fluorescence protein) gene, GUS (β-glucuronidase) gene, luciferase gene, and β-galactosidase gene.

Examples of binary vectors include, but are not limited to, pBI plasmids such as pBI101, pBI101.2, pBI101.3, pBI121, pBI221, pBE2113Not, pBI2113Not, pBI2113, pGA482, pGAH, pBIG, etc., and other plasmids such as pLGV23Neo, pNCAT, pMON200, pH35GS containing GATEWAY (Kubo ら, 2005. Genes & Dev. 19: 1855-1860), etc.

When the binary vector-Agrobacterium system is used, the method comprises: providing cells, calli, or tissues from a plant or alga; and infecting them with Agrobacterium containing binary vector, thereby introducing the above-defined DNA into the cells of a plant.

Normally used as Agrobacterium are Agrobacterium tumefaciens strains, such as C58, LBA4404, EHA101, EHA105, C58C1RifR, etc.

Media for transformation are MS medium, B5 medium, DKN medium, Linsmaier & Skoog medium, etc. In general, to these basal media may be added 1-5% succaride such as maltose, sucrose, glucose, or sorbitol, and a solidification agent consisting of 0.2-1% polysuccaride such as agar or gellan gum. Media may further contain auxins or cytokinins, such as casamino acid, abscisic acid, kinetin, 2,4-D, or indole acetic acid; antibiotics such as kanamycin, hygromycin, or carbenicillin; acetosyringone, sinapinic acid, or hydroxycinnamic acid; or mixtures thereof. Acetosylingone, which is a phenolic compound, can be used effectively for transformation of monocotyledonous plants. Preferred pH of the medium is pH 5-6.

In transformation with the binary vector-Agrobacterium system, Agrobacterium is cultured at approximately 25° C. for about 4 days in the dark, and then plant callus or tissue (e.g., leaf piece, root, stem piece, or growing point) is dipped in the culture medium of Agrobacterium for several minutes, and after removal of water, the callus or tissue is co-cultured with Agrobacterium on a solid medium. The transformed callus or tissue can be selected for selectable marker (e.g., by culturing them in a medium containing antibiotic) or reporter (e.g., by detecting a fluorescence). The callus can redifferentiate into seedlings on a redifferentiation medium. The tissue may be transformed directly, or alternatively protoplasts may be prepared from the tissue, followed by induction of calli, which are subsequently redifferentiated into seedlings. After the roots are developed, the seedlings are transferred to soil for reproduction of plant. From the reproduced plant, seeds are collected in order to obtain transformed plants (or transgenic plants).

Transformation of algae can also be carried out by using the above-described binary vector-Agrobacterium system comprising co-culture of an alga (cells or tissue pieces) and Agrobacterium. Medium may contain a nitrogen source, a phosphate source, Mg, Si, K, Na, Ca, vitamins, minor metals, phenolic compounds (e.g., acetosylingone, sinapinic acid, or hydroxycinnamic acid), etc. in sea water and/or SW II medium or f/2 medium. Culture can be performed at 25-32° C. for 2-3 days or more (JP 2007-043926A). Transformed algae can be selected for selectable marker or reporter in the same manner as above.

Furthermore, progeny can be obtained from the transformed plants or algae. The progeny with increased chlorophyll also falls within the scope of the invention.

Host plants and algae for use in transformation are as described above, and thus they include all organisms having an ability to produce chlorophyll, i.e. an ability of the photosynthesis.

EXAMPLES

Experimental Procedures

Plant Material and Growth Conditions

*Arabidopsis thaliana* Columbia-0 (Col-0) was used as the wild type. For cotyledon analysis, plants were germinated and grown on ½ MS medium (Duchefa) containing 1.5% sucrose and 0.9% phytoagar (Duchefa), with or without Brz. Germinated plants were transferred to soil. Conditions in the growth chamber were 16 h light (100 µE $m^{-2}$ $sec^{-1}$ white light)/8 h dark at 22° C.

Measurement of Chlorophyll a and b

Chlorophyll was extracted from 3-day-old seedlings grown in the light (100 µm$^{-2}$ sec$^{1}$) under long days (16 h light/8 h dark). Plants were homogenized in 80% (v/v) acetone. The chlorophyll content of the centrifuged supernatants was determined at 645 nm and 663 nm. Chlorophyll a and b content were determined according to Arnon (1949):

Chlorophyll a (µg/mg fresh weight)=$(12.7A_{663}-2.59A_{645})$/mg fresh weight

Chlorophyll b (µg/mg fresh weight)=$(22.9A_{645}-4.67A_{663})$/mg fresh weight

TAIL-PCR

To identify the flanking genomic sequence of the T-DNA of pPCVICEn4HPT, we performed thermal asymmetric interlaced PCR (TAIL-PCR) as described (Liu et al., 1995). Genomic DNA was extracted from 3-week-old *Arabidopsis* rosette leaves using nucleon PHYTOpure PLANT DNA extraction (Amersham). The T-DNA flanking sequence was amplified using the T-DNA-specific primers LB150 5'-CACGTCGAAATAAAGATTTCCG-3' (SEQ ID NO:7) for the TAIL1 reaction, LB100 5'-CCTATAAATACGACGGATGC-3' (SEQ ID NO:8) for the TAIL2 reaction, and LB50 5'-ATAATAACGCTGCGGACATCT-3' (SEQ ID NO:9) for the TAIL3 reaction, and degenerate primers AD2 5'-NGTCGASWGANAWGAA-3' (SEQ ID NO:10) or AD5 5'-SSTGGSTANATWATWCT-3' (SEQ ID NO:10) (where S=G or C, W=A or T, N=A, G, C or T) for all three reactions.

Generation of BPG2-GFP Transformed Plants

The BPG2 cDNA expected stop codon was amplified from wild-type Col-0 cDNA by RT-PCR using KOD-plus-DNA polymerase (Toyobo). The PCR product was cloned into the pENTR®/-TOPO™ vector using the pENT™ Directional TOPO® Cloning Kit (Invitrogen). Site-directed mutagenesis for BPG2 was performed as described (Higuchi et al., 1988) and PCR products of mutated-BPG2s were cloned into the pENTR®/D-TOPO™ vector. Using Gateway technology (Invitrogen), the resulting pENTR-BPG2 and pENTR-mutated BPG2s were further cloned into the binary vector pGWB5 (Nakagawa et al., 2007) that contains a CaMV 35S promoter. The generated constructs 35S::BPG2-GFP and 35S::mutated-BPG2-GFP were transformed into wild-type Col-0, bpg2-1, or bpg2-2 by Agrobacterium-mediated floral dip method. Transformed plants were screened on ½ MS agar plates containing 25 µg ml$^{-1}$ kanamycin.

RT-PCR

Total RNA was extracted from wild type and bpg2 mutants with the RNeasy Plant mini kit (Qiagen). First strand cDNA was synthesized with Super Script III first-strand cDNA synthesis for RT (Invitrogen) and used as template. RT-PCR was performed with Ex Taq (Takara Bio). Sequences of gene-specific primers for RT-PCR were BPG2, 5'-AAGGGCCATTCCGGTTTAC-3' (SEQ ID NO:12) and 5'-TCCCAGCTATTTCCCGACAC-3' (SEQ ID NO:13), or 5'-CCTAGATGCAATGAAACACTAT-3' (SEQ ID NO:14) and 5'-GGCGGAATATTGTCTGCAAAG-3' (SEQ ID NO:15); CAB, 5'-GCCGCCTCAACAATGG-3' (SEQ ID NO:16) and 5'-ATGGCCAAAATGCTCTGAGC-3' (SEQ ID NO:17); rbcS, 5'-ACTTCCTTCAACACTTGAGC-3' (SEQ ID NO:18) and 5'-ATTGGCTAAGGAAGTTGACTAC-3' (SEQ ID NO:19), DWF4, 5'-TTCTTGGTCAAACCATCGGTTATCTTAAA-3' (SEQ ID NO:20) and 5'-TATGATAAGCAGTTCCTGGTAGATTT-3' (SEQ ID NO:21); GFP-specific primer, 5'-CACGTCGCCGTCCAGCTC-3' (SEQ ID NO:22). For the control, Actin2-specific primers were 5'-GTGAAGGCTGGATTTGCAGGA-3' (SEQ ID NO:23) and 5'-AACCACCGATCCAGGCACTGT-3' (SEQ ID NO:24).

Northern Blot Analysis

Total RNA was extracted from light grown 4-day-old seedlings, 3-week-old rosette leaves and dark grown 5-day-old seedlings of wild type, bpg2-1 and bpg2-2 with the RNeasy Plant Mini kit (Qiagen). Total RNA (3 µg) was separated in 1.2% agarose/0.66 M formaldehyde gels and blotted on Hybond N$^+$ (Amersham). After transfer, the ECL Direct Nucleic Acid Labeling and Detection system (GE Healthcare) was used for hybridization, and LAS-4000 mini (Fuji Film) was used for analysis of chemical fluorescence.

Immunoblot Analysis of Chloroplast Proteins

Light grown four-day-old seedlings and 3-week-old rosette leaves of wild type, bpg2-1, and bpg2-2 were ground in liquid nitrogen and extracted by boiling with two volumes/fresh weight of 1× Laemmli buffer [50 mM Tris-HCl (pH 6.8), 100 mM DTT, 2% (w/v) SDS, 0.1% (w/v) bromophenol blue, and 10% (w/v) glycerol] for immunoblot analysis of Rubisco LSU, SSU, and LHCP. Total proteins for immunoblot analysis of D1 protein were prepared as described (Nakajima et al., 1996). Proteins were separated by SDS-PAGE (12.5% acrylamide separating gel). After electrophoresis, the proteins were stained with Coomassie Brilliant Blue or electrophoretically transferred to Hybond ECL nitrocellulose membrane (Amersham). After blocking overnight in TBS (20 mM Tris, 0.137 M NaCl, pH7.4, 0.05% polyoxyethlene sorbital monolaurate) buffer containing 5% non-fat milk (Morinagamilk) at room temperature, the membrane was incubated in TBS buffer containing non-fat milk with polyclonal antibody for 1 h at room temperature. After washing in TBS buffer, the blots were incubated with horseradish peroxidase-conjugated secondary antibody (Promega for Rubisco L/S and LHCP, and Cosmo Bio for D1) for 1 h at room temperature, and the complexes were made visible with ECL Immoblin Western (Millipore). The polyclonal antibody against the tobacco Rubisco L/S complex was provided by F. Sato of Kyoto University. The polyclonal antibody against D1 and LHCP protein was obtained from Agrisera. LAS-4000 mini (Fuji Film) was used for detection.

Confocal Laser Scanning Microscopy

Rosette leaves were observed under confocal laser scanning microscope (LSM510, Zeiss, Germany). The samples were dissected, mounted on a glass slide, and excited by 488 nm Argon laser (11%) and 633 nm HeNe laser (11%). Images were acquired with 505-550 nm (for green channel; GFP) and 668-743 nm (for red channel; chloroplast autofluorescence) emission filter sets.

Electron Microscopy

Rosette leaf segments of 3-week-old plants grown on soil under long-day conditions, were fixed with glutaraldehyde, postfixed osmium tetrooxide. Samples were then dehydrated, embedded in Spurr's resin, sectioned (90 nm) and stained with uranyl acetate and lead citrate. Stained sections were observed under transmission electron microscope (JEM1200EX, JEOL, Japan).

Quantitative Real Time PCR

Total RNA was extracted from wild-type plants with an RNeasy Plant Mini Kit (Qiagen). First-strand cDNA was synthesized with PrimeScript (Takara) and used as the RT-PCR template. Quantitative real time-PCR was performed according to the instructions provided for the Thermal Cycler Dice (Takara) with the SYBR Premix ExTaq system (Takara). Sequences of gene-specific primers for RT-PCR were: BIL4: 5'-CGCCTCTCTACCCGATGATG-3' (SEQ ID NO:25) and 5'-GCAGCGACGGCGATTGTA-3' (SEQ ID NO:26) and for the constitutively expressed control gene ACT2: 5'-CGC-CATCCAAGCTGTTCTC-3' (SEQ ID NO:27) and 5'-TCACGTCCAGCAAGGTCAAG-3' (SEQ ID NO:28). Sequences of gene-specific primers for RT-PCR were BPG2, 5'-AAGGGCCATTCCGGTTTAC-3' (SEQ ID NO:29) and 5'-TCCCAGCTATTTCCCGACAC-3' (SEQ ID NO:30), or 5'-CCTAGATGCAATGAAACACTAT-3' (SEQ ID NO:31).

Immunoblot Analysis of Chloroplast Proteins

Light grown four-day-old seedlings and 3-week-old rosette leaves of wild type, bpg2-1, and bpg2-2 were ground in liquid nitrogen and extracted by boiling with two volumes/fresh weight of 1× Laemmli buffer [50 mM Tris-HCl (pH 6.8), 100 mM DTT, 2% (w/v) SDS, 0.1% (w/v) bromophenol blue, and 10% (w/v) glycerol] for immunoblot analysis of Rubisco LSU, SSU, and LHCP. Total proteins for immunoblot analysis of D1 protein were prepared as described (Nakajima et al., 1996). Proteins were separated by SDS-PAGE (12.5% acrylamide separating gel). After electrophoresis, the proteins were stained with Coomassie Brilliant Blue or electrophoretically transferred to Hybond ECL nitrocellulose membrane (Amersham). After blocking overnight in TBS (20 mM Tris, 0.137 M NaCl, pH7.4, 0.05% polyoxyethlene sorbital monolaurate) buffer containing 5% non-fat milk (Morinagamilk) at room temperature, the membrane was incubated in TBS buffer containing non-fat milk with polyclonal antibody for 1 h at room temperature. After washing in TBS buffer, the blots were incubated with horseradish peroxidase-conjugated secondary antibody (Promega for Rubisco L/S and LHCP, and Cosmo Bio for D1) for 1 h at room temperature, and the complexes were made visible with ECL Immoblin Western (Millipore). The polyclonal antibody against the tobacco Rubisco L/S complex was provided by F. Sato of Kyoto University. The polyclonal antibody against D1 and LHCP protein was obtained from Agrisera. LAS-4000 mini (Fuji Film) was used for detection.

Results

Isolation of the bpg2 Mutant.

Brz binds directly to the cytochrome P450 steroid C-22 hydroxylase encoded by the DWF4 gene and specifically inhibits BR biosynthesis (Asami et al., 2000, 2001). Brz treatment reduces BR content in plant cells and causes the same de-etiolation and dwarf phenotype as the BR deficient mutant. In addition to these morphological changes, Brz treatment also induced chloroplast gene expression in the dark for both wild type and the BR-deficient mutant (Nagata et al., 2000). These results and research on BR-deficient mutants suggest that BR plays a role in regulating chloroplast development. In the light, Brz also promotes greening of cotyledons of wild-type *Arabidopsis*. If the pale green phenotype of a mutant is independent of BR signaling, the pale color should be restored to darker green by Brz. Pale green mutants which are not recoverable by Brz may have decreased or disrupted BR signaling for chloroplast regulation.

Figure 1:
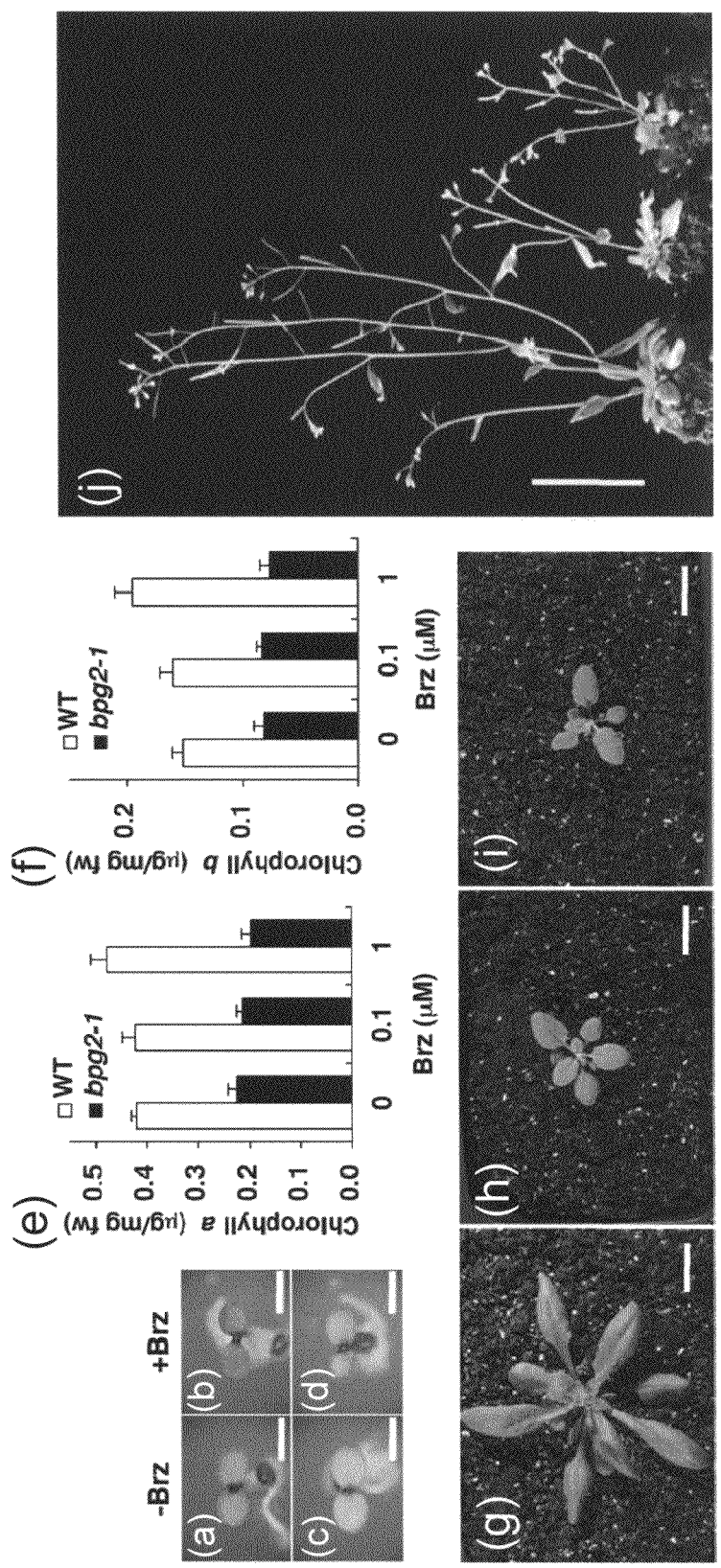
FIG. 1. Phenotype of bpg2 mutants. (a to d) Cotyledon of wild type (a and b) and bpg2-1 (c and d) grown on ½ MS medium in long days (16 h light and 8 h dark) without Brz (a and c) or with 1 μM Brz (b and d) for 4 days. Bars=1 mm. (e and f) Endogenous contents of chlorophyll a (e) and chlorophyll b (f) of wild type (WT) and bpg2-1 grown without Brz (0 μM) or with Brz (0.1 μM and 1 μM) for 4 days in long days (16 h light and 8 h dark). Error bar indicates SE. (g to i) Wild type (g), bpg2-1 (h), and bpg2-2 (i) grown in long days (16 h light and 8 h dark) on soil for 2 weeks. Bars=10 mm. (j) Wild type, bpg2-1 and bpg2-2 grown in long days (16 h light and 8 h dark) on soil for 3 weeks. Bar=5 cm.

We screened approximately 10000 *Arabidopsis* activation tagged lines (Nakazawa et al., 2003) and isolated a recessive mutant, Brz-insensitive-pale green2-1 (bpg2-1), which retained pale green cotyledons when grown with Brz in the light (FIG. 1c, d). bpg2-1 seedlings had pale green cotyledons compared to cotyledons of wild-type seedlings on media containing different concentrations of Brz (FIG. 1 a-d).

For detailed analysis of cotyledon greening, endogenous levels of chlorophyll a and b in wild-type and bpg2-1 seedlings were measured with or without Brz in the light (FIG. 1e, f). bpg2-1 accumulated about half the amount of chlorophyll a (FIG. 1e) and b (FIG. 1f) compared to wild-type seedlings. In wild-type seedlings, endogenous chlorophyll a and b levels were increased by Brz treatment, whereas in bpg2-1 seedlings, they were not. When grown on soil, bpg2-1 produced pale green semidwarf rosette leaves (FIG. 1h) and inflorescences (FIG. 1j). This phenotype differed from the dwarf phenotype of the BR-deficient mutant det2 and the BR-insensitive mutant bri1.

In general, BR-deficient mutants have a short hypocotyl in the dark, but the bpg2-1 hypocotyl was elongated, as in the wild type (data not shown). This indicates that BR biosynthesis was normal in bpg2-1 and that BPG2 is not involved in BR biosynthesis. Furthermore, when bpg2-1 was grown with Brz in the dark, bpg2-1 showed the same short hypocotyl as the wild type plants (data not shown). These results suggest Brz binds to cytochrome P450 C-22 hydroxylase and inhibits BR biosynthesis in bpg2-1. bpg2-1 is thus insensitive to Brz effects, especially with respect to chloroplast regulation, and the semidwarf phenotype might be a secondary effect of chloroplast deficiency. From these analyses it can be inferred that, after the initial perception of BR by the receptor BRI1, BR signaling can be separated into at least two phases: developmental regulation and chloroplast regulation, and BPG2 appears to play a major role in chloroplast regulation by BR signal transduction.

BPG2 is a GTPase Evolutionarily Conserved in Plants, Green Algae, and Bacteria.

Figure 2:
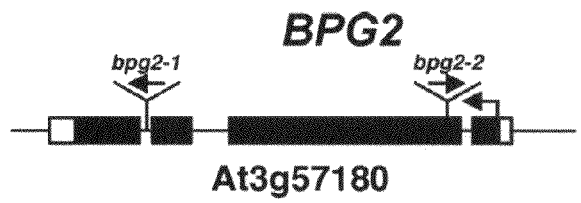
FIG. 2. Identification and structure of BPG2. (a) Gene structure of BPG2 with mutations by T-DNA insertions. T-DNA of bpg2-1 was inserted in 1922 bp upstream of start codon (ATG). T-DNA of bpg2-2 was inserted in 113 bp upstream of start codon. (b) RT-PCR analysis of BPG2 expression in wild type (WT), bpg2-1, and bpg2-2. ACT2 served as an internal control. (c) Phylogenic analysis of the relationship between BPG2 and BPG2 homologs in plants, green algae, and Gram-positive bacteria. GenBank accession numbers: *O. sativa*1, CM000143; *O. sativa*2, NM 001064237; *V. vinifera*1, CU459251; *V. vinifera*2, CU459220; *M. truncatula*, AC158502; *P. patens*, XM 001758456; *Ostreococcus lucimarinus*, XM 001418245; *Chlamydomonas reinhardtii*, XM 001700742; *Listeria monocytogenes*, NC 003210; *Exiguobacterium sibiricum*, NC 010556; *Lactobacillus casei*, NC 008526; *Enterococcus faecium*, NZ AAAK03000016; *Lactococcus lactis*, NC 009004; *Streptococcus sanguinis*, NC 009009; *Geobacillus thermodenitrificans*, NC 009328; *Lysinibacillus sphaericus*, NC 010382; *Staphylococcus haemolyticus*, NC 007168; *Oceanobacillus iheyensis*, NP 692909; *Bacillus subtilis*, Z99117. (d) Sequence alignment of BPG2 (SEQ ID NO:1) and BPG2 homologs in plants and *Bacillus subtilis* YqeH (SEQ ID NOs:32-37). Color bars under the sequence indicate zinc finger domain (gray) and GTP-binding motifs as G4 (black), G1 (blue), G2 (red), and G3 (green).
Figure 2:
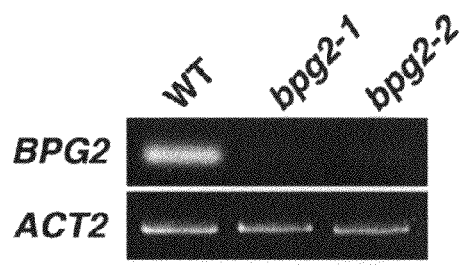
Figure 2:
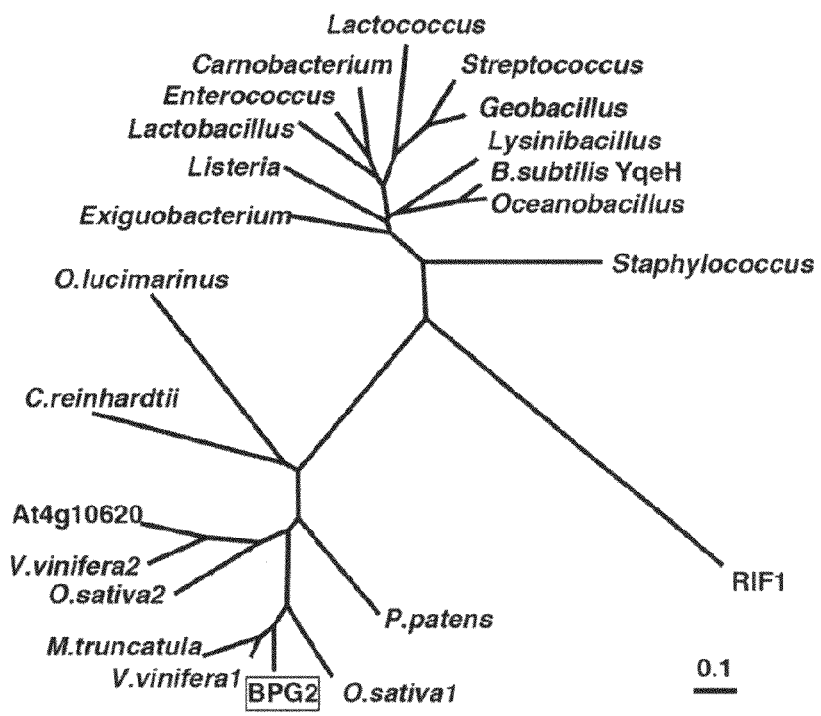

Co-segregation of the Brz-insensitive, pale green phenotype with a selection marker after back crossing with the wild type indicated that bpg2-1 was a recessive mutant with a single T-DNA insertion. To identify the bpg2-1 mutation, we isolated a T-DNA insertion site on the bpg2-1 genome by TAIL-PCR (Liu et al., 1995) to amplify the fragment adjacent to the left border of T-DNA with a combination of degenerate primers and T-DNA-specific primers. The identified T-DNA insertion site was in the third intron of At3g57180 (FIG. 2a). PCR results indicated that bpg2-1 lacked an enhancer region of T-DNA (data not shown) and was a recessive mutant, suggesting that the bpg2-1 phenotype was caused by disruption of At3g57180 by the T-DNA insertion. Expression of full-length At3g57180 in bpg2-1 was not detected by RT-PCR (FIG. 2b). To confirm that disruption of At3g57180 is responsible for the bpg2-1 mutant, we isolated the knockout mutant of bpg2-2 (SALK_068713), from a mutant pool of T-DNA insertion lines at the Arabidopsis Biological Resource Center (ABRC; FIG. 2a). RT-PCR indicated that expression of At3g57180 was also very low in the bpg2-2 mutant (FIG. 2b), and a pale green phenotype similar to bpg2-1 was observed (FIG. 1i, j, 3e, f, k-m).

BLAST searches for the BPG2 amino acid sequence identified similar genes in Arabidopsis (AGI code NO. At4g10620: unknown protein, RIF1/NOS1/NOA1: At3g47450, Flores-Pérez et al., 2008), rice (Oryza sativa), medicago (Medicago truncatula), grape (Vitis vinifera), the moss Physcomitrella patens, and the green algae Ostreococcus lucimarinus and Chlamydomonas reinhardtii (FIG. 2c). Further searches suggested that some bacteria had BPG2 homologous genes that included a YqeH-type GTPase in Gram-positive bacteria such as Bacillus subtilis (Uicker et al., 2007; Loh et al., 2007; FIG. 2c). The YqeH-type GTPase of bacteria has a GTP-binding domain with a G4-G1-G2-G3 motif and an N-terminal putative zinc finger motif with a conserved sequence beginning with $CXXCX_n$ and ending with CXXC (Loh et al., 2007). The four GTP-binding domains and the zinc finger motif were also found in a putative BPG2 amino acid sequence (FIG. 2d).

To confirm that disruption of the GTPase homologous gene caused the bpg2-1 and bpg2-2 mutant phenotype, the BPG2 candidate cDNA was placed under the control of the cauliflower mosaic virus (CaMV) 35S promoter and transformed into bpg2-1 and bpg2-2 by Agrobacterium-mediated transformation. The resulting bpg2-1:35S-BPG2 and bpg2-2:35S-BPG2 showed a normal green phenotype, confirming that decreased chlorophyll a and b levels in bpg2-1 and bpg2-2 were rescued by 35S-BPG2 (FIG. 3g-j, m).

The bpg2:35S-BPG2 transformants also showed an increase in chlorophyll levels following Brz treatment and rescue of Brz sensitivity in bpg2-1 and bpg2-2 (FIG. 3k, l). Furthermore, the semidwarf rosette leaves of 3-week-old bpg2-1 and bpg2-2 were rescued by 35S-BPG2 (FIG. 3m, Table 1).

TABLE 1

Leaf sizes of Wild type, bpg2-1, bpg2-2, bpg2-1:35S-BPG2 and bpg2-2:35S-BPG2.

| Plant | Leaf width (mm) | Leaf length (mm) | Ratio (length:width) |
|---|---|---|---|
| WT | 10.34 ± 0.59 | 18.45 ± 0.87 | 1.80 ± 0.07 |
| bpg2-1 | 9.69 ± 0.28 | 14.05 ± 0.39 | 1.46 ± 0.04 |
| bpg2-2 | 9.57 ± 0.34 | 13.40 ± 0.63 | 1.41 ± 0.07 |
| bpg2-1:35S-BPG2 | 12.27 ± 0.67 | 21.95 ± 1.19 | 1.82 ± 0.11 |
| bpg2-2:35S-BPG2 | 11.11 ± 0.38 | 23.12 ± 1.01 | 2.12 ± 0.16 |

Data are means ± SE. n = 12 for each plant.

Thus, these results showed that the normal BPG2 gene was able to complement the bpg2 mutant and rescue the wild type phenotype.

Figure 4:
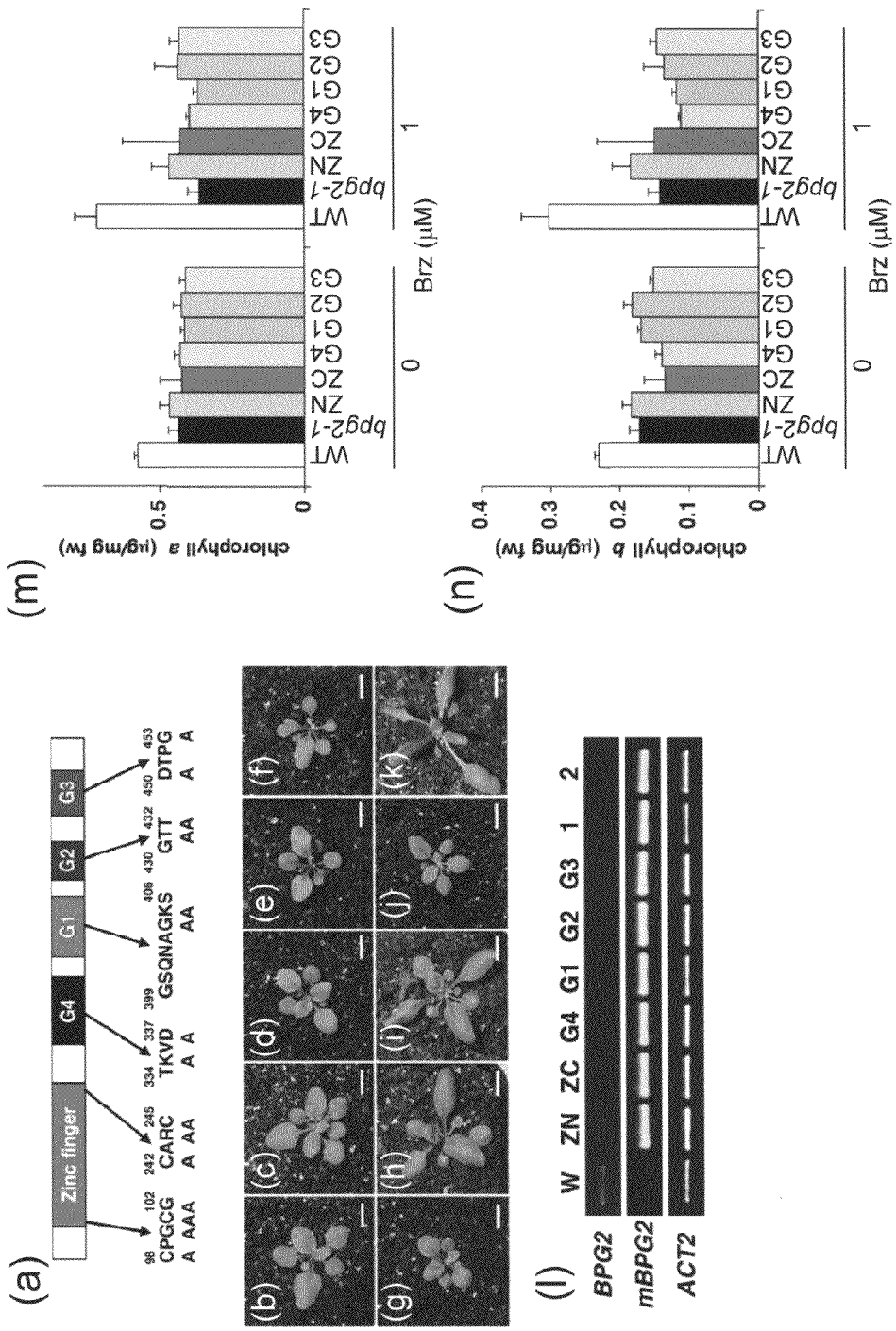
FIG. 4. Phenotype of bpg2-1 transformed with the wild type and mutated bpg2 gene in the zinc finger domain and GTP-binding motifs. (a) Predicted domain structure of BPG2 with targeted mutagenesis in the zinc finger motif or GTP-binding domains (top line). The conserved amino acid sequences were exchanged to alanine (bottom line). (b to g) bpg2-1 plants transformed by 35S::mutated bpg2-GFP with mutations in zinc finger N' (b), zinc finger C' (c), G4 (d), G1 (e), G2 (f), and G3 (g). 35S::wild-type BPG2-GFP was transformed into bpg2-1 (h) and bpg2-2. (i). Control plants without transformation are bpg2-1 (j) and wild-type *Arabidopsis* Col-0 (k). These plants were grown in long days (16 h light, 8 h dark) on soil for 2 weeks. (l) RT-PCR analysis of expression of BPG2 and mutant-bpg2 in transformed bpg2-1 and wild type. Expression of each mutated-bpg2 was detected in bpg2-1 transformed by mutated-bpg2 cDNA mutagenized in zinc N' (ZN), zinc C' (ZC), G4 (G4), G1 (G1), G2 (G2), and G3 (G3). Each mRNA were amplified by bpg2-specific primers and GFP-specific primers. Expression of wild-type BPG2 was detected in wild-type *Arabidopsis* but not in transformed bpg2-1 plants. ACT2 served as an internal control. (m and n) Endogenous contents of chlorophyll a (m) and chlorophyll b (n) of wild type (WT), bpg2-1 and six transformants grown without Brz (0 μM) or with Brz (1 μM) for 4 days in long days (16 h light and 8 h dark). Error bar indicates SE.

To investigate the contribution of the domains to the role of BPG2 in chloroplast development, mutant forms of conserved amino acids in zinc finger N' (C98A, G100A, C101A and G102A), zinc finger C' (C242A, R244A and C245A), and in the GTP-binding motifs G4 (K335A and D337A), G1 (G404A and K405A), G2 (T431A and T432A), and G3 (D450A and G453A) were replaced by alanine (FIG. 4a) and constructed under the CaMV 35S promoter with the Green Fluorescent Protein (GFP) of the pGWB5 vector (Nakagawa et al., 2007). These 35S::mutated BPG2-GFPs were transformed into the bpg2-1 mutant (FIG. 4b-g). bpg2-1 with 35S::BPG2-GFP (FIG. 4h) and bpg2-2 with 35S::BPG2-GFP (FIG. 4i) showed a wild-type normal green phenotype compared to the bpg2-1 pale green phenotype (FIG. 4j). However, when mutated-BPG2 genes driven by the CaMV 35S promoter were expressed in the bpg2-1 mutant (FIG. 4l), all six transformants remained pale green and could not be restored to the wild-type phenotype (FIG. 4b-g). Furthermore, chlorophyll levels in the transformants remained low and Brz sensitivity was not rescued in bpg2-1 and bpg2-2 (FIG. 4m and n). These results suggest that the GTP-binding motifs and zinc finger motif play important roles in chloroplast development and are regulated by BPG2.

Localization of BPG2 and Function in Chloroplast Differentiation.

To determine the subcellular localization of the BPG2 protein, a translational BPG2-GFP was expressed under the constitutive CaMV 35S promoter and introduced into wild-type Arabidopsis (FIG. 4h). GFP fluorescence was detected in chloroplasts of guard cells of 35S::BPG2-GFP plants (FIG. 5b, c), and the signal was merged with chlorophyll autofluorescence (FIG. 5a-d). These results suggest that the BPG2 protein localized in chloroplasts.

Figure 5:
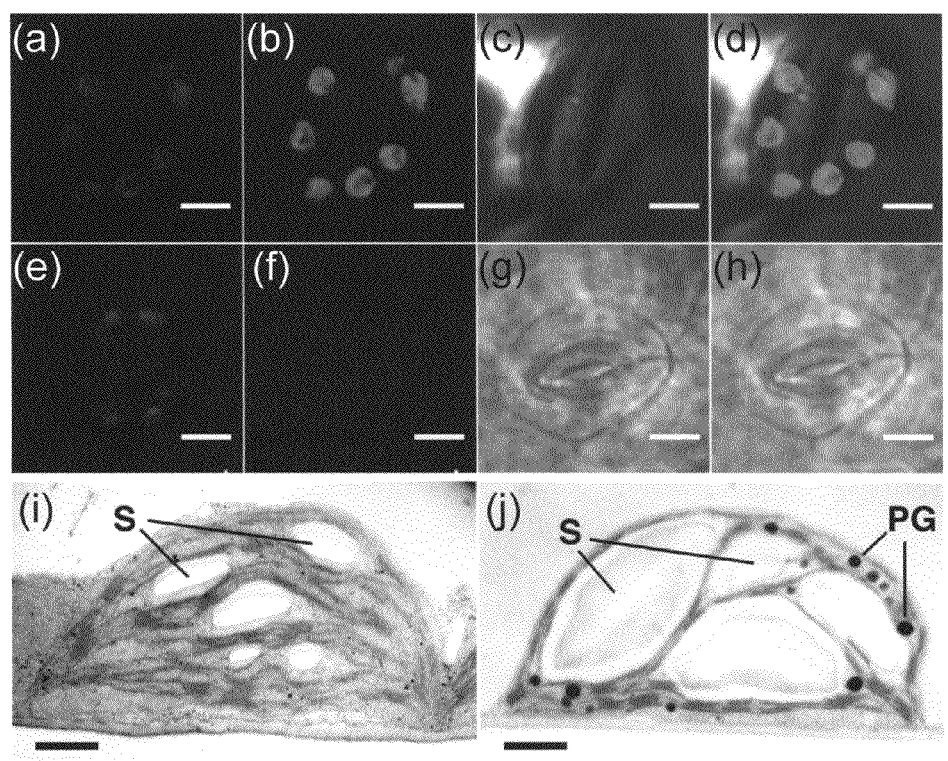
FIG. 5. Localization of BPG2 protein in chloroplasts and morphology of the chloroplast in bpg2-1. (a to h) Confocal laser scanning microscopy of guard cells in transformants in 35S::BPG2-GFP (a to d) and wild-type (e to h) plants. Plants were grown for 2 weeks on ½ MS medium containing kanamycin for 2 weeks. a, e: Red autofluorescence of chlorophyll. b, f: Green fluorescence of GFP. c, g: Bright field images. d: BPG2-GFP merged image of a, b, and c. h: Wild type; merged image of e, f, and g. Bars=5 μm. (i and j) Electron microscopy of wild type (i) and bpg2-1 (j) in chloroplasts of rosette leaves. Plants were grown on soil for 3 weeks under long-day conditions. PG; plastoglobule. S; starch granule. Bars=1 μm.

The pale green phenotype of bpg2 mutants and localization of BPG2 protein suggest that BPG2 plays a role in chloroplast morphology. To analyze the role of BPG2 in chloroplast differentiation, electron microscope observations of the wild type and bpg2-1 were conducted (FIG. 5i, j). Abnormal chloroplasts were observed in bpg2-1 leaves. While three-week-old wild-type chloroplasts had stacked grana thylakoids (FIG. 5i), plastids of the bpg2-1 mutant had fewer stacked grana in the thylakoids, more starch grains, and more and larger plastoglobules (FIG. 5j). These results suggest that BPG2 is important for normal chloroplast differentiation.

Tissue-Specific and Light-Regulated Expression of BPG2.

Figure 6:
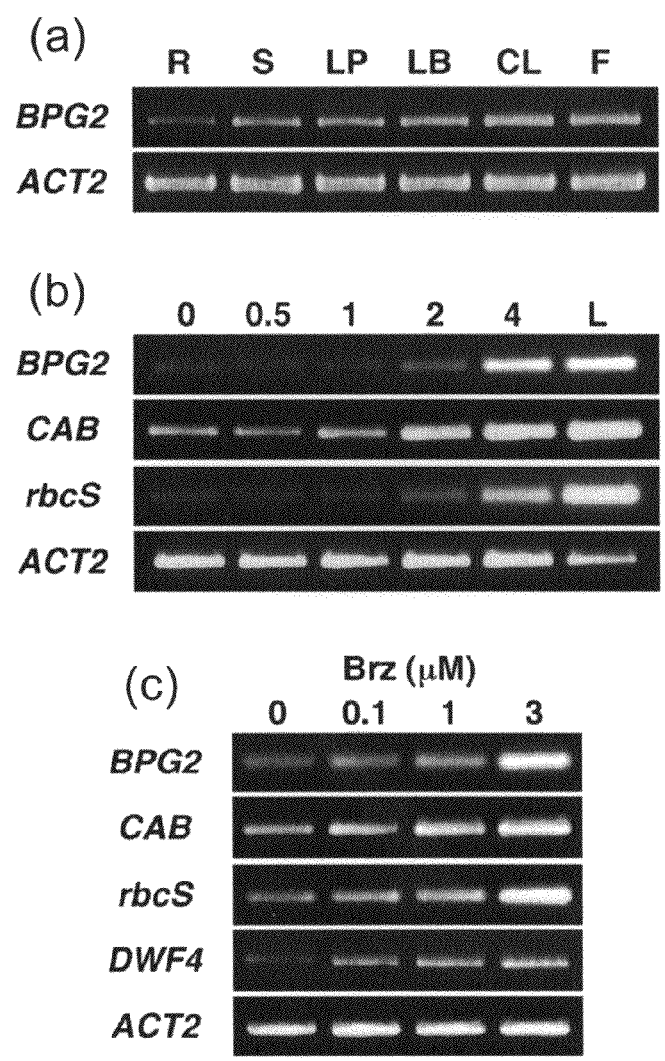
FIG. 6. Inducible expression of BPG2 by light and Brz. (a) RT-PCR analysis of BPG2 gene expression in different organs: root (R), stem (S), rosette leaf blade (LB), rosette leaf petiole (LP), cauline leaves (CL), and flowers (F) of wild-type *Arabidopsis*. ACT2 served as an internal control. (b) RT-PCR analysis of expression of BPG2, CAB, and rbcS after exposure to light. Total RNAs were extracted from the wild type germinated in the dark for 7 days and exposed to light for 0 (lane 1, 0), 0.5 (lane 2, 0.5), 1 (lane 3, 1), 2 (lane 4, 2), or 4 h (lane 5, 4), and from 7-day-old wild type under long-day conditions (16 h light and 8 h dark; lane 6, L). (c) RT-PCR analysis of expression of BPG2, CAB, rbcS, and DWF4 on Brz. Total RNAs were extracted from wild type germinated in the dark for 7 days with Brz. Each lane shows different concentrations of Brz: 0 μM (lane 1, 0), 0.1 μM (lane 2, 0.1), 1 μM (lane 3, 1), and 3 μM (lane 4, 3).

To analyze the possible function of BPG2 in plastids in different tissues, expression of BPG2 under different conditions was examined using RT-PCR (FIG. 6). The BPG2 gene was highly expressed in stems, petioles, rosette leaf blades, cauline leaves, and flowers of 3-week-old wild type, but only faintly in roots (FIG. 6a). As BPG2 gene expression was found in all green tissues, the effect of light on the expression of BPG2 was analyzed using total RNA isolated from seedlings harvested at 0, 0.5, 1, 2, and 4 h after transfer of dark-grown plants to light (FIG. 6b). In light-stimulated plants, two nuclear-encoded genes, CAB, the light-harvesting chlorophyll a/b binding protein, and rbcS, the small subunit of ribulose-1, 5-bisphosphate carboxylase oxygenase (Rubisco), began to be expressed after 0.5 and 2 h of light stimulation (FIG. 6b) and expression of BPG2 continued after 2 h of light treatment. This is consistent with the expression patterns of CAB and rbcS (FIG. 6b).

Dark-grown BR-deficient mutants express chloroplast genes, such as CAB and rbcS (Chory et al., 1991; Szekeres et al., 1996), and dark-grown wild type plants treated with Brz accumulate more Rubisco protein than the wild type without Brz (Nagata et al., 2000). To study the effect of BR on BPG2 gene expression, we performed RT-PCR analysis of wild-type plants grown in the dark with Brz (FIG. 6c) and found that expression of CAB and rbcS was increased by Brz. DWF4 encodes cytochrome P450 (CYP90B1), and its expression is increased by feedback mechanisms in BR-deficient mutants. These expression levels showed that Brz treatment of dark-grown wild type caused BR deficiency and promoted chloroplastic gene expression in the dark (FIG. 6c). In the Brz-treated tissues, BPG2 gene expression actually increased (FIG. 6c), suggesting that BPG2 gene expression is negatively regulated by BR and positively by light in green organs.

Expression of Genes Encoded by the Chloroplast Genome of the BPG2 Mutant.

Figure 7:
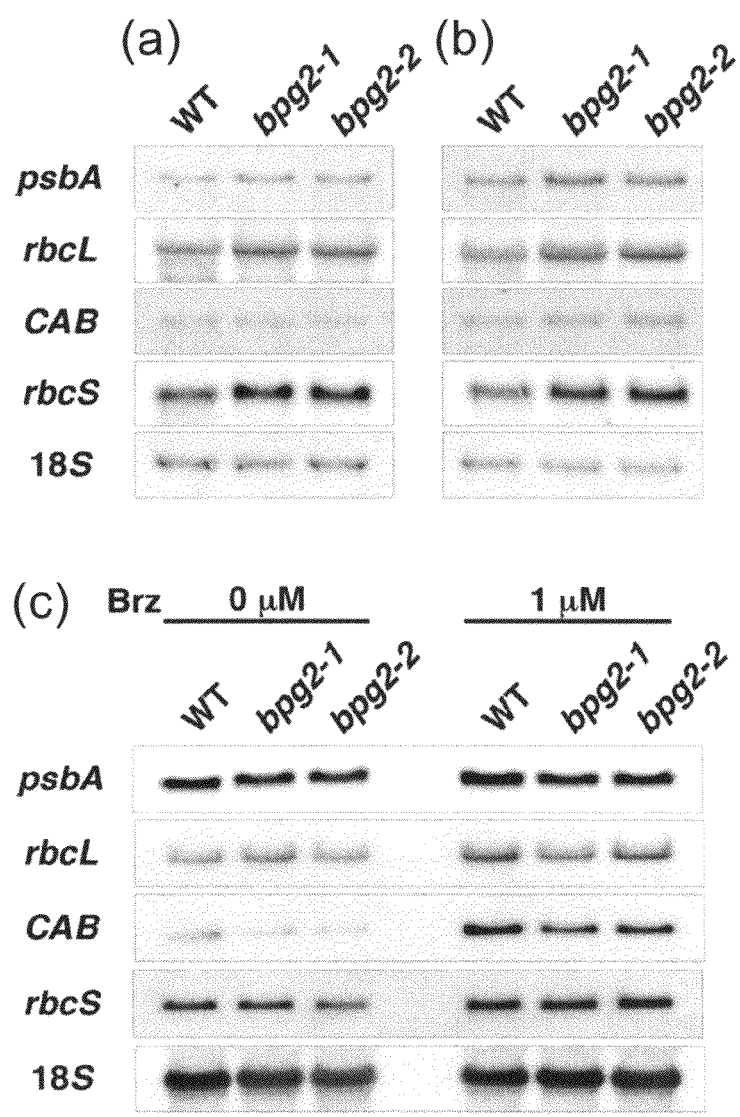
FIG. 7. Chloroplast gene expression in bpg2 mutants. Total RNA was extracted from light grown 4-day-old seedlings (a), 3-week-old rosette leaves (b) and dark grown 5-day-seedling (c) of wild type (WT), bpg2-1, and bpg2-2. Northern blot analysis was carried out using probes for psbA and rbcL, encoded in the chloroplast, and rbcS, CAB, and 18S rRNA, encoded in the nucleus. (c) Seedlings were germinated with 0 or 1 μM Brz in the dark.

The plastid genome of *Arabidopsis* encodes about 87 open reading frames (ORFs) and four rRNAs on 154 kbp of DNA (Arabidopsis Genome Initiative, 2000). Transcriptional, post-transcriptional, and translational regulatory mechanisms in chloroplasts have been analyzed (Leister, 2003), but molecular mechanisms for chloroplast regulation by brassinosteroid remain unknown. To investigate the function of BPG2 responsible for the pale green phenotype, we performed expression analysis of chloroplast-encoded photosynthesis genes by Northern blot analysis using wild-type and bpg2 plants (FIG. 7). No reduction in expression of chloroplast-encoded rbcL, the large subunit of Rubisco, and psbA, a D1 protein of photosystem II, was found in bpg2 mutants compared to the wild type in seedlings (FIG. 7a) or rosette leaves at the reproductive stage (FIG. 7b). There was also no reduction in expression of CAB and rbcS in the mutants (FIG. 7a and b). Brz stimulated increased expression of psbA, rbcL, CAB and rbcS in bpg2 mutants, but to the same degree in bpg2 mutants as in wild type (FIG. 7c).

Essential Role of BPG2 for Chloroplast rRNA Maturation.

The chloroplast genome encodes 16S and 23S rRNA. These rRNAs are encoded in a single operon with three tRNAs and are expressed as a 7.4-kb precursor that is post-transcriptionally processed (Strittmatter and Kössel, 1984; FIG. 8a). We performed Northern blot analysis of chloroplast rRNA in wild type and bpg2 mutants at the seedling and reproductive stages (FIG. 8b, c) with the specific probes (I to V) indicated in FIG. 8a.

When blots were analyzed with a 16S rRNA-specific probe (probe I), levels of a mature 16S rRNA transcript of 1.5-kb were lower in bpg2 mutants compared with the wild type at both seedling and reproductive stages (FIG. 8bI, cI). Accumulation of a 1.7-kb precursor transcript was detected at higher levels in bpg2 than in wild type. A mature 16S rRNA was generated by endonucleolytic cleavage of the intergenic space of a primary transcript, about 180 bp downstream of the mature 16S 3' end. To identify the 1.7-kb RNA band as pre-16S rRNA, blots were analyzed with probe II, an intergenic spacer of the 16S rRNA flanking region. Probe II detected 1.7-kb RNA in bpg2 mutants, but not in the wild type, suggesting pre-16S rRNA accumulated in bpg2 (FIG. 8bII, cII).

When blots were analyzed with a 23S rRNA-specific probe (probe III), 23S rRNA accumulated as seven major transcripts, viz. 3.2-, 2.9-, 2.4-, 1.7-, 1.2-, 1.0-, and 0.5-kb bands (FIG. 8a). In both seedling and reproductive stages, no differences in the size of the seven transcripts between wild type and the bpg2 mutant were observed. The 3.2-kb band that is a 23S-4.5S dicistronic precursor accumulated about three-fold in bpg2 mutants compared to the wild type at the seedling stage (FIG. 8bIII), and about 8.5-fold in bpg2 mutants at the reproductive stage (FIG. 8cIII). The 2.4-kb band decreased in bpg2 at the seedling stage (FIG. 8bIII), but the 2.9-kb and 2.4-kb bands increased four- and eight-fold, respectively, in bpg2 mutants at the reproductive stage (FIG. 7cIII). Bands of 1.2 and 1.0 kb that are produced by "hidden breaks" after incorporation into ribosomes did not differ between bpg2 mutants and the wild type (FIG. 8bIII, cIII).

When blots were analyzed by 4.5S and 5S rRNA-specific probes (probes IV and V), the 3.2-kb band that is the 23S-4.5S precursor was also detected in bpg2 mutants (FIG. 8bIV, cIV). Precursor bands were not detected in bpg2 by 5S rRNA, but decreased 5S rRNA in bpg2 mutants at the seedling stage and increased 5S in bpg2 mutants at the reproductive stage were found (FIG. 8bV, cV). These results suggest that BPG2 protein plays an important role in processing or maturation of chloroplast rRNA.

Decreased Accumulation of Chloroplast Proteins in bpg2.

Figure 9:
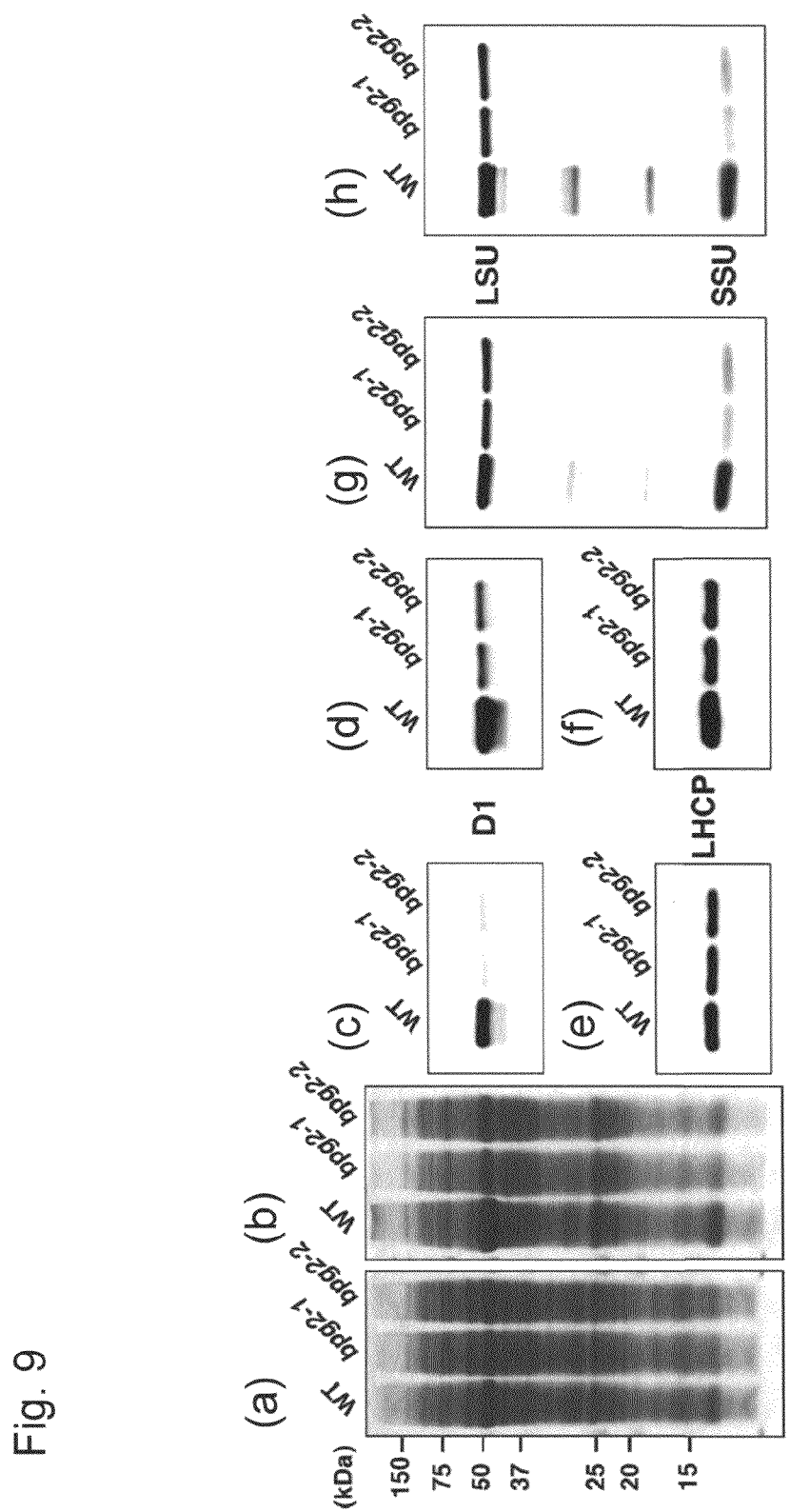
FIG. 9. Decreased accumulation of proteins from genes encoded on the chloroplast genome in bpg2. Total protein was prepared from 4-day-old seedlings (a, c, e, and g) and 3-week-old rosette leaves (b, d, f, and h) of wild type (WT), bpg2-1, and bpg2-2. (a and b) Coomassie Brilliant Blue (CBB)-stained gel. (c to h) Immunoblot analyses were performed using polyclonal antibodies against photosystem II D1 protein (c and d), LHCP protein (e and f), and Rubisco LSU and SSU (g and h).

To test whether abnormal rRNA processing or maturation in bpg2 chloroplasts may have an effect on chloroplast protein accumulation, total protein from bpg2 mutants and wild type was analyzed by immunoblotting (FIG. 9). The photosystem II D1 protein encoded by psbA was markedly lower in bpg2 mutants than in the wild type at both seedling (FIG. 9c) and reproductive stages (FIG. 9d). The thylakoid light-harvesting chlorophyll a/b binding protein (LHCP) encoded by CAB was slightly decreased in bpg2 in both seedling (FIG. 9e) and rosette leaves (FIG. 9f). Accumulation of Rubisco large subunit (LSU) protein encoded by rbcL and Rubisco small subunit (SSU) protein encoded by rbcS were lower in bpg2 mutants for both seedling (FIG. 9g) and reproductive stages (FIG. 9h). These results show that translation of chloroplast proteins encoded by the chloroplast genome decreased in bpg2 chloroplasts.

Chloroplast Protein Accumulation was not Increased by Brz in bpg2 Mutants.

Figure 10:
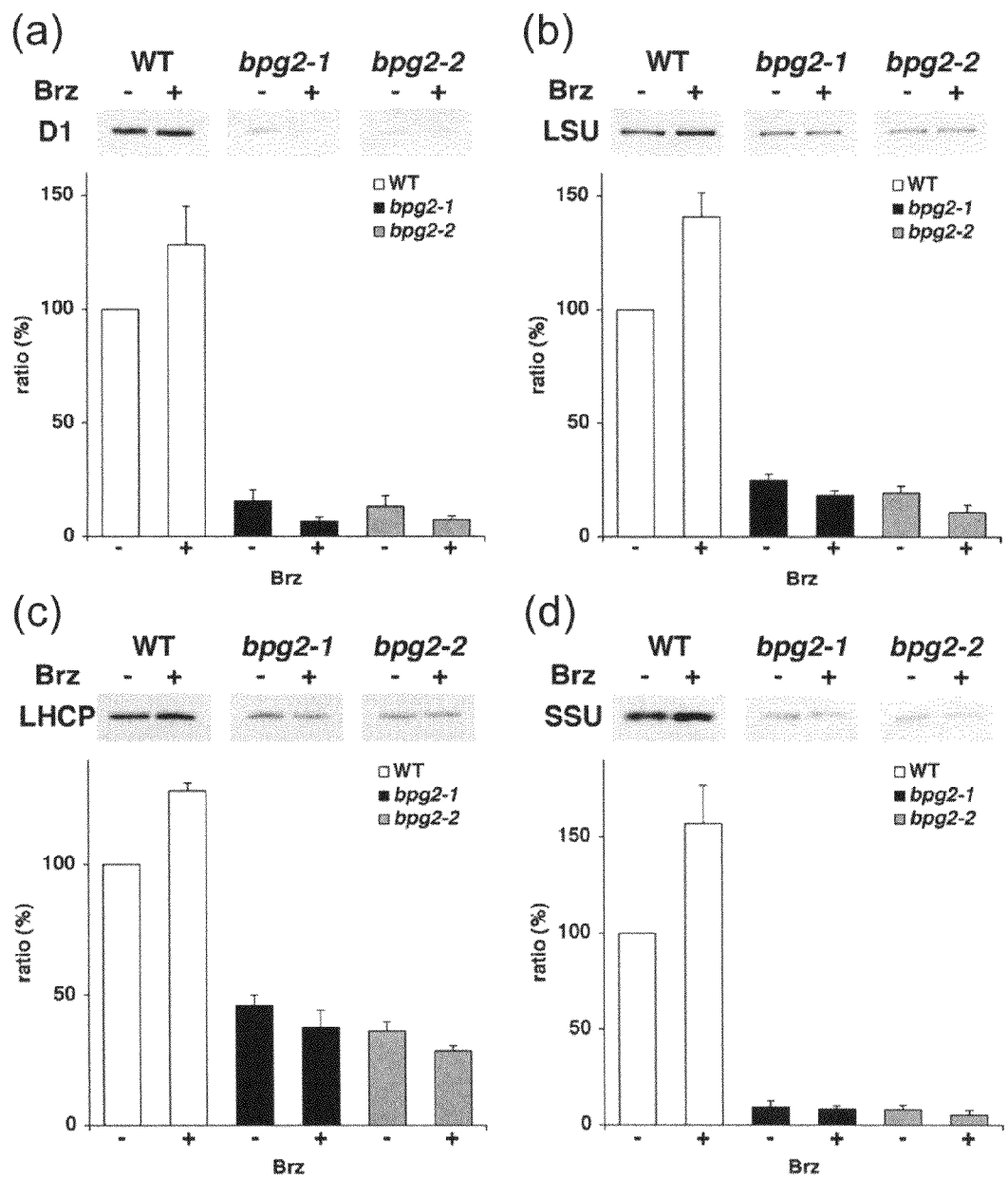
FIG. 10. Accumulation of chloroplast proteins was not increased by Brz in bpg2. Total protein was prepared from wild type (WT), bpg2-1, and bpg2-2 germinated in the light for 3 days with 0 or 1 μM Brz. Immunoblot analyses were performed using polyclonal antibodies against photosystem II D1 protein (a), LHCP protein (b) and Rubisco LSU (c) and SSU (d). Error bar indicates SE.
Figure 11:
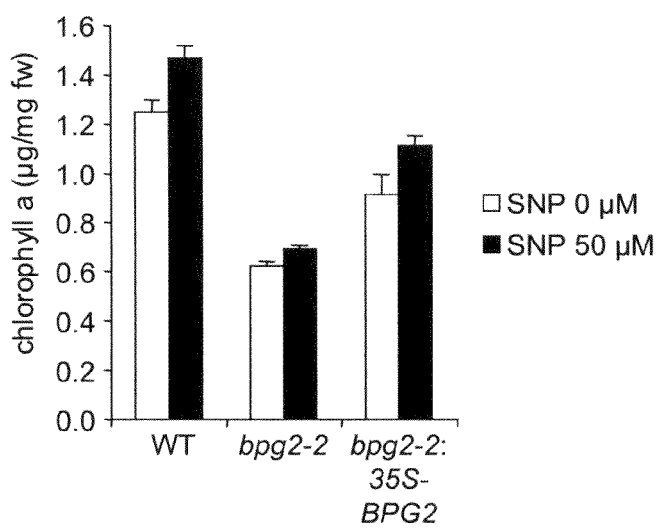
FIG. 11. Endogenous contents of chlorophyll a (FIG. 11a) and chlorophyll b (FIG. 11b) for wild type (WT), and bpg2-2 and bpg2-2 mutants complemented by 35S-BPG2. Plants were grown with nitrate oxide donor SNP (50 μM) or without SNP (0 μM) for 4 days in long days (16 h light and 8 h dark). Error bar indicates SE.
Figure 11:
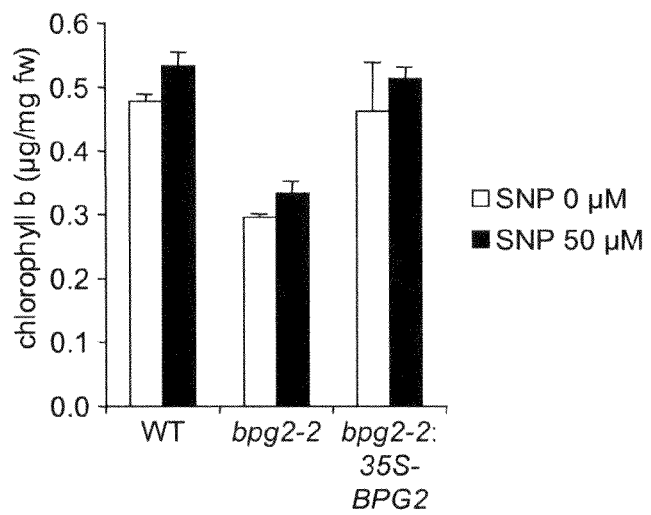

To analyze BPG2 function with BR on chloroplast protein accumulation, we performed immunoblot analysis seedlings of wild type and bpg2 mutants in the light with and without Brz (FIG. 10). In wild type, Rubisco LSU protein from Brz-treated seedlings increased about 1.4-fold and D1 protein increased about 1.3-fold compared to that of no-Brz seedlings (FIG. 10a, b). In bpg2 mutants, Rubisco LSU protein and D1 protein of Brz-treated seedlings were the same as in no-Brz seedlings (FIG. 10a, b). In wild type, nuclear encoded-LHCP protein and Rubisco SSU protein were also increased by Brz treatment (FIG. 10c, d). The effect of BPG2 deficiency on LHCP protein was much smaller than on D1 and Rubisco LSU.

High Accumulation of Chloroplast Proteins in bpg2 Highly Expressing Transformed Lines.

To analyze BPG2 function on chloroplast protein accumulation, we performed immunoblot analysis seedlings of wild type and BPG2 overexpressing transformants grown on soil in the light. At first, we selected BPG2 mRNA overexpressed lines by RT-PCR and identified at least 4 independent transformants BPG2-OX-N0.9, 17, 18 and 19. BPG2-OX-N0.13 is a not higher expressed negative control.

In BPG2-OX, Rubisco SSU protein accumulation increased about 2.2-fold in the highest line BPG2-OX-N0.17 (FIG. 15). In BPG2-OX, D1 protein increased about 1.4-fold (FIG. 16) and LHCP protein is about 1.4 fold higher than controls (FIG. 17).

DISCUSSION

BPG2 Functions as a Translational Regulator of Brassinosteroid Signaling

BRs and their biosynthesis inhibitor Brz can regulate not only plant development but also chloroplast development. The dark-grown BR-deficient mutant det2 and dark-grown wild-type plants treated with Brz showed photomorphogenesis and expression of photosynthetic genes, rbcS and CAB (Chory et al., 1991; Asami et al., 2000, 2001), and increased accumulation of Rubisco LSU and SSU protein (Nagata et al., 2000). Although these physiological relationships between BR and chloroplast regulation are clear, the molecular mechanism has not been revealed.

Here, we screened a Brz-insensitive-pale green mutant bpg2, and identified that the phenotype was caused by the disruption of a novel chloroplast protein containing a putative zinc finger motif and GTP-binding domains. Brz was shown to induce greening for wild type *Arabidopsis*, but the pale green phenotype bpg2 mutant could not be recovered by Brz. Brz induced endogenous chlorophyll levels in wild type *Arabidopsis* but chlorophyll was not induced in the bpg2 mutants (FIG. 1e,f).

Figure 3:
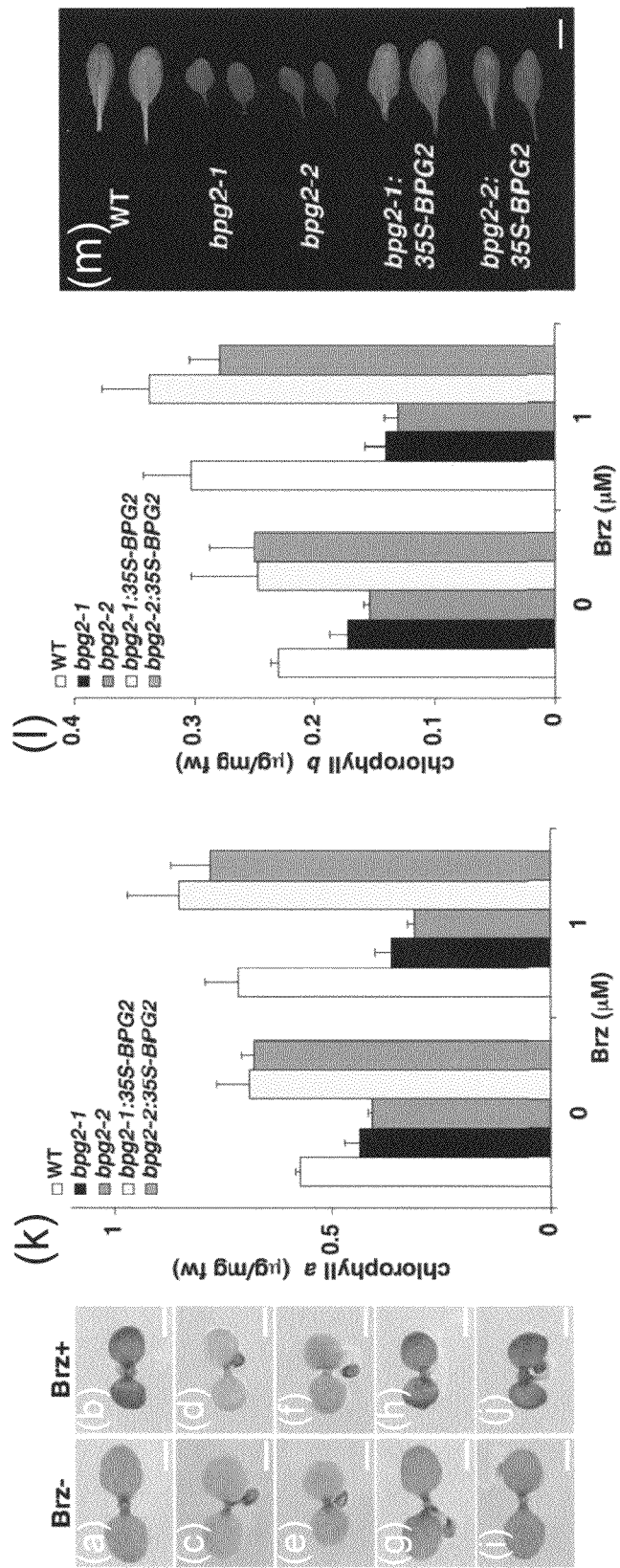
FIG. 3. Effect of Brz on bpg2-2, complementation line of bpg2-1 and complementation line of bpg2-2. (a to j) Cotyledon of wild type (a and b), bpg2-1 (c and d), bpg2-2 (e and f), complementation line of bpg2-1 (g and h) and complementation line of bpg2-2 (I and j) grown on ½ MS medium in long days (16 h light and 8 h dark) without Brz (a, c, e, g and i) or with 1 μM Brz (b, d, f, h and j) for 5 days. Bars=1 mm. (k and l) Endogenous contents of chlorophyll a (k) and chlorophyll b (l) of wild type (WT), bpg2-1, bpg2-2, complementation line in bpg2-1 (bpg2-1:35S-BPG2) and complementation line in bpg2-2 (bpg2-2:35S-BPG2) grown without Brz (0 μM) or with Brz (1 μM) for 4 days in long days (16 h light and 8 h dark). Error bar indicates SE. (m) Rosette leaf morphology of 3-week-old plant in wild type (WT), bpg2-1, bpg2-2, bpg2-1:35S-BPG2 and bpg2-2:35S-BPG2. Bar=1 cm.

SNP is a nitric oxide donor that has been shown to induce greening in wild type *Arabidopsis* (Flores-Peres et al., 2008). When both wild type *Arabidopsis* and bpg2 mutants were treated by sodium nitroprusside (SNP, a nitric oxide donor) under the same conditions of Brz treatment described in FIG. 1, the chlorophyll content of bpg2 mutants could also be induced by SNP (FIG. 1l). These results suggest that the Brz-insensitive-pale green phenotype of bpg2 specifically depends on BR signaling. Furthermore, the abnormal chloroplast ultrastructure observed for bpg2-1 by electron microscopy (FIG. 5j), (FIG. 6) together with reduced BPG2 gene induction in response to Brz, suggest that the BPG2 protein plays an important role in regulation of plastid differentiation under BR signal transduction. Our report on bpg2 is showing the effect of a chloroplast morphogenesis mutant on BR signaling. Though bpg2-1 showed semi-dwarf leaves and inflorescences, the shape was restored to wild type by transformation with wild type BPG2 gene (FIG. 3, Table 1). These results suggested that BPG2 could affect plant development as a consequence of regulation of chloroplast development and photosynthesis by BPG2 itself.

Figure 8:
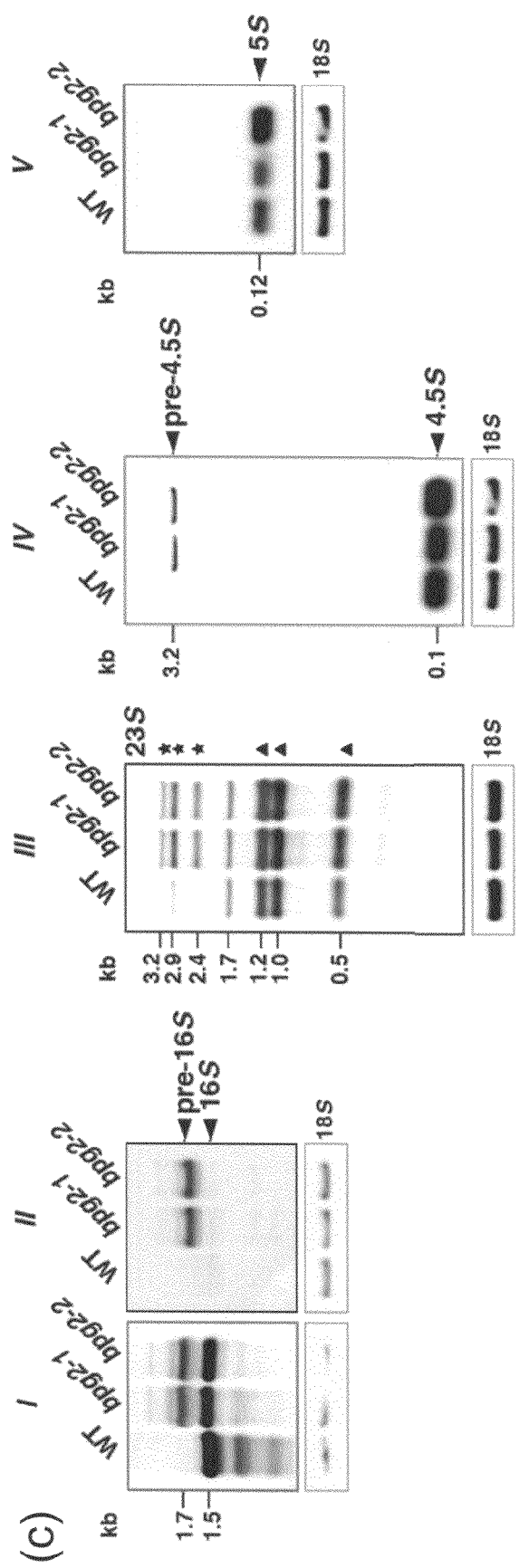
FIG. 8. Accumulation of premature chloroplast rRNA in bpg2. (a) Diagram of the rRNA operon and size of transcripts (kb) shown in (b) and (c). Location of probes (I to V) used for Northern blot analyses are indicated by color bars: I (red), II (yellow), III (purple), IV (blue), and V (green). (b) Northern blot analysis of 4-day-old seedlings of wild type (WT), bpg2-1, and bpg2-2. 18S standard for equal loading. Increased 3.2-kb band is marked by an asterisk and decreased 2.4-kb band is marked by an open triangle. Transcripts with a hidden break are marked by filled triangles. (c) Northern blot analysis of 3-week-old rosette leaves of wild type (WT), bpg2-1, and bpg2-2. Increased bands of 3.2, 2.9, and 2.4 kb are marked by asterisks, and transcripts with a hidden break are marked by filled triangles.
Figure 12:
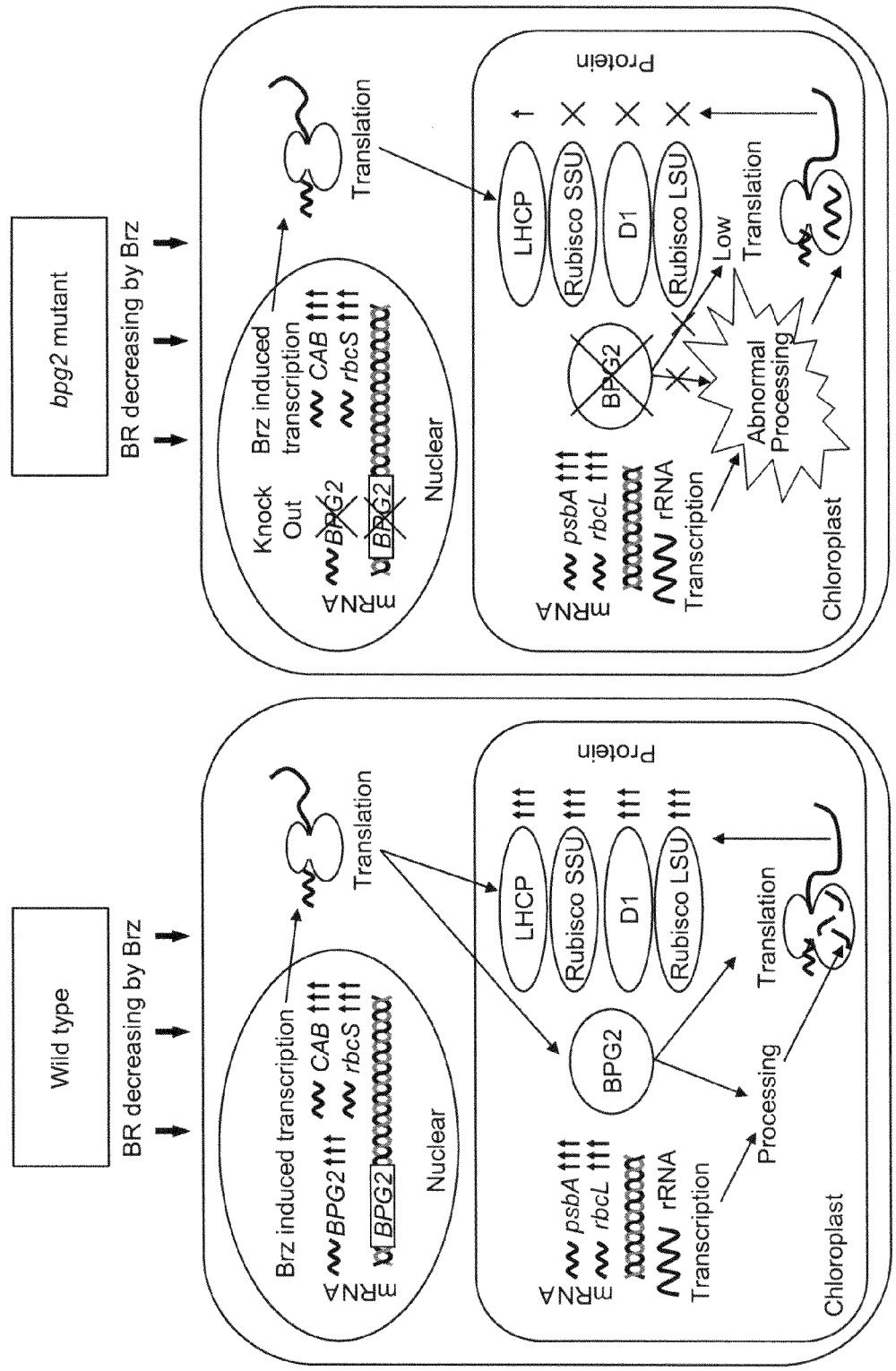
FIG. 12. Possible function of the BPG2 protein in wild type and bpg2 mutant.

A working hypothesis for BPG2 function in chloroplast regulation is described in FIG. 12. In bpg2 mutants, there was no reduction in expression of psbA and rbcL (FIG. 7a, b), but accumulation of D1 protein from psbA and Rubisco LSU protein translated from rbcL was decreased compared to the wild type (FIG. 9c, d, g, h). In contrast to these chloroplast-encoded proteins, there was a lower ratio of reduction for the nuclear-encoded protein LHCP in bpg2 mutants relative to the wild type (FIG. 9e, f). In the bpg2 mutant, we identified abnormal accumulations of pre-16S rRNA and pre-23S rRNA, and abnormal fragmentation of 23S rRNA compared to wild type (FIG. 8). This fragmentation of 23S rRNA is also widespread in bacteria.

In many bacteria, rRNA splicing and fragmentation are tightly related to quality control of rRNA during the assembly of the ribosomal subunits and are shown to be important for cell viability (Cheng and Deutscher, 2003; Evguenieva-Hackenberg, 2005). Bacterial pre-23S and pre-16S rRNA are spliced after polycistronic transcription by endoribonuclease, RNaseIII (Evguenieva-Hackenberg, 2005). Posttranscriptional regulation of mRNA has also been analyzed in detail for bacteria. Bacterial mRNA is generally encoded without introns and the full length mRNA is not regulated by splicing but controlled by degradation with exoribonuclease (Kennel, 2002). The posttranscriptional regulation of bacterial mRNA and rRNA are considered to be controlled by two different systems. As the chloroplast gene expression system is considered to be similar to the prokaryotic system, abnormal levels of chloroplast protein in bpg2 may be largely regulated by accumulation of abnormal rRNA.

Finally, we analyzed the effect of Brz on chloroplast protein accumulation in the light-germinated bpg2 mutant. For the wild type, accumulation of chloroplast genome-encoded Rubisco LSU protein and D1 protein clearly increased under Brz treatment in the light (FIG. 10). In contrast, Brz had little effect on chloroplast protein accumulation in the light-germinated bpg2 mutant (FIG. 10). These results showed that disruption of BPG2 function interferes with the stimulation by Brz of chloroplast protein translation or accumulation. Thus, BPG2 may regulate chloroplast protein translation and/or accumulation according to the regulation of chloroplast rRNA maturation in BR signal transduction. Although the un-spliced pre-16S and pre-23S rRNA could be clearly detected in the bpg2 mutant, normally spliced 16S and 23S rRNAs-looked to be the major products. Nonetheless, D1 and RubisCo LSU proteins were largely reduced in bpg2 mutants. Enhanced inhibition of translation has also been detected in an *Arabidopsis* mutant of RNR1, an exoribonuclease for chloroplast rRNA, but the molecular mechanism in rnr1 has yet to be elucidated (Bollenbach et al., 2005). In bpg2, the abnormal ribosomes with un-spliced rRNA could limit the rate of translation, and repeated translational delay might cause the larger reduction of protein accumulation that is observed in these mutants.

ClpB3 and ClpC1 are thought to act as molecular chaperones for chloroplast protein folding, and disruption mutants clpB3 and clpC1 showed a pale green phenotype and reduced accumulation of photosynthetic protein complexes (Myouga et al., 2006; Nakagawara et al., 2007). Under conditions where Rubisco LSU protein and D1 protein of the wild type increased in response to Brz treatment in the light, no induction of these chloroplast proteins was observed in clpB3 and clpC1 mutants (FIG. 13a). The results thus suggest that ClpB3 and ClpC1 might be new members of the group of chloroplast protein regulatory factors involved in BR signaling. Chloroplast protein regulation by BR might be controlled, not only by BPG2, but a number of other players. Nevertheless, the lower chloroplast protein accumulation in the bpg2 mutant (FIG. 10) and the higher induction of BPG2 gene expression by Brz in comparison with ClpB3 and ClpC1 (Supplement FIG. 13b) suggests that BPG2 plays an especially important role for chloroplast protein regulation in BR signal transduction.

High Accumulation of Chloroplast Proteins in bpg2 Highly Expressing Transformed Lines.

In bpg2, the abnormal ribosomes with un-spliced rRNA could limit the rate of translation, and repeated translational delay might cause the larger reduction of protein accumulation that is observed in these mutants. In the contrast to knock-out mutants of BPG2, we tried to make and grow BPG2 overexpressed transformants (FIGS. 14-17). These results suggest that BPG2 regulates proceeding of chloroplast rRNA splicing, and then, accelerated splicing of chloroplast rRNA in the BPG2-overexpressed transformants might cause the higher translation of chloroplast genome encoded D1 protein. Furthermore, nuclear genome encoded Rubisco SSU protein and LHCP accumulation levels in BPG2-OX transformants were also increased. The genes encoding Rubisco SSU and LHCP proteins are transcribed and translated in nucleus and not in chloroplast. These accumulation could not effected chloroplast rRNA directly. BPG2 protein also possessed GTP binding domain that domain are involved in protein folding in some cases of animals and plants. BPG2 protein might have the more general functions for protein folding regulatory mechanism. In that case, BPG2 regulation to chloroplast rRNA might not be direct binding to rRNA splicing, but regulation of folding or stabilization of splicing enzyme to chloroplast rRNA.

BPG2 as a novel regulator of chloroplast rRNA processing

The BPG2 gene encoded a putative 660-amino-acid sequence (FIG. 2d). A further search showed that BPG2 homologous are found in Gram-positive bacteria, such as *L. monocytogenes*, *L. lactis*, and *B. subtilis* (FIG. 2c). *B. subtilis* YqeH were recently characterized (Uicker et al., 2007; Loh et al., 2007) and found to possess a highly conserved zinc finger motif (a sequence beginning with $CXXCX_n$ and ending with CXXC) that has previously been found in ribosomal proteins and may participate in protein-RNA interaction (Anand et al., 2006; Uicker et al., 2007). *Arabidopsis* BPG2 has a putative zinc finger motif and GTP-binding domains that are similar to YqeH (FIG. 2d). We constructed a mutated cDNA of BPG2 that conserved the amino acids of the zinc finger motif and four GTP-binding domains by replacement with alanine, and transformed the bpg2-1 mutant with the BPG2 mutated cDNA (FIG. 4a). All six transformants showed a pale green phenotype (FIG. 4b-g, m, n), which could not be rescued by the mutated BPG2. These results suggested that the zinc finger motif and GTP-binding domains are necessary for BPG2 function and possibly regulate chloroplast biogenesis.

In this report, we showed the accumulation of pre-16S rRNA and pre-23S rRNA in bpg2 mutants (FIG. 8). In *Arabidopsis*, factors related to chloroplast rRNA processing have been isolated. An *Arabidopsis* mutant rnr1 that is deleted in exoribonuclease showed accumulation of pre-16S, pre-23S, and pre-4.5S rRNA (Kishine et al., 2004; Bollenbach et al., 2005). Processed 23S rRNA at hidden breaks of 1.2-, 1.0-, and 0.5-kb was decreased in rnr1. In contrast to rnr1, these transcripts were accumulated in bpg2 mutants at similar levels to the wild type (FIG. 8b, c). The *Arabidopsis* dal1 mutant accumulated pre-16SrRNA and pre-23S-4.5S rRNA dicistronic processing intermediates (Bisanz et al., 2003). In dal1, expression of CAB and rbcL decreased in comparison to the wild type. Unlike dal1, expression of CAB and rbcL in bpg2 mutants did not differ from the wild type (FIG. 7a, b). As described previously, B. subtilis YqeH is homologous to BPG2, and YqeH-depleted cells accumulate pre-16S rRNA (Uicker et al., 2007; Loh et al., 2007). Between B. subtilis YqeH and *Arabidopsis* BPG2, GTP binding domains G4-G1-G2-G3 are highly conserved (FIG. 2d). YqeH is a member of the Era/Obg family, which is involved in assembly of ribosomal subunits (Matsuo et al., 2007). In *Arabidopsis*, at least one homolog to YqeH has been identified, under three different gene names (RIF/NOS/NOA), and the knock-out phenotype was observed as pale green leaves. From analysis of rif mutants, it appears that RIF1 protein is involved in posttranscriptional upregulation of isoprenoid biosynthesis proteins in chloroplasts (Flores-Pérez et al., 2008). NOS protein was found to bind specifically to GTP and had GTP hydrolysis activity (Moreau at al., 2008). A chimeric YqeH comprising the transit peptide of AtNOA1 and bacterial GsYqeH of Geobacillus complemented the pale green phenotype of Atnoa1 mutant. From these analyses, it is not possible to establish whether RIF1, NOS1 and NOA1 are involved in both regulation of the chloroplast ribosome as well as regulation of chloroplast rRNA. However, our studies suggest that the BPG2 protein has a novel function in regulating chloroplastic 16S and 23S rRNA maturation and these results had not been analyzed using plant YqeH homologous protein yet. The relationship between BPG2 function and ribosomal regulation promises to be very interesting, and these analyses will clarify the molecular mechanism of chloroplast protein synthesis in the future.

A homologous gene of BPG2 and RIF/NOS/NOA, At4g10620, has also been identified and the GTP binding domains G4-G1-G2-G3 are conserved in the three genes (FIG. 2c and d). From hydropathicity plot analysis, N-terminal hydrophobic amino acid sequences in BPG2 and RIF/NOS/NOA were identified that were predicted to be chloroplast transit peptides. By contrast, an N-terminal sequence of At4g10620 protein was predicted to be hydrophilic, indicating that At4g10620 protein is not transported into the chloroplast. This suggests that, from the aspect of functional homology, BPG2 might be closer to RIF/NOS/NOA than At4g10620.

BLAST searches with the BPG2 amino acid sequence revealed that BPG2 homologous genes are widespread in dicot and monocot plants, including *Arabidopsis*, rice, medicago, and grape (FIG. 2c, d). BPG2 homologs are also present in the green algae O. lucimarinus and C. reinhardtii, and Gram-positive bacteria, such as L. monocytogenes, L. lactis, and B. subtilis (FIG. 2c). These results suggest that the BPG2 homologous gene family might have been conserved during evolution, before symbiosis of ancestral green algae into higher plants. rRNA fragmentation and processing has been found widely and extensively researched in bacteria, though the enzymatic machinery has not yet been elucidated. The evolutional conservation of BPG2 with the proteins of many plant organelles and bacteria can be used to elucidate mechanisms of rRNA processing and translational regulation.

REFERENCES

Anand, B., Verma, S. K. and Prakash, B. (2006) Structural stabilization of GTP-binding domains in circularly permuted GTPase: implications for RNA binding. Nucleic Acids Res., 34, 2196-2205.

Arnon, D. I. (1949) Copper enzymes in isolated chloroplasts polyphenoloxidase in Beta vulgaris. Plant Physiol., 24, 1-15.

Asami, T., Min, Y. K., Nagata, N., Yamagishi, K., Takatsuto, S., Fujioka, S., Murofushi, N., Yamaguchi, I. and Yoshida, S. (2000) Characterization of brassinazole, a triazole-type brassinosteroid biosynthesis inhibitor. Plant Physiol., 123, 93-99.

Asami, T., Mizutani, M., Fujioka, S., Goda, H., Min, Y. K., Shimada, Y., Nakano, T., Takatsuto, S., Matsuyama, T., Nagata, N., Sakata, K. and Yoshida, S. (2001) Selective interaction of triazole derivatives with DWF4, a cytochrome P450 monooxygenase of the brassinosteroid biosynthetic pathway, correlates with brassinosteroid deficiency in Planta. J. Biol. Chem., 276, 25687-25691.

Asami, T., Nakano, T., Nakashita, H., Sekimata, K., Shimada, Y. and Yoshida, S. (2003) The influence of chemical genetics on plant science: Shedding light on functions and mechanism of action of brassinosteroids using biosynthesis Inhibitors. J. Plant Growth Regul., 22, 336-349.

Asami, T. and Yoshida, S. (1999) Brassinosteroid biosynthesis inhibitors. Trends Plant Sci., 4, 348-353.

Azpiroz, R., Wu, Y., LoCascio, C. and Feldmann, K. A. (1998) An *Arabidopsis* brassinosteroid-dependent mutant is blocked in cell elongation. Plant Cell, 10, 219-230.

Bajguz, A. and Tretyn, A. (2003) The chemical characteristic and distribution of brassinosteroids in plants. Phytochem., 62, 1027-1046.

Bisanz, C., Bégot, L., Carol, P., Perez, P., Bligny, M., Pesey, H., Gallois, J. L., Lerbs-Mache, S. and Mache, R. (2003) The *Arabidopsis* nuclear DAL gene encodes a chloroplast protein which is required for the maturation of the plastid ribosomal RNAs and is essential for chloroplast differentiation. Plant Mol. Biol., 51, 651-663.

Bollenbach, T. J., Lange, H., Gutierrez, R., Erhardt, M., Stern, D. B. and Gagliardi, D. (2005) RNR1, a 3'-5' exoribonuclease belonging to the RNR superfamily, catalyzes 3' maturation of chloroplast ribosomal RNAs in *Arabidopsis thaliana*. Nucleic Acids Res., 33, 2751-2763.

Cheng, Z. F. and Deutscher, M. P. (2003) Quality control of ribosomal RNA mediated by polynucleotide phosphorylase and RNase R. Proc. Natl Acad. Sci. USA, 100, 6388-6393.

Choe, S., Dilkes, B. P., Fujioka, S., Takatsuto, S., Sakurai, A. and Feldmann, K. A. (1998) The DWF4 gene of *Arabidopsis* encodes a cytochrome P450 that mediates multiple 22a-hydroxylation steps in brassinosteroid biosynthesis. Plant Cell, 10, 231-243.

Chory, J., Nagpal, P. and Peto, C. A. (1991) Phenotypic and genetic analysis of det2, a new mutant that affects light-regulated seedling development in *Arabidopsis*. Plant Cell, 3, 445-459.

Clouse, S. D., Langford, M. and McMorris, T. C. (1996) A brassinosteroid-insensitive mutant in *Arabidopsis thaliana* exhibits multiple defects in growth and development. Plant Physiol., 111, 671-678.

Evguenieva-Hackenberg, E. (2005) Bacterial ribosomal RNA in pieces. Mol. Microbiol., 57, 318-325.

Flores-Pérez, Ú., Sauret-Güeto, S., Gas, E., Jarvis, P. and Rodríguez-Concepción, M. (2008) A mutant impaired in the production of plastome-encoded proteins uncovers a mechanism for the homeostasis of isoprenoid biosynthetic enzymes in *Arabidopsis* plastids. Plant Cell, 20, 1303-1315.

Fujioka, S., Li, J., Choi, Y., H., S., H., Takatsuto, S., Noguchi, T., Watanabe, T., Kuriyama, Y., Yokota, T., Chory, J. and Sakurai, A. (1997) The *Arabidopsis* deetiolated2 mutant is blocked early in brassinosteroid biosynthesis. Plant Cell, 9, 1951-1962.

Grove, M. D., Spencer, G. F., Rohwedder, W. K., Mandava, N., Worley, J. F. and Warhen, J. D. (1979) A unique plant growth promoting steroid from *Brassica napus* pollen. Nature, 281, 216-217.

He, J. X., Gendron, J. M., Sun, Y., Gampala, S. S. L., Gendron, N., Sun, C. Q. and Wang, Z. Y. (2005) BZR1 is a transcriptional repressor with dual roles in brassinosteroid homeostasis and growth responses. Science, 307, 534-538.

Higuchi, R., Krummel, B. and Saiki, R. K. (1988) A general method of in vitro preparation and specific mutagenesis of DNA fragment: study of protein and DNA interactions. Nucleic Acids Res., 16, 7351-7367.

Initiative, A. G. (2000) Analysis of genome of the flowering plant *Arabidopsis thaliana*. Nature, 408, 796-815.

Kennell, D. (2002) Processing endoribonucleases and mRNA degradation in bacteria. J. Bacteriol., 184, 4645-4657.

Kishine, M., Takabayashi, A., Munekage, Y., Shikanai, T., Endo, T. and Sato, F. (2004) Ribosomal RNA processing and an RNase R family member in chloroplasts of *Arabidopsis*. Plant Mol. Biol., 55, 595-606.

Leister, D. (2003) Chloroplast research in the genomic age. Trends Genetics, 19, 47-56.

Li, J., Biswas, M. G., Chao, A., Russell, D. W. and Chory, J. (1997) Conservation of function between mammalian and plant steroid 5a-reductase. Proc. Natl Acad. Sci. USA, 94, 3554-3559.

Li, J. and Chory, J. (1997) A putative leucine-rich repeat receptor kinase involved in brassinosteroid signal transduction. Cell, 90, 929-938.

Li, J. and Nam, K. H. (2002) Regulation of brassinosteroid signaling by a GSK3/SHAGGY-like kinase. Science, 295, 1299-1301.

Li, J., Nam, K. H., Vafeados, D. and Chory, J. (2001) BIN2, a new brassinosteriod-insensitive locus in *Arabidopsis*. Plant Physiol., 14-22.

Liu, Y. G., Mitsukawa, N., Oosumi, T. and Whittier, R. F. (1995) Effect isolation and mapping of *Arabidopsis thaliana* T-DNA insert junctions by thermal asymmetric interlaced PCR. Plant J., 8, 457-463.

Loh, P. C., Morimoto, T., Matsuo, Y., Oshima, T. and Ogasawara, N. (2007) The GTP-binding protein YqeH participates in biogenesis of the 30S ribosome subunit in *Bacillus subtilis*. Genes Genet. Syst., 82, 281-289.

Matsuo, Y., Ohshima, T., Loh, P. C., Morimoto, T. and Ogasawara, N. (2007) Isolation and characterization of a dominant negative mutant of *Bacillus subtilis* GTP-binding protein, YlqF, essential for biogenesis and maintenance of the 50S ribosomal subunit. J. Biol. Chem., 282, 25270-25277.

Moreau M, Lee G1, Wang Y, Crane B R, Klessig D F. (2008) AtNOS/AtNOA1 is a functional *Arabidopsis thaliana* cGTPase and not a nitric-oxide synthase. J Biol Chem., 283, 32957-32967.

Myouga F, Motohashi R, Kuromori T, Nagata N, Shinozaki K. (2006) An *Arabidopsis* chloroplast-targeted Hsp101 homologue, APG6, has an essential role in chloroplast development as well as heat-stress response. Plant J., 48, 249-260.

Nagata, N., Min, Y. K., Nakano, T., Asami, T. and Yoshida, S. (2000) Treatment of dark-grown *Arabidopsis thaliana* with a brassinosteroid-biosynthesis inhibitor, brassinazole, induces some characteristics of light-grown plants. Planta, 211, 781-790.

Nakagawa, T., Kurose, T., Hino, T., Tanaka, K., Kawamukai, M., Niwa, Y., Toyooka, K., Matsuoka, K., Jinbo, T. and Kimura, T. (2007) Development of series of gateway binary vectors, pGWBs, for realizing efficient construction of fusion genes for plant transformation. J. Biosci. Bioeng., 104, 34-41.

Nakagawara E, Sakuraba Y, Yamasato A, Tanaka R, Tanaka A. (2007) Clp protease controls chlorophyll b synthesis by regulating the level of chlorophyllide a oxygenase. Plant J., 49, 800-809.

Nakajima, Y., Yoshida, S., Inoue, Y. and Ono, T. (1996) Occupation of the $Q_B$-binding pocket by a photosystem II inhibitor triggers dark cleavage of the D1 protein subjected to brief preillumination. J. Biol. Chem., 271, 17383-17389.

Nakazawa, M., Ichikawa, T., Ishikawa, A., Kobayashi, H., Tsuhara, Y., Kawashima, M., Suzuki, K., Muto, S. and Matsui, M. (2003) Activation tagging, a novel tool to dissect the functions of a gene family. Plant J., 34, 741-750.

Strittmatter, G. and Kössel, H. (1984) Cotranscription and processing of 23S, 4.55 and 5S rRNA in chloroplasts from *Zea mays*. Nucleic Acids Res., 12, 7633-7647.

Sudhamsu J, Lee G I, Klessig D F, Crane B R. (2008) The structure of YqeH. An AtNOS1/AtNOA1 ortholog that couples GTP hydrolysis to molecular recognition. J Biol Chem., 283, 32968-32976.

Szekeres, M., Németh, K., Koncz-Kálman, A., Mathur, J., Kauschmann, A., Altmann, J., Rédei, G. P., Nagy, F., Schell, J. and Koncz, C. (1996) Brassinosteroid rescue the deficiency of CYP90, a cytochrome P450, controlling cell elongation and de-etiolation in *Arabidopsis*. Cell, 85, 171-182.

Uicker, W. C., Schaefer, L., Koenigsknecht, M. and Britton, M. A. (2007) The essential GTPase YqeH is required for proper ribosome assembly in *Bacillus subtilis*. J. Bacteriol., 189, 2926-2929.

Wang, Z. Y., Nakano, T., Gendron, J., He, J., Chen, M., Vafeados, D., Yang, Y., Fujioka, S., Yoshida, S., Asami, T. and Chory, J. (2002) Nuclear-localized BZR1 mediated brassinosteroid-induced growth and feedback suppression of brassinosteroid biosynthesis. Dev. Cell, 2, 505-513.

Yin, Y., Wang, Z. Y., Mora-Garcia, S., Li, J., Yoshida, S., Asami, T. and Chory, J. (2002) BES1 accumulates in the nucleus in response to brassinosteroid to regulate gene expression and promote stem elongation. Cell, 109, 181-191.

INDUSTRIAL APPLICABILITY

As described above, this invention provides transformed plants or algae with increased chlorophyll. In the plants or algae the ability of photosynthesis is more enhanced than wild type and so it is possible to facilitate growth of the plants or algae. The technique according to the invention would be very useful in the field of agriculture and forestry particularly.

Sequences:
BPG2 (A. thaliana):
SEQ ID NO: 1
(amino acid sequence)
MVVLISSTVTICNVKPKLEDGNFRVSRLIHRPEVPFFSGLSNEKKKKCAV

SVMCLAVKKEQVVQSVESVNGTIFPKKSKNLIMSEGRDEDEDYGKIICPG

CGIFMQDNDPDLPGYYQKRKVIANNLEGDEHVENDELAGFEMVDDDADEE

EEGEDDEMDDEIKNAIEGSNSESESGFEWESDEWEEKKEVNDVELDGFAP

AGVGYGNVTEEKEKKKRVSKTERKKIAREEAKKDNYDDVTVCARCHSLRN

YGQVKNQAAENLLPDFDFDRLISTRLIKPMSNSSTTVVVMVVDCVDFDGS

FPKRAAKSLFQVLQKAENDPKGSKNLPKLVLVATKVDLLPTQISPARLDR

WVRHRAKAGGAPKLSGVYMVSARKDIGVKNLLAYIKELAGPRGNVWVIGA

QNAGKSTLINALSKKDGAKVTRLTEAPVPGTTLGILKIGGILSAKAKMYD

TPGLLHPYLMSLRLNSEERKMVEIRKEVQPRSYRVKAGQSVHIGGLVRLD

LVSASVETIYITIWASHSVSLHLGKTENAEEIFKGHSGLRLQPPIGENRA

SELGTWEEKEIQVSGNSWDVKSIDISVAGLGWLSLGLKGAATLALWTYQG

IDVTLREPLVIDRAPYLERPGFWLPKAITEVLGTHSSKLVDARRRKKQQD

STDFLSDSVA

BPG2 (A. thaliana):
SEQ ID NO: 2
(nucleotide sequence)
atggtggttttgatttcaagtacagtgacgatttgcaatgttaaaccaa gcttgaagacggaaactttcgcgttagccggttgatacacagacccgagg ttccatttttctcaggattgagtaatgagaagaagaagaaatgtcagtt tcggttatgtgtttagctgtgaagaaagaacaagttgttcaaagcgtgga gagtgttaacgggacgattttttccgaagaaatcaaaaaatcttatcatga gcgaaggaagagatgaagatgaggactatgggaagattatttgtccaggt tgtgggattttttatgcaggacaatgatccagatttacccggatattatca gaagagaaaggtcattgcgaataacttggaaggtgatgaacatgtggaaa atgatgagcttgctgggtttgaaatggttgatgatgatgctgatgaggag gaggaagggaagatgatgaaatggatgatgagatcaagaatgcaataga aggtagcaactctgaaagtgagagtgggtttgaatgggaatcagatgagt gggaagaaaagaaggaagtgaatgatgttgaattggatggttttgctccg gctggtgttggatatggtaatgtcactgaggagaaggagaagaagaaacg ggtttccaaaacagagaggaagaagatagctagagaggaggcaaagaaag acaattatgatgatgtgactgtgtgtgctcgttgccattctctgaggaat tatggccaggtgaagaatcaggctgcagagaatctcttacccgattttga tttcgataggttgatctcaactagactgatcaaaccgatgagtaactcca gcactacagttgtagtcatggttgttgattgtgtagactttgatggttcg tttcccaaacgagctgccaagtctctgtttcaagtgcttcaaaaagctga aaatgatcctaagggtagcaaaaacctcccaaaacttgtacttgttgcaa caaaagtagacttacttcctacacagatttcaccagctcggttagaccga tgggtgcgccaccgtgccaaggctggaggagcacctaagctaagtgggt ttatatggttagtgctcgcaaagatattggtgttaagaatctgttagctt acattaaagagttggctggtccaagaggaaatgtgtgggttattggagct cagaacgcggggaaatctactttgattaatgccttatccaagaaagatgg tgcaaaggtcacgaggctcacggaagctccagttcctggaacaactcttg gaatattgaaaattggcggaatattgtctgcaaaggctaagatgtatgac actcccggccttttgcatccctaccttatgtccctgagattgaattcaga ggagcgaaaatggtagagataaggaaggaagttcaacctcggagttaca gagtcaaggcaggacagtctgttcacattggtggcctggtcaggctagac ctcgttctgcttcagttgaaacaatatacattacaatatgggcatcaca tagtgtttcattgcatctaggaaaaacagagaatgccgaagaaatattca agggccattccggtttacgccttcagccaccaattggagagaacagagcg tctgaattgggaacatgggaagagaaggagattcaggtgtcgggaaatag ctgggacgtgaaaagcatagacatttcagtggctggtcttggctggttat ccctgggcctcaaaggtgcagcaacactagcattgtggacttatcagggg attgatgtaaccttgagagaaccattggttattgaccgcgcaccatatct tgagcggcctggcttctggttgccaaaagccatcaccgaagtgcttggaa cacattctagtaagcttgttgatgctcgtaggaggaagaagcaacaagac agcacagattttctctctgatagtgttgcttagtataacctgtatcgact tattattagctttcatcagtgtagtcattttggaaagtttatattggttt atgtatttaaaacaattttaaatccacatcgac All publications and patent applications mentioned in this specification are herein incorporated by reference.

Other embodiments are within the following claims.

What is claimed is:

1. A transformed plant or alga with increased chlorophyll, comprising an overexpressed foreign DNA which codes for a chloroplast protein BPG2, wherein the BPG2 comprises the amino acid sequence as shown in SEQ ID NO:1, or an amino acid sequence having an at least 50% identity to the amino acid sequence of SEQ ID NO:1 and having a zinc finger motif and GTP-binding domains having a G4-G1-G2-G3 motif, and having an activity of increasing a level of chlorophyll when compared with wild type.

2. The transformed plant or alga of claim 1, wherein the DNA comprises: (i) a nucleotide sequence as shown in SEQ ID NO:2, or a nucleotide sequence having an at least 50% identity to the nucleotide sequence of SEQ ID NO:2; (ii) a nucleotide sequence encoding the chloroplast protein BPG2, wherein the BPG2 comprises the amino acid sequence as shown in SEQ ID NO:1, or an amino acid sequence having an at least 50% identity to the amino acid sequence of SEQ ID NO:1 and having a zinc finger motif and GTP-binding domains having a G4-G1-G2-G3 motif, and having an activity of increasing a level of chlorophyll when compared with wild type; or (iii) a nucleotide sequence capable of hybridizing with a nucleotide sequence complement to the nucleotide sequence of SEQ ID NO:2 under stringent conditions, wherein the nucleotide sequence (i), (ii) or (iii) codes for a protein having an activity of increasing a level of chlorophyll when compared with wild type, and wherein the stringent conditions comprise hybridization at approximately 42-55° C. in approximately 2-6×SSC, followed by wash at approximately 50-65° C. in approximately 0.1-1×SSC containing approximately 0.1-0.2% SDS, where 1×SSC is a solution containing 0.15 M NaCl and 0.015 M Na citrate, pH 7.0.

3. The transformed plant or alga of claim 1, having an increased accumulation of the RuBisCo small subunit protein or analog thereof which is a key protein for fixation of carbon dioxide in the photosynthesis.

4. The transformed plant or alga of claim 1, having an increased accumulation of protein D1 or analog thereof involved in the photosystem II of photosynthesis.

5. The transformed plant or alga of claim 1, having an increased accumulation of a light harvesting complex chlorophyll binding protein.

6. The transformed plant or alga of claim 1, having an increased activity of photosynthesis in the presence of light and brassinazole.

7. Progeny of the transformed plant or alga of claim 1, wherein the progeny has an increased level of chlorophyll and comprises an overexpressed foreign DNA which codes for a chloroplast protein BPG2, wherein the BPG2 comprises the amino acid sequence as shown in SEQ ID NO:1, or an amino acid sequence having an at least 50% identity to the amino acid sequence of SEQ ID NO:1 and having a zinc finger motif and GTP-binding domains having a G4-G1-G2-G3 motif, and having an activity of increasing a level of chlorophyll when compared with wild type.

8. A cell, tissue, organ, or seed from the transformed plant or alga of claim 1,wherein the cell, tissue, organ, or seed comprises a foreign DNA which codes for a chloroplast protein BPG2, wherein the BPG2 comprises the amino acid sequence as shown in SEQ ID NO:1, or an amino acid sequence having an at least 50% identity to the amino acid sequence of SEQ ID NO:1 and having a zinc finger motif and GTP-binding domains having a G4-G1-G2-G3 motif, and having an activity of increasing a level of chlorophyll when compared with wild type.

9. A cell, tissue, organ, or seed from the progeny of claim 7,wherein the cell, tissue, organ, or seed comprises a foreign DNA which codes for a chloroplast protein BPG2, wherein the BPG2comprises the amino acid sequence as shown in SEQ ID NO:1, or an amino acid sequence having an at least 50% identity to the amino acid sequence of SEQ ID NO:1 and having a zinc finger motif and GTP-binding domains having a G4-G1-G2-G3 motif, and having an activity of increasing a level of chlorophyll when compared with wild type.

10. A method for producing a transformed plant of claim 1, comprising the following steps of:
   (1) introducing a vector comprising the DNA as defined in claim 1 or 2 into cells of a plant to obtain transformed cells;
   (2) selecting a transformed cell overexpressing the DNA, from the transformed cells of step (1); and
   (3) generating the transformed plant from the transformed cell of step (2).

11. A method for producing a transformed plant of claim 1, comprising the following steps of:
   (1) introducing a vector comprising the DNA as defined in claim 2 into cells of a plant to obtain transformed cells;
   (2) selecting a transformed cell overexpressing the DNA, from the transformed cells of step (1); and
   (3) generating the transformed plant from the transformed cell of step (2).

12. A method for producing a transformed alga of claim 1, comprising introducing a vector comprising the DNA as defined in claim 1 into cells of an alga to obtain transformed cells, and selecting a transformed cell overexpressing the DNA, from the obtained transformed cells.

13. A method for producing a transformed alga of claim 1, comprising introducing a vector comprising the DNA as defined in claim 2 into cells of an alga to obtain transformed cells, and selecting a transformed cell overexpressing the DNA, from the obtained transformed cells.

14. The transformed plant or alga of claim 1, wherein BPG2 comprises the amino acid sequence as shown in SEQ ID NO:1.

15. The transformed plant or alga of claim 1, wherein BPG2 comprises an amino acid sequence having an at least 50% identity to the amino acid sequence of SEQ ID NO:1 and having a zinc finger motif and GTP-binding domains having a G4-G1-G2-G3 motif.

16. The progeny of claim 7, wherein BPG2 comprises the amino acid sequence as shown in SEQ ID NO:1.

17. The progeny of claim 7, wherein BPG2 comprises an amino acid sequence having an at least 50% identity to the amino acid sequence of SEQ ID NO:1 and having a zinc finger motif and GTP-binding domains having a G4-G1-G2-G3 motif.

18. The cell, tissue, organ, or seed of claim 8, wherein BPG2 comprises the amino acid sequence as shown in SEQ ID NO:1.

19. The cell, tissue, organ, or seed of claim 8, wherein BPG2 comprises an amino acid sequence having an at least 50% identity to the amino acid sequence of SEQ ID NO:1 and having a zinc finger motif and GTP-binding domains having a G4-G1-G2-G3 motif.

20. The cell, tissue, organ, or seed from the progeny of claim 9, wherein BPG2 comprises the amino acid sequence as shown in SEQ ID NO:1.

21. The cell, tissue, organ, or seed from the progeny of claim 9, wherein BPG2 comprises an amino acid sequence having an at least 50% identity to the amino acid sequence of SEQ ID NO:1 and having a zinc finger motif and GTP-binding domains having a G4-G1-G2-G3 motif.

22. The method of claim 10, wherein said transformed plant expresses BPG2 comprising the amino acid sequence as shown in SEQ ID NO:1.

23. The method of claim 10, wherein said transformed plant expresses an amino acid sequence having an at least 50% identity to the amino acid sequence of SEQ ID NO:1 and having a zinc finger motif and GTP-binding domains having a G4-G1-G2-G3 motif.

* * * * *

SEQUENCE LISTING

<160> NUMBER OF SEQ ID NOS: 37

<210> SEQ ID NO 1
<211> LENGTH: 660
<212> TYPE: PRT
<213> ORGANISM: Arabidopsis thaliana -continued

<400> SEQUENCE: 1

```
Met Val Val Leu Ile Ser Ser Thr Val Thr Ile Cys Asn Val Lys Pro
1               5                   10                  15

Lys Leu Glu Asp Gly Asn Phe Arg Val Ser Arg Leu Ile His Arg Pro
            20                  25                  30

Glu Val Pro Phe Phe Ser Gly Leu Ser Asn Glu Lys Lys Lys Lys Cys
        35                  40                  45

Ala Val Ser Val Met Cys Leu Ala Val Lys Lys Glu Gln Val Val Gln
    50                  55                  60

Ser Val Glu Ser Val Asn Gly Thr Ile Phe Pro Lys Lys Ser Lys Asn
65                  70                  75                  80

Leu Ile Met Ser Glu Gly Arg Asp Glu Asp Glu Asp Tyr Gly Lys Ile
                85                  90                  95

Ile Cys Pro Gly Cys Gly Ile Phe Met Gln Asp Asn Asp Pro Asp Leu
            100                 105                 110

Pro Gly Tyr Tyr Gln Lys Arg Lys Val Ile Ala Asn Asn Leu Glu Gly
        115                 120                 125

Asp Glu His Val Glu Asn Asp Glu Leu Ala Gly Phe Glu Met Val Asp
    130                 135                 140

Asp Asp Ala Asp Glu Glu Glu Gly Glu Asp Glu Met Asp Asp
145                 150                 155                 160

Glu Ile Lys Asn Ala Ile Glu Gly Ser Asn Ser Glu Ser Glu Ser Gly
                165                 170                 175

Phe Glu Trp Glu Ser Asp Glu Trp Glu Glu Lys Lys Glu Val Asn Asp
            180                 185                 190

Val Glu Leu Asp Gly Phe Ala Pro Ala Gly Val Gly Tyr Gly Asn Val
        195                 200                 205

Thr Glu Glu Lys Glu Lys Lys Arg Val Ser Lys Thr Glu Arg Lys
    210                 215                 220

Lys Ile Ala Arg Glu Glu Ala Lys Lys Asp Asn Tyr Asp Asp Val Thr
225                 230                 235                 240

Val Cys Ala Arg Cys His Ser Leu Arg Asn Tyr Gly Gln Val Lys Asn
                245                 250                 255

Gln Ala Ala Glu Asn Leu Leu Pro Asp Phe Asp Phe Asp Arg Leu Ile
            260                 265                 270

Ser Thr Arg Leu Ile Lys Pro Met Ser Asn Ser Ser Thr Thr Val Val
        275                 280                 285

Val Met Val Val Asp Cys Val Asp Phe Asp Gly Ser Phe Pro Lys Arg
    290                 295                 300

Ala Ala Lys Ser Leu Phe Gln Val Leu Gln Lys Ala Glu Asn Asp Pro
305                 310                 315                 320

Lys Gly Ser Lys Asn Leu Pro Lys Leu Val Leu Val Ala Thr Lys Val
                325                 330                 335

Asp Leu Leu Pro Thr Gln Ile Ser Pro Ala Arg Leu Asp Arg Trp Val
            340                 345                 350

Arg His Arg Ala Lys Ala Gly Gly Ala Pro Lys Leu Ser Gly Val Tyr
        355                 360                 365

Met Val Ser Ala Arg Lys Asp Ile Gly Val Lys Asn Leu Leu Ala Tyr
    370                 375                 380

Ile Lys Glu Leu Ala Gly Pro Arg Gly Asn Val Trp Val Ile Gly Ala
385                 390                 395                 400

Gln Asn Ala Gly Lys Ser Thr Leu Ile Asn Ala Leu Ser Lys Lys Asp
                405                 410                 415
```

```
Gly Ala Lys Val Thr Arg Leu Thr Glu Ala Pro Val Pro Gly Thr Thr
                420                 425                 430
Leu Gly Ile Leu Lys Ile Gly Ile Leu Ser Ala Lys Ala Lys Met
            435                 440                 445
Tyr Asp Thr Pro Gly Leu Leu His Pro Tyr Leu Met Ser Leu Arg Leu
        450                 455                 460
Asn Ser Glu Glu Arg Lys Met Val Glu Ile Arg Lys Glu Val Gln Pro
465                 470                 475                 480
Arg Ser Tyr Arg Val Lys Ala Gly Gln Ser Val His Ile Gly Gly Leu
                485                 490                 495
Val Arg Leu Asp Leu Val Ser Ala Ser Val Glu Thr Ile Tyr Ile Thr
            500                 505                 510
Ile Trp Ala Ser His Ser Val Ser Leu His Leu Gly Lys Thr Glu Asn
        515                 520                 525
Ala Glu Glu Ile Phe Lys Gly His Ser Gly Leu Arg Leu Gln Pro Pro
    530                 535                 540
Ile Gly Glu Asn Arg Ala Ser Glu Leu Gly Thr Trp Glu Glu Lys Glu
545                 550                 555                 560
Ile Gln Val Ser Gly Asn Ser Trp Asp Val Lys Ser Ile Asp Ile Ser
                565                 570                 575
Val Ala Gly Leu Gly Trp Leu Ser Leu Gly Leu Lys Gly Ala Ala Thr
            580                 585                 590
Leu Ala Leu Trp Thr Tyr Gln Gly Ile Asp Val Thr Leu Arg Glu Pro
        595                 600                 605
Leu Val Ile Asp Arg Ala Pro Tyr Leu Glu Arg Pro Gly Phe Trp Leu
    610                 615                 620
Pro Lys Ala Ile Thr Glu Val Leu Gly Thr His Ser Ser Lys Leu Val
625                 630                 635                 640
Asp Ala Arg Arg Arg Lys Lys Gln Gln Asp Ser Thr Asp Phe Leu Ser
                645                 650                 655
Asp Ser Val Ala
        660

<210> SEQ ID NO 2
<211> LENGTH: 2084
<212> TYPE: DNA
<213> ORGANISM: Arabidopsis thaliana

<400> SEQUENCE: 2
atggtggttt tgatttcaag tacagtgacg atttgcaatg ttaaaccaaa gcttgaagac    60
ggaaactttc gcgttagccg gttgatacac agacccgagg ttccattttt ctcaggattg   120
agtaatgaga agaagaagaa atgtgcagtt tcggttatgt gtttagctgt gaagaaagaa   180
caagttgttc aaagcgtgga gagtgttaac gggacgattt ttccgaagaa atcaaaaaat   240
cttatcatga gcgaaggaag agatgaagat gaggactatg gaagattat ttgtccaggt   300 tgtgggattt ttatgcagga caatgatcca gatttacccg gatattatca gaagagaaag   360
gtcattgcga taacttgga aggtgatgaa catgtggaaa atgatgagct tgctgggttt   420
gaaatggttg atgatgatgc tgatgaggag gaggaagggg aagatgatga aatggatgat   480
gagatcaaga atgcaataga aggtagcaac tctgaaagtg agagtgggtt tgaatgggaa   540
tcagatgagt gggaagaaaa gaaggaagtg aatgatgttg aattggatgg ttttgctccg   600
gctggtgttg atatggtaa tgtcactgag gagaaggaga agaagaaacg ggtttccaaa   660
acagagagga agaagatagc tagagaggag gcaaagaaag acaattatga tgatgtgact   720
```

```
gtgtgtgctc gttgccattc tctgaggaat tatggccagg tgaagaatca ggctgcagag      780
aatctcttac ccgattttga tttcgatagg ttgatctcaa ctagactgat caaaccgatg      840
agtaactcca gcactacagt tgtagtcatg gttgttgatt gtgtagactt tgatggttcg      900
tttcccaaac gagctgccaa gtctctgttt caagtgcttc aaaaagctga aaatgatcct      960
aagggtagca aaacctccc aaaacttgta cttgttgcaa caaaagtaga cttacttcct     1020
acacagattt caccagctcg gttagaccga tgggtgcgcc accgtgccaa ggctggagga     1080
gcacctaagc taagtggggt ttatatggtt agtgctcgca agatattgg tgttaagaat     1140 ctgttagctt acattaaaga gttggctggt ccaagaggaa atgtgtgggt tattggagct     1200
cagaacgcgg ggaaatctac tttgattaat gccttatcca agaaagatgg tgcaaaggtc     1260
acgaggctca cggaagctcc agttcctgga caaactcttg gaatattgaa aattggcgga     1320
atattgtctg caaaggctaa gatgtatgac actcccggcc ttttgcatcc ctaccttatg     1380
tccctgagat tgaattcaga ggagcggaaa atggtagaga taaggaagga agttcaacct     1440
cggagttaca gagtcaaggc aggacagtct gttcacattg gtggcctggt caggctagac     1500
ctcgtttctg cttcagttga acaatatac attacaatat gggcatcaca tagtgtttca     1560
ttgcatctag gaaaaacaga gaatgccgaa gaaatattca agggccattc cggtttacgc     1620
cttcagccac caattggaga gaacagagcg tctgaattgg gaacatggga agagaaggag     1680
attcaggtgt cgggaaatag ctgggacgtg aaaagcatag acatttcagt ggctggtctt     1740
ggctggttat ccctgggcct caaaggtgca gcaacactag cattgtggac ttatcagggg     1800
attgatgtaa ccttgagaga accattggtt attgaccgcg caccatatct tgagcggcct     1860
ggcttctggt tgccaaaagc catcaccgaa gtgcttggaa cacattctag taagcttgtt     1920
gatgctcgta ggaggaagaa gcaacaagac agcacagatt ttctctctga tagtgttgct     1980
tagtataacc tgtatcgact tattattagc tttcatcagt gtagtcattt tggaaagttt     2040
atattggttt atgtattta aaacaatttt aaatccacat cgac                      2084
```

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
tgcttgggtt gctacgtgaa                                                   20

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
acccaccatg cgtatcacct                                                   20

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
tccggaaggc aagtatgagg                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
tgcatcttcg gatctcgtca                                              20

<210> SEQ ID NO 7
<211> LENGTH: 22
<212> TYPE: DNA
<213> ORGANISM: Artificial Sequence
<220> FEATURE:
<223> OTHER INFORMATION: Synthetic Construct

<400> SEQUENCE: 7
cacgtcgaaa taaagatttc cg                                           22

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8
cctataaata cgacggatgc                                              20

<210> SEQ ID NO 9
<211> LENGTH: 21
<212> TYPE: DNA
<213> ORGANISM: Artificial Sequence
<220> FEATURE:
<223> OTHER INFORMATION: Synthetic Construct

<400> SEQUENCE: 9
ataataacgc tgcggacatc t                                            21

<210> SEQ ID NO 10
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 10
ngtcgaswga nawgaa                                                  16

<210> SEQ ID NO 11
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (9)..(9)

<223> OTHER INFORMATION: n is a, c, g, or t

<400> SEQUENCE: 11
sstggstana twatwct                                                  17

<210> SEQ ID NO 12
<211> LENGTH: 19
<212> TYPE: DNA
<213> ORGANISM: Artificial Sequence
<220> FEATURE:
<223> OTHER INFORMATION: Synthetic Construct

<400> SEQUENCE: 12
aagggccatt ccggtttac                                                19

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct

<400> SEQUENCE: 13
tcccagctat ttcccgacac                                               20

<210> SEQ ID NO 14
<211> LENGTH: 22
<212> TYPE: DNA
<213> ORGANISM: Artificial Sequence
<220> FEATURE:
<223> OTHER INFORMATION: Synthetic Construct

<400> SEQUENCE: 14
cctagatgca atgaaacact at                                            22

<210> SEQ ID NO 15
<211> LENGTH: 21
<212> TYPE: DNA
<213> ORGANISM: Artificial Sequence
<220> FEATURE:
<223> OTHER INFORMATION: Synthetic Construct

<400> SEQUENCE: 15
ggcggaatat tgtctgcaaa g                                             21

<210> SEQ ID NO 16
<211> LENGTH: 16
<212> TYPE: DNA
<213> ORGANISM: Artificial Sequence
<220> FEATURE:
<223> OTHER INFORMATION: Synthetic Construct

<400> SEQUENCE: 16
gccgcctcaa caatgg                                                   16

<210> SEQ ID NO 17
<211> LENGTH: 20
<212> TYPE: DNA
<213> ORGANISM: Artificial Sequence
<220> FEATURE:
<223> OTHER INFORMATION: Synthetic Construct

<400> SEQUENCE: 17
atggccaaaa tgctctgagc                                               20

<210> SEQ ID NO 18

```
<211> LENGTH: 20
<212> TYPE: DNA
<213> ORGANISM: Artificial Sequence
<220> FEATURE:
<223> OTHER INFORMATION: Synthetic Construct

<400> SEQUENCE: 18
acttccttca acacttgagc                                               20

<210> SEQ ID NO 19
<211> LENGTH: 22
<212> TYPE: DNA
<213> ORGANISM: Artificial Sequence
<220> FEATURE:
<223> OTHER INFORMATION: Synthetic Construct

<400> SEQUENCE: 19
attggctaag gaagttgact ac                                            22

<210> SEQ ID NO 20
<211> LENGTH: 29
<212> TYPE: DNA
<213> ORGANISM: Artificial Sequence
<220> FEATURE:
<223> OTHER INFORMATION: Synthetic Construct

<400> SEQUENCE: 20
ttcttggtca aaccatcggt tatcttaaa                                     29

<210> SEQ ID NO 21
<211> LENGTH: 26
<212> TYPE: DNA
<213> ORGANISM: Artificial Sequence
<220> FEATURE:
<223> OTHER INFORMATION: Synthetic Construct

<400> SEQUENCE: 21
tatgataagc agttcctggt agattt                                        26

<210> SEQ ID NO 22
<211> LENGTH: 18
<212> TYPE: DNA
<213> ORGANISM: Artificial Sequence
<220> FEATURE:
<223> OTHER INFORMATION: Synthetic Construct

<400> SEQUENCE: 22
cacgtcgccg tccagctc                                                 18

<210> SEQ ID NO 23
<211> LENGTH: 21
<212> TYPE: DNA
<213> ORGANISM: Artificial Sequence
<220> FEATURE:
<223> OTHER INFORMATION: Synthetic Construct

<400> SEQUENCE: 23
gtgaaggctg gatttgcagg a                                             21

<210> SEQ ID NO 24
<211> LENGTH: 21
<212> TYPE: DNA
<213> ORGANISM: Artificial Sequence
<220> FEATURE:
<223> OTHER INFORMATION: Synthetic Construct

<400> SEQUENCE: 24
```
aaccaccgat ccaggcactg t                                              21

<210> SEQ ID NO 25
<211> LENGTH: 20
<212> TYPE: DNA
<213> ORGANISM: Artificial Sequence
<220> FEATURE:
<223> OTHER INFORMATION: Synthetic Construct

<400> SEQUENCE: 25
cgcctctcta cccgatgatg                                                20

<210> SEQ ID NO 26
<211> LENGTH: 18
<212> TYPE: DNA
<213> ORGANISM: Artificial Sequence
<220> FEATURE:
<223> OTHER INFORMATION: Synthetic Construct

<400> SEQUENCE: 26
gcagcgacgg cgattgta                                                  18

<210> SEQ ID NO 27
<211> LENGTH: 19
<212> TYPE: DNA
<213> ORGANISM: Artificial Sequence
<220> FEATURE:
<223> OTHER INFORMATION: Synthetic Construct

<400> SEQUENCE: 27
cgccatccaa gctgttctc                                                 19

<210> SEQ ID NO 28
<211> LENGTH: 20
<212> TYPE: DNA
<213> ORGANISM: Artificial Sequence
<220> FEATURE:
<223> OTHER INFORMATION: Synthetic Construct

<400> SEQUENCE: 28
tcacgtccag caaggtcaag                                                20

<210> SEQ ID NO 29
<211> LENGTH: 19
<212> TYPE: DNA
<213> ORGANISM: Artificial Sequence
<220> FEATURE:
<223> OTHER INFORMATION: Synthetic Construct

<400> SEQUENCE: 29
aagggccatt ccggtttac                                                 19

<210> SEQ ID NO 30
<211> LENGTH: 20
<212> TYPE: DNA
<213> ORGANISM: Artificial Sequence
<220> FEATURE:
<223> OTHER INFORMATION: Synthetic Construct

<400> SEQUENCE: 30
tcccagctat ttcccgacac                                                20

<210> SEQ ID NO 31
<211> LENGTH: 22
<212> TYPE: DNA
<213> ORGANISM: Artificial Sequence
<220> FEATURE:

-continued

<223> OTHER INFORMATION: Synthetic Construct

<400> SEQUENCE: 31
cctagatgca atgaaacact at                                            22

<210> SEQ ID NO 32
<211> LENGTH: 597
<212> TYPE: PRT
<213> ORGANISM: Vitis vinifera

<400> SEQUENCE: 32

```
Met Arg Lys Asn Ser Arg Lys Asn Asp Ile Lys Phe Ser Phe Val Ala
1               5                   10                  15

Leu Ser Val Lys Ser Lys Tyr Thr Ile Gln Glu Thr Gln Lys Asn Asn
            20                  25                  30

Trp Lys Asn Pro Arg Lys Val Gly Asn Pro Ile Leu Ser Glu Gly
        35                  40                  45

Lys Asp Glu Asp Glu Ser Tyr Gly Gln Ile Cys Pro Gly Cys Gly Val
    50                  55                  60

Tyr Met Gln Asp Glu Asp Pro Asn Leu Pro Gly Tyr Tyr Gln Lys Arg
65                  70                  75                  80

Lys Leu Thr Leu Thr Glu Met Pro Glu Gly Gln Glu Asp Met Glu Gly
            85                  90                  95

Ser Asp Gly Glu Glu Ser Asn Leu Gly Thr Glu Asp Gly Asn Glu Phe
            100                 105                 110

Asp Trp Asp Ser Asp Glu Trp Glu Ser Glu Leu Glu Gly Glu Asp Asp
        115                 120                 125

Asp Leu Asp Leu Asp Gly Phe Ala Pro Ala Gly Val Gly Tyr Gly Asn
    130                 135                 140

Ile Thr Glu Glu Thr Ile Asn Lys Arg Lys Lys Arg Val Ser Lys
145                 150                 155                 160

Ser Glu Lys Lys Arg Met Ala Arg Glu Ala Lys Glu Arg Glu Glu
            165                 170                 175

Val Thr Val Cys Ala Arg Cys His Ser Leu Arg Asn Tyr Gly Gln Val
            180                 185                 190

Lys Asn Gln Met Ala Glu Asn Leu Ile Pro Asp Phe Asp Phe Asp Arg
        195                 200                 205

Leu Ile Ala Thr Arg Leu Met Lys Pro Thr Gly Thr Ala Asp Ala Thr
    210                 215                 220

Val Val Met Val Val Asp Cys Val Asp Phe Asp Gly Ser Phe Pro
225                 230                 235                 240

Lys Arg Ala Ala Lys Ser Leu Phe Lys Ala Leu Glu Gly Ser Arg Val
            245                 250                 255

Gly Ala Lys Val Ser Arg Lys Leu Pro Lys Leu Val Leu Val Ala Thr
            260                 265                 270

Lys Val Asp Leu Leu Pro Thr Gln Ile Ser Pro Ala Arg Leu Asp Arg
    275                 280                 285

Trp Val Arg His Arg Ala Lys Ala Gly Gly Ala Pro Lys Leu Ser Gly
        290                 295                 300

Val Tyr Met Val Ser Ala Arg Lys Asp Leu Gly Val Arg Asn Leu Leu
305                 310                 315                 320

Ser Phe Ile Lys Glu Leu Ala Gly Pro Arg Gly Asn Val Trp Val Ile
            325                 330                 335

Gly Ser Gln Asn Ala Gly Lys Ser Thr Leu Ile Asn Thr Phe Ala Lys
            340                 345                 350
```

```
Arg Glu Gly Val Lys Leu Thr Lys Leu Thr Glu Ala Ala Val Pro Gly
            355                 360                 365

Thr Thr Leu Gly Ile Leu Arg Ile Gly Ile Leu Ser Ala Lys Ala
    370                 375                 380

Lys Met Tyr Asp Thr Pro Gly Leu Leu His Pro Tyr Leu Met Ser Met
385                 390                 395                 400

Arg Leu Asn Arg Asp Glu Gln Lys Met Ala Glu Ile Arg Lys Glu Leu
                405                 410                 415

Gln Pro Arg Thr Tyr Arg Met Lys Ala Gly Gln Ala Val His Val Gly
            420                 425                 430

Gly Leu Met Arg Leu Asp Leu Asn Gln Ala Ser Val Glu Thr Ile Tyr
            435                 440                 445

Val Thr Ile Trp Ala Ser Pro Asn Val Ser Leu His Met Gly Lys Ile
    450                 455                 460

Glu Asn Ala Asp Glu Ile Trp Arg Lys His Val Gly Val Arg Leu Gln
465                 470                 475                 480

Pro Pro Val Arg Val Asp Arg Val Ser Glu Ile Gly Lys Trp Glu Glu
                485                 490                 495

Gln Glu Ile Lys Val Ser Gly Ala Ser Trp Asp Val Asn Ser Ile Asp
            500                 505                 510

Ile Ala Val Ala Gly Leu Gly Trp Phe Ser Leu Gly Leu Lys Gly Glu
    515                 520                 525

Ala Thr Leu Ala Leu Trp Thr Tyr Asp Gly Ile Glu Val Ile Leu Arg
530                 535                 540

Glu Pro Leu Val Leu Asp Arg Ala Pro Phe Leu Glu Arg Pro Gly Phe
545                 550                 555                 560

Trp Leu Pro Lys Ala Ile Ser Asp Ala Ile Gly Asn Gln Ser Lys Leu
                565                 570                 575

Glu Ala Glu Ala Arg Lys Arg Asp Gln Glu Ser Thr Lys Ser Leu
            580                 585                 590

Ser Glu Met Ser Thr
            595

<210> SEQ ID NO 33
<211> LENGTH: 616
<212> TYPE: PRT
<213> ORGANISM: Medicago truncatula

<400> SEQUENCE: 33

Met Ala Ile Leu Phe Ser Thr Ile Ala Leu Pro Ser Thr Asn Val Thr
1               5                   10                  15

Ser Lys Leu Ser Ile Leu Asn Asn Thr Ser His Ser His Ala Leu Arg
            20                  25                  30

His Phe Ser Gly Asn Thr Thr Lys Arg Phe His Lys Ala Ser Ser Phe
        35                  40                  45

Ile Ala Phe Ala Val Lys Asn Asn Pro Thr Ile Arg Lys Thr Thr Pro
    50                  55                  60

Arg Arg Asp Ser Arg Asn Pro Leu Leu Ser Glu Gly Arg Asp Glu Asp
65                  70                  75                  80

Glu Ala Leu Gly Pro Ile Cys Pro Gly Cys Gly Ile Phe Met Gln Asp
                85                  90                  95

Asn Asp Pro Asn Leu Pro Gly Phe Tyr Gln Gln Lys Glu Val Lys Ile
            100                 105                 110

Glu Thr Phe Ser Glu Glu Asp Tyr Glu Leu Asp Asp Glu Glu Asp Asp
        115                 120                 125
```

-continued

```
Gly Glu Glu Glu Asp Asn Gly Ser Ile Asp Asp Glu Ser Asp Trp Asp
        130                 135                 140

Ser Glu Glu Leu Glu Ala Met Leu Leu Gly Glu Asn Asp Asp Lys
145                 150                 155                 160

Val Asp Leu Asp Gly Phe Thr His Ala Gly Val Gly Tyr Gly Asn Val
                165                 170                 175

Thr Glu Glu Val Leu Glu Arg Ala Lys Lys Lys Val Ser Lys Ala
                180                 185                 190

Glu Lys Lys Arg Met Ala Arg Glu Ala Glu Lys Val Lys Glu Val
            195                 200                 205

Thr Val Cys Ala Arg Cys His Ser Leu Arg Asn Tyr Gly Gln Val Lys
210                 215                 220

Asn Tyr Met Ala Glu Asn Leu Ile Pro Asp Phe Asp Phe Asp Arg Leu
225                 230                 235                 240

Ile Thr Thr Arg Leu Met Asn Pro Ala Gly Ser Gly Ser Ser Thr Val
                245                 250                 255

Val Val Met Val Val Asp Cys Val Asp Phe Asp Gly Ser Phe Pro Arg
            260                 265                 270

Thr Ala Val Lys Ser Leu Phe Lys Ala Leu Glu Gly Met Gln Glu Asn
            275                 280                 285

Thr Lys Lys Gly Lys Lys Leu Pro Lys Leu Val Leu Ala Thr Lys
    290                 295                 300

Val Asp Leu Leu Pro Ser Gln Val Ser Pro Thr Arg Leu Asp Arg Trp
305                 310                 315                 320

Val Arg His Arg Ala Ser Ala Gly Gly Ala Pro Lys Leu Ser Ala Val
                325                 330                 335

Tyr Leu Val Ser Ser Arg Lys Asp Leu Gly Val Arg Asn Val Leu Ser
            340                 345                 350

Phe Val Lys Asp Leu Ala Gly Pro Arg Gly Asn Val Trp Val Ile Gly
            355                 360                 365

Ala Gln Asn Ala Gly Lys Ser Thr Leu Ile Asn Ala Phe Ala Lys Lys
            370                 375                 380

Glu Gly Ala Lys Val Thr Lys Leu Thr Glu Ala Pro Val Pro Gly Thr
385                 390                 395                 400

Thr Leu Gly Ile Leu Arg Ile Ala Gly Ile Leu Ser Ala Lys Ala Lys
                405                 410                 415

Met Phe Asp Thr Pro Gly Leu Leu His Pro Tyr Leu Leu Ser Met Arg
                420                 425                 430

Leu Asn Arg Glu Glu Gln Lys Met Ala Gly Gln Ala Ile His Val Gly
            435                 440                 445

Gly Leu Ala Arg Leu Asp Leu Ile Glu Ala Ser Val Gln Thr Met Tyr
    450                 455                 460

Val Thr Val Trp Ala Ser Pro Asn Val Ser Leu His Met Gly Lys Ile
465                 470                 475                 480

Glu Asn Ala Asn Glu Ile Trp Asn Asn His Val Gly Val Arg Leu Gln
                485                 490                 495

Pro Pro Ile Gly Asn Asp Arg Ala Ala Glu Leu Gly Thr Trp Lys Glu
            500                 505                 510

Arg Glu Val Lys Val Ser Gly Ser Ser Trp Asp Val Asn Cys Met Asp
            515                 520                 525

Val Ser Ile Ala Gly Leu Gly Trp Phe Ser Leu Gly Ile Gln Gly Glu
    530                 535                 540

Ala Thr Met Lys Leu Trp Thr Asn Asp Gly Ile Glu Ile Thr Leu Arg
545                 550                 555                 560
```

```
Glu Pro Leu Val Leu Asp Arg Ala Pro Ser Leu Glu Lys Pro Gly Phe
                565                 570                 575

Trp Leu Pro Lys Ala Ile Ser Glu Val Ile Gly Asn Gln Thr Lys Leu
            580                 585                 590

Glu Ala Gln Arg Arg Lys Lys Leu Glu Asp Glu Asp Thr Glu Tyr Met
        595                 600                 605

Gly Ala Ser Ile Glu Ile Ser Ala
    610                 615

<210> SEQ ID NO 34
<211> LENGTH: 681
<212> TYPE: PRT
<213> ORGANISM: Oryza sativa

<400> SEQUENCE: 34

Met Ala Lys Pro Leu Leu Pro Ala Thr Val Ala Ala Ala Ala Ala Ala
1               5                   10                  15

Ala Arg Leu Pro Ser Arg Leu Ala Val Gly Ala Ala Pro Pro Phe Arg
                20                  25                  30

Val Leu Pro Phe Phe Leu Cys Pro Pro Gln Ser Arg Ser Leu Ser
            35                  40                  45

Phe Ser Pro Val Ser Ala Val Ser Thr Ala Gly Lys Arg Gly Arg Ser
        50                  55                  60

Pro Pro Pro Pro Ser Pro Val Ile Ser Glu Gly Arg Asp Asp Glu
65                  70                  75                  80

Asp Ala Ala Val Gly Arg Pro Val Cys Pro Gly Cys Gly Val Phe Met
                85                  90                  95

Gln Asp Ala Asp Pro Asn Leu Pro Gly Phe Phe Lys Asn Pro Ser Arg
                100                 105                 110

Leu Ser Asp Asp Glu Met Gly Glu Asp Gly Ser Pro Pro Leu Ala Ala
            115                 120                 125

Glu Pro Asp Gly Phe Leu Gly Asp Glu Glu Asp Gly Ala Pro Ser
        130                 135                 140

Glu Ser Asp Leu Ala Ala Glu Leu Asp Gly Leu Asp Ser Asp Leu Asp
145                 150                 155                 160

Glu Phe Leu Glu Glu Glu Asp Glu Asn Gly Glu Asp Gly Ala Glu Met
                165                 170                 175

Lys Ala Asp Ile Asp Ala Lys Ile Asp Gly Phe Ser Ser Asp Trp Asp
            180                 185                 190

Ser Asp Trp Asp Glu Glu Met Glu Asp Glu Glu Lys Trp Arg Lys
        195                 200                 205

Glu Leu Asp Gly Phe Thr Pro Pro Gly Val Gly Tyr Gly Lys Ile Thr
    210                 215                 220

Glu Glu Thr Leu Glu Arg Trp Lys Lys Glu Lys Leu Ser Lys Ser Glu
225                 230                 235                 240

Arg Lys Arg Arg Ala Arg Glu Ala Lys Lys Ala Glu Ala Glu Glu Asp
                245                 250                 255

Ala Ala Val Val Cys Ala Arg Cys His Ser Leu Arg Asn Tyr Gly His
            260                 265                 270

Val Lys Asn Asp Lys Ala Glu Asn Leu Ile Pro Asp Phe Asp Phe Asp
        275                 280                 285

Arg Phe Ile Ser Ser Arg Leu Met Lys Arg Ser Ala Gly Thr Pro Val
    290                 295                 300

Ile Val Met Val Ala Asp Cys Ala Asp Phe Asp Gly Ser Phe Pro Lys
305                 310                 315                 320
```

Arg Ala Ala Lys Ser Leu Phe Lys Ala Leu Glu Gly Arg Gly Thr Ser
            325                 330                 335

Lys Leu Ser Glu Thr Pro Arg Leu Val Leu Gly Thr Lys Val Asp
        340                 345                 350

Leu Leu Pro Trp Gln Gln Met Gly Val Arg Leu Glu Lys Trp Val Arg
        355                 360                 365

Gly Arg Ala Lys Ala Phe Gly Ala Pro Lys Leu Asp Ala Val Phe Leu
    370                 375                 380

Ile Ser Val His Lys Asp Leu Ser Val Arg Asn Leu Ile Ser Tyr Val
385                 390                 395                 400

Lys Glu Leu Ala Gly Pro Arg Ser Asn Val Trp Val Ile Gly Ala Gln
                405                 410                 415

Asn Ala Gly Lys Ser Thr Leu Ile Asn Ala Phe Ala Lys Lys Gln Gly
                420                 425                 430

Val Lys Ile Thr Arg Leu Thr Glu Ala Ala Val Pro Gly Thr Thr Leu
            435                 440                 445

Gly Ile Leu Arg Ile Thr Gly Val Leu Pro Ala Lys Ala Lys Met Tyr
    450                 455                 460

Asp Thr Pro Gly Leu Leu His Pro Tyr Ile Met Ser Met Arg Leu Asn
465                 470                 475                 480

Ser Glu Glu Arg Lys Met Val Glu Ile Arg Lys Glu Leu Arg Pro Arg
                485                 490                 495

Cys Phe Arg Val Lys Ala Gly Gln Ser Val His Ile Gly Gly Leu Thr
                500                 505                 510

Arg Leu Asp Val Leu Lys Ala Ser Val Gln Thr Ile Tyr Ile Thr Val
            515                 520                 525

Trp Ala Ser Pro Ser Val Ser Leu His Leu Gly Lys Thr Glu Asn Ala
    530                 535                 540

Glu Leu Arg Asp Lys His Phe Gly Ile Arg Leu Gln Pro Pro Ile
545                 550                 555                 560

Arg Pro Glu Arg Val Ala Glu Leu Gly His Trp Thr Glu Arg Gln Ile
                565                 570                 575

Asp Val Ser Gly Val Ser Trp Asp Val Asn Ser Met Asp Ile Ala Ile
            580                 585                 590

Ser Gly Leu Gly Trp Tyr Ser Leu Gly Leu Lys Gly Asn Ala Thr Val
    595                 600                 605

Ala Val Trp Thr Phe Asp Gly Ile Asp Val Thr Arg Arg Asp Ala Met
    610                 615                 620

Ile Leu His Arg Ala Gln Phe Leu Glu Arg Pro Gly Phe Trp Leu Pro
625                 630                 635                 640

Ile Ala Ile Ala Asn Ala Ile Gly Glu Glu Thr Arg Lys Lys Asn Glu
                645                 650                 655

Arg Arg Lys Lys Ala Glu Gln Arg Asp Asp Leu Leu Leu Glu Glu Ser
                660                 665                 670

Ala Glu Asp Asp Val Glu Val Leu Ile
            675                 680

<210> SEQ ID NO 35
<211> LENGTH: 597
<212> TYPE: PRT
<213> ORGANISM: Arabidopsis thaliana

<400> SEQUENCE: 35

Met Leu Ser Lys Ala Ala Arg Glu Leu Ser Ser Ser Lys Leu Lys Pro
1               5                   10                  15

Leu Phe Ala Leu His Leu Ser Ser Phe Lys Ser Ser Ile Pro Thr Lys
            20                  25                  30

Pro Asn Pro Ser Pro Ser Tyr Leu Asn Pro His His Phe Asn Asn
            35                  40                  45

Ile Ser Lys Pro Pro Phe Leu Arg Phe Tyr Ser Ser Ser Ser Ser
 50                  55                  60

Asn Leu Leu Pro Leu Asn Arg Asp Gly Asn Tyr Asn Asp Thr Thr Ser
 65                  70                  75                  80

Ile Thr Ile Ser Val Cys Pro Gly Cys Gly Val His Met Gln Asn Ser
                 85                  90                  95

Asn Pro Lys His Pro Gly Phe Phe Ile Lys Pro Ser Thr Glu Lys Gln
                100                 105                 110

Arg Asn Asp Leu Asn Leu Arg Asp Leu Thr Pro Ile Ser Gln Glu Pro
                115                 120                 125

Glu Phe Ile Asp Ser Ile Lys Arg Gly Phe Ile Ile Glu Pro Ile Ser
            130                 135                 140

Ser Ser Asp Leu Asn Pro Arg Asp Asp Glu Pro Ser Asp Ser Arg Pro
145                 150                 155                 160

Leu Val Cys Ala Arg Cys His Ser Leu Arg His Tyr Gly Arg Val Lys
                165                 170                 175

Asp Pro Thr Val Glu Asn Leu Leu Pro Asp Phe Asp Phe Asp His Thr
            180                 185                 190

Val Gly Arg Arg Leu Gly Ser Ala Ser Gly Ala Arg Thr Val Val Leu
            195                 200                 205

Met Val Val Asp Ala Ser Asp Phe Asp Gly Ser Phe Pro Lys Arg Val
 210                 215                 220

Ala Lys Leu Val Ser Arg Thr Ile Asp Glu Asn Asn Met Ala Trp Lys
225                 230                 235                 240

Glu Gly Lys Ser Gly Asn Val Pro Arg Val Val Val Val Thr Lys
                245                 250                 255

Ile Asp Leu Leu Pro Ser Ser Leu Ser Pro Asn Arg Phe Glu Gln Trp
            260                 265                 270

Val Arg Leu Arg Ala Arg Glu Gly Gly Leu Ser Lys Ile Thr Lys Leu
            275                 280                 285

His Phe Val Ser Pro Val Lys Asn Trp Gly Ile Lys Asp Leu Val Glu
            290                 295                 300

Asp Val Ala Ala Met Ala Gly Lys Arg Gly His Val Trp Ala Val Gly
305                 310                 315                 320

Ser Gln Asn Ala Gly Lys Ser Thr Leu Ile Asn Ala Val Gly Lys Val
                325                 330                 335

Val Gly Gly Lys Val Trp His Leu Thr Glu Ala Pro Val Pro Gly Thr
            340                 345                 350

Thr Leu Gly Ile Ile Arg Ile Glu Gly Val Leu Pro Phe Glu Ala Lys
            355                 360                 365

Leu Phe Asp Thr Pro Gly Leu Leu Asn Pro His Gln Ile Thr Thr Arg
            370                 375                 380

Leu Thr Arg Glu Glu Gln Arg Leu Val His Ile Ser Lys Glu Leu Lys
385                 390                 395                 400

Pro Arg Thr Tyr Arg Ile Lys Glu Gly Tyr Thr Val His Ile Gly Gly
                405                 410                 415

Leu Met Arg Leu Asp Ile Asp Glu Ala Ser Val Asp Ser Leu Tyr Val
                420                 425                 430

Thr Val Trp Ala Ser Pro Tyr Val Pro Leu His Met Gly Lys Lys Glu

```
                    435                 440                 445
Asn Ala Tyr Lys Thr Leu Glu Asp His Phe Gly Cys Arg Leu Gln Pro
            450                 455                 460
Pro Ile Gly Glu Lys Arg Val Glu Glu Leu Gly Lys Trp Val Arg Lys
465                 470                 475                 480
Glu Phe Arg Val Ser Gly Thr Ser Trp Asp Thr Ser Ser Val Asp Ile
                485                 490                 495
Ala Val Ser Gly Leu Gly Trp Phe Ala Leu Gly Leu Lys Gly Asp Ala
            500                 505                 510
Ile Leu Gly Val Trp Thr His Glu Gly Ile Asp Val Phe Cys Arg Asp
            515                 520                 525
Ser Leu Leu Pro Gln Arg Ala His Thr Phe Glu Asp Ser Gly Phe Thr
            530                 535                 540
Val Ser Lys Ile Val Ala Lys Ala Asp Arg Asn Phe Asn Gln Ile His
545                 550                 555                 560
Lys Glu Glu Thr Gln Lys Lys Arg Lys Pro Asn Lys Ser Phe Ser Asp
                565                 570                 575
Ser Val Ser Asp Arg Asp Asn Ser Arg Glu Val Ser Gln Pro Ser Asp
            580                 585                 590
Ile Leu Pro Thr Met
            595

<210> SEQ ID NO 36
<211> LENGTH: 561
<212> TYPE: PRT
<213> ORGANISM: Arabidopsis thaliana

<400> SEQUENCE: 36

Met Ala Leu Arg Thr Leu Ser Thr Phe Pro Ser Leu Pro Arg Arg His
1               5                   10                  15
Thr Thr Thr Arg Arg Glu Pro Asn Leu Thr Val Ile Tyr Arg Asn Pro
            20                  25                  30
Thr Thr Ser Ile Val Cys Lys Ser Ile Ala Asn Ser Glu Pro Pro Val
        35                  40                  45
Ser Leu Ser Glu Arg Asp Gly Phe Ala Ala Ala Pro Thr Pro Gly
50                  55                  60
Glu Arg Phe Leu Glu Asn Gln Arg Ala His Glu Ala Gln Lys Val Val
65                  70                  75                  80
Lys Lys Glu Ile Lys Lys Glu Lys Lys Lys Glu Glu Ile Ile
                85                  90                  95
Ala Arg Lys Val Val Asp Thr Ser Val Ser Cys Cys Tyr Gly Cys Gly
            100                 105                 110
Ala Pro Leu Gln Thr Ser Asp Val Asp Ser Pro Gly Phe Val Asp Leu
            115                 120                 125
Val Thr Tyr Glu Leu Lys Lys Lys His His Gln Leu Arg Thr Met Ile
        130                 135                 140
Cys Gly Arg Cys Gln Leu Leu Ser His Gly His Met Ile Thr Ala Val
145                 150                 155                 160
Gly Gly Asn Gly Gly Tyr Pro Gly Gly Lys Gln Phe Val Ser Ala Asp
            165                 170                 175
Glu Leu Arg Glu Lys Leu Ser His Leu Arg His Glu Lys Ala Leu Ile
            180                 185                 190
Val Lys Leu Val Asp Ile Val Asp Phe Asn Gly Ser Phe Leu Ala Arg
        195                 200                 205
Val Arg Asp Leu Val Gly Ala Asn Pro Ile Ile Leu Val Ile Thr Lys
```

210                 215                 220
Ile Asp Leu Leu Pro Lys Gly Thr Asp Met Asn Cys Ile Gly Asp Trp
225                 230                 235                 240

Val Val Glu Val Thr Met Arg Lys Lys Leu Asn Val Leu Ser Val His
                245                 250                 255

Leu Thr Ser Ser Lys Ser Leu Asp Gly Val Ser Gly Val Ala Ser Glu
                260                 265                 270

Ile Gln Lys Glu Lys Lys Gly Arg Asp Val Tyr Ile Leu Gly Ala Ala
            275                 280                 285

Asn Val Gly Lys Ser Ala Phe Ile Asn Ala Leu Leu Lys Thr Met Ala
        290                 295                 300

Glu Arg Asp Pro Val Ala Ala Ala Gln Lys Tyr Lys Pro Ile Gln
305                 310                 315                 320

Ser Ala Val Pro Gly Thr Thr Leu Gly Pro Ile Gln Ile Asn Ala Phe
                325                 330                 335

Val Gly Gly Glu Lys Leu Tyr Asp Thr Pro Gly Val His Leu His His
                340                 345                 350

Arg Gln Ala Ala Val Val His Ser Asp Asp Leu Pro Ala Leu Ala Pro
            355                 360                 365

Gln Asn Arg Leu Arg Gly Gln Ser Phe Asp Ile Ser Thr Leu Pro Thr
370                 375                 380

Gln Ser Ser Ser Ser Pro Lys Gly Glu Ser Leu Asn Gly Tyr Thr Phe
385                 390                 395                 400

Phe Trp Gly Gly Leu Val Arg Ile Asp Ile Leu Lys Ala Leu Pro Glu
                405                 410                 415

Thr Cys Phe Thr Phe Tyr Gly Pro Lys Ala Leu Glu Ile His Ala Val
                420                 425                 430

Pro Thr Lys Thr Ala Thr Ala Phe Tyr Glu Lys Glu Leu Gly Val Leu
            435                 440                 445

Leu Thr Pro Pro Ser Gly Lys Asn Gln Met Gln Glu Trp Lys Gly Leu
        450                 455                 460

Gln Ser His Arg Leu Leu Gln Ile Glu Ile Asn Asp Ala Lys Arg Pro
465                 470                 475                 480

Ala Ser Asp Val Ala Ile Ser Gly Leu Gly Trp Ile Ser Ile Glu Pro
                485                 490                 495

Ile Arg Lys Thr Arg Gly Thr Glu Pro Arg Asp Leu Asn Glu Ala Glu
                500                 505                 510

His Glu Ile His Ile Cys Val Ser Val Pro Lys Pro Val Glu Val Phe
            515                 520                 525

Leu Arg Pro Thr Leu Pro Ile Gly Thr Ser Gly Thr Glu Trp Tyr Gln
        530                 535                 540

Tyr Arg Glu Leu Thr Asp Lys Glu Glu Val Arg Pro Lys Trp Tyr
545                 550                 555                 560

Phe

<210> SEQ ID NO 37
<211> LENGTH: 366
<212> TYPE: PRT
<213> ORGANISM: Bacillus subtilis

<400> SEQUENCE: 37

Met Glu Lys Val Val Cys Ile Gly Cys Gly Val Thr Ile Gln Thr Glu
1               5                   10                  15

Asp Lys Thr Gly Leu Gly Tyr Ala Pro Pro Ala Ser Leu Thr Lys Glu
            20                  25                  30

```
Asn Val Ile Cys Gln Arg Cys Phe Arg Leu Lys Asn Tyr Asn Glu Ile
         35                  40                  45
Gln Asp Val Ser Leu Thr Asp Asp Phe Leu Asn Ile Leu His Gly
     50                  55                  60
Ile Gly Glu Thr Asp Ser Leu Val Val Lys Ile Val Asp Ile Phe Asp
65                   70                  75                  80
Phe Asn Gly Ser Trp Ile Asn Gly Leu Gln Arg Leu Val Gly Gly Asn
                 85                  90                  95
Pro Ile Leu Leu Val Gly Asn Lys Ala Asp Ile Leu Pro Lys Ser Leu
                100                 105                 110
Lys Arg Glu Arg Leu Ile Gln Trp Met Lys Arg Glu Ala Lys Glu Leu
             115                 120                 125
Gly Leu Lys Pro Val Asp Val Phe Leu Val Ser Ala Gly Arg Gly Gln
         130                 135                 140
Gly Ile Arg Glu Val Ile Asp Ala Ile Glu His Tyr Arg Asn Gly Lys
145                 150                 155                 160
Asp Val Tyr Val Val Gly Cys Thr Asn Val Gly Lys Ser Thr Phe Ile
                165                 170                 175
Asn Arg Ile Ile Lys Glu Val Ser Gly Glu Glu Asp Ile Ile Thr Thr
             180                 185                 190
Ser Gln Phe Pro Gly Thr Thr Leu Asp Ala Ile Glu Ile Pro Leu Asp
         195                 200                 205
Asp Gly Ser Ser Leu Tyr Asp Thr Pro Gly Ile Ile Asn Asn His Gln
    210                 215                 220
Met Ala His Tyr Val Asn Lys Lys Asp Leu Lys Ile Leu Ser Pro Lys
225                 230                 235                 240
Lys Glu Leu Lys Pro Arg Thr Phe Gln Leu Asn Asp Gln Gln Thr Leu
                245                 250                 255
Tyr Phe Gly Gly Leu Ala Arg Phe Asp Tyr Val Ser Gly Glu Arg Ser
             260                 265                 270
Pro Phe Ile Cys Tyr Met Pro Asn Glu Leu Met Ile His Arg Thr Lys
         275                 280                 285
Leu Glu Asn Ala Asp Ala Leu Tyr Glu Lys His Ala Gly Glu Leu Leu
    290                 295                 300
Thr Pro Pro Gly Lys Asp Glu Met Asp Glu Phe Pro Glu Leu Val Ala
305                 310                 315                 320
His Thr Phe Thr Ile Lys Asp Lys Lys Thr Asp Ile Val Phe Ser Gly
                325                 330                 335
Leu Gly Trp Val Thr Val His Asp Ala Asp Lys Lys Val Thr Ala Tyr
             340                 345                 350
Ala Pro Lys Gly Val His Val Phe Val Arg Arg Ser Leu Ile
         355                 360                 365
```